United States Patent
Burns et al.

(10) Patent No.: US 12,252,520 B2
(45) Date of Patent: Mar. 18, 2025

(54) MYOSIN 15 PROMOTERS AND USES THEREOF

(71) Applicants: Decibel Therapeutics, Inc., Boston, MA (US); Regeneron Pharmaceuticals, Inc., Tarrytown, NY (US)

(72) Inventors: Joseph Burns, Newton, MA (US); Kathryn Ellis, Arlington, MA (US); Adam Palermo, Somerville, MA (US); Martin Schwander, Auburndale, MA (US); Jonathon Whitton, Cambridge, MA (US); Leah Sabin, Goldens Bridge, NY (US); Christos Kyratsous, Irvington, NY (US); Meghan Drummond Samuelson, Katonah, NY (US)

(73) Assignees: Decibel Therapeutics, Inc., Boston, MA (US); Regeneron Pharmaceuticals, Inc., Tarrytown, NY (US)

( * ) Notice: Subject to any disclaimer, the term of this patent is extended or adjusted under 35 U.S.C. 154(b) by 840 days.

(21) Appl. No.: 17/395,773

(22) Filed: Aug. 6, 2021

(65) Prior Publication Data
US 2021/0388045 A1    Dec. 16, 2021

Related U.S. Application Data

(63) Continuation of application No. PCT/US2020/017292, filed on Feb. 7, 2020.

(60) Provisional application No. 62/965,773, filed on Jan. 24, 2020, provisional application No. 62/928,311, filed on Oct. 30, 2019, provisional application No. 62/802,874, filed on Feb. 8, 2019.

(51) Int. Cl.
| *C07K 14/47* | (2006.01) |
| *A61K 38/00* | (2006.01) |
| *A61K 48/00* | (2006.01) |
| *C12N 15/86* | (2006.01) |

(52) U.S. Cl.
CPC ...... *C07K 14/4716* (2013.01); *A61K 48/0058* (2013.01); *C12N 15/86* (2013.01); *A61K 38/00* (2013.01); *C12N 2750/14143* (2013.01)

(58) Field of Classification Search
CPC ............ C07K 14/4716; A61K 48/0058; A61K 38/00; A61K 48/005; C12N 15/86; C12N 2750/14143; C12N 2830/008
See application file for complete search history.

(56) References Cited

U.S. PATENT DOCUMENTS

| 6,436,392 | B1 | 8/2002 | Engelhardt et al. |
| 6,544,786 | B1 | 4/2003 | Xiao et al. |
| 6,808,922 | B1 | 10/2004 | Bebbington et al. |
| 6,897,045 | B2 | 5/2005 | Engelhardt et al. |
| 7,803,622 | B2 | 9/2010 | Engelhardt et al. |
| 8,236,557 | B2 | 8/2012 | Dongsheng et al. |
| 8,298,818 | B2 | 10/2012 | Boye et al. |
| 11,660,353 | B2 | 5/2023 | Burns et al. |
| 2003/0219741 | A1 | 11/2003 | Isogai et al. |
| 2004/0072154 | A1 | 4/2004 | Morris et al. |
| 2007/0161031 | A1 | 7/2007 | Trinklein et al. |
| 2008/0249052 | A1 | 10/2008 | Duan et al. |
| 2010/0003218 | A1 | 1/2010 | Duan et al. |
| 2010/0266551 | A1 | 10/2010 | Richard et al. |
| 2012/0003190 | A1 | 1/2012 | Yamoah et al. |
| 2013/0210895 | A1 | 8/2013 | Boye et al. |
| 2014/0256802 | A1 | 9/2014 | Boye et al. |
| 2015/0065562 | A1 | 3/2015 | Yazicioglu et al. |
| 2015/0209406 | A1* | 7/2015 | Chen ............... A61P 27/16 435/377 |
| 2016/0076054 | A1 | 3/2016 | Auricchio et al. |
| 2018/0055908 | A1 | 3/2018 | Petit et al. |
| 2018/0327779 | A1 | 11/2018 | Colella et al. |
| 2019/0002916 | A1 | 1/2019 | Kalatzis et al. |
| 2019/0153050 | A1 | 5/2019 | Boye et al. |
| 2019/0185864 | A1 | 6/2019 | Simons et al. |
| 2020/0155705 | A1* | 5/2020 | Burns ............... A61K 48/0075 |
| 2020/0157573 | A1 | 5/2020 | Boye et al. |
| 2021/0236654 | A1 | 8/2021 | Burns et al. |

(Continued)

FOREIGN PATENT DOCUMENTS

| WO | WO-01/25465 A1 | 4/2001 |
| WO | WO-2009/100438 A2 | 8/2009 |

(Continued)

OTHER PUBLICATIONS

Lovell, "Mouse DNA sequence from clone RP23-135F6 on chromosome 11," European Nucleotide Archive, EMBL-EBI. (2012) (15 pages).
Higashimoto et al., "The woodchuck hepatitis virus post-transcriptional regulatory element reduces readthrough transcription from retroviral vectors," Gene Ther. 14(17):1298-304 (2007).
Wang, Aihui, Dissertation: "Molecular Cloning of an Unconventional Myosin MYO15 and the Identification of Mutations of MYO15 Responsible for Human Nonsyndromic Deafness DFNB3," Doctor of Philosophy, Graduate Program in Genetics, Michigan State University (1999) (140 pages).
Liang et al., "Characterization of the Human and Mouse Unconventional Myosin XV Genes Responsible for Hereditary Deafness DFNB3 and Shaker 2," Genomics. 61(3):243-258 (1999).

(Continued)

*Primary Examiner* — Nancy J Leith
*Assistant Examiner* — Kyle T Rega
(74) *Attorney, Agent, or Firm* — Clark & Elbing LLP

(57) ABSTRACT

The disclosure provides polynucleotides containing regions of the Myosin 15 (Myo15) promoter, as well as vectors containing the same, that can be used to promote expression of a transgene specifically in hair cells. The polynucleotides described herein may be operably linked to a transgene, such as a transgene encoding a therapeutic protein, so as to promote hair cell-specific expression of the transgene. The polynucleotides described herein may be operably linked to a therapeutic transgene and used for the treatment of subjects having or at risk of developing hearing loss or vestibular dysfunction.

13 Claims, 32 Drawing Sheets

Specification includes a Sequence Listing.

(56) References Cited

U.S. PATENT DOCUMENTS

| | | |
|---|---|---|
| 2021/0395781 A1 | 12/2021 | Burns et al. |
| 2022/0064671 A1 | 3/2022 | Maranga et al. |
| 2022/0265865 A1 | 8/2022 | Burns et al. |
| 2024/0131186 A1 | 4/2024 | Burns et al. |
| 2024/0148905 A1 | 5/2024 | Palermo et al. |
| 2024/0309399 A1 | 9/2024 | Hu et al. |

FOREIGN PATENT DOCUMENTS

| | | |
|---|---|---|
| WO | WO-2013/075008 A1 | 5/2013 |
| WO | WO-2013/158879 A1 | 10/2013 |
| WO | WO-2014/193716 A2 | 12/2014 |
| WO | WO-2016/131981 A1 | 8/2016 |
| WO | WO-2016/139321 A1 | 9/2016 |
| WO | WO-2017/100791 A1 | 6/2017 |
| WO | WO-2018/039375 A1 | 3/2018 |
| WO | WO-2018/145111 A1 | 8/2018 |
| WO | WO-2018/204734 A1 | 11/2018 |
| WO | WO-2019/162396 A1 | 8/2019 |
| WO | WO-2019/165292 A1 | 8/2019 |
| WO | WO-2020/093018 A1 | 5/2020 |
| WO | WO-2020/097372 A1 | 5/2020 |
| WO | WO-2020/148458 A1 | 7/2020 |
| WO | WO-2020/163743 | 8/2020 |
| WO | WO-2020/163743 A1 | 8/2020 |
| WO | WO-2021/087296 A1 | 5/2021 |
| WO | WO-2024/173835 A2 | 8/2024 |

OTHER PUBLICATIONS

Yuhe, Liu, "Preparation of adeno-associated virus vector and its application in cochlea transgenic research," Chinese Journal of Otology. 4(4):343-347 (2006) (6 pages).

Belyantseva et al., "Myosin XVa localizes to the tips of inner ear sensory cell stereocilia and is essential for staircase formation of the hair bundle," Proc Natl Acad Sci U S A. 100(24):13958-63 (2003).

GenBank Accession No. JN957158.1, "Mus musculus targeted non-conditional, lacZ-tagged mutant allele Myo15:tm1e(EUCOMM)Wtsi; transgenic," retrieved from <https://www.ncbi.nlm.nih.gov/nucleotide/JN957158.1>, dated Nov. 5, 2011 (12 pages).

International Search Report and Written Opinion for International Application No. PCT/US2020/017292, mailed Jun. 26, 2020 (18 pages).

GenBank Accession No. JN953192.1, "Mus musculus targeted KO-first, conditional ready, lacZ-tagged mutant allele Myo15:tm1a(EUCOMM)Wtsi; transgenic," retrieved from <https://www.ncbi.nlm.nih.gov/nuccore/JN953192>, dated Nov. 5, 2011 (11 pages).

Caberlotto et al., "Usher type 1G protein sans is a critical component of the tip-link complex, a structure controlling actin polymerization in stereocilia," Proc Natl Acad Sci U S A. 108(14):5825-30 (2011) (14 pages).

Schlabach et al., "Synthetic design of strong promoters," Proc Natl Acad Sci U S A. 107(6):2538-43 (2010).

International Search Report and Written Opinion for International Application No. PCT/US2019/029366, mailed Sep. 10, 2019 (17 pages).

Boëda et al., "A specific promoter of the sensory cells of the inner ear defined by transgenesis," Hum Mol Genet. 10(15):1581-1589 (2001).

Akil et al. "Dual AAV gene therapy restores hearing in a mouse model for human genetic Deafness," International Symposium on Inner Ear Therapies 2017. Abstract only.

Akil et al. "Dual AAV-mediated gene therapy restores hearing in a DFNB9 mouse model," PNAS. 116(10):4496-4501 (2019).

Al-Moyed et al., "A dual AAV viral vector approach partially restores exocytosis and rescues hearing in deaf otoferlin knock-out mice," ARO Abstracts. 41:76 (2018).

Al-Moyed et al. "A dual-AAV approach restores fast exocytosis and partially rescues auditory function in deaf otoferlin knock-out mice," EMBO Molecular Medicine. 11(e9396):1-13 (2019).

Alemi. "Progress Report: AOS Research Grant: Restoration of Hearing in the Otoferlin Knockout Mouse using Viral Gene Therapy," 145th Annual Meeting of the American Otological Society, Inc. 68 (2012). Abstract only.

Choi et al. "Identities and frequencies of mutations of the otoferlin gene (OTOF) causing DFNB9 deafness in Pakistan," Clin Genet. 75(3):237-243 (2009).

Duan et al. "Expanding AAV Packaging Capacity with Trans-splicing or Overlapping Vectors: A Quantitative Comparison," Mol Ther. 4(4):383-391 (2001).

McClements et al. "Adeno-associated Virus (AAV) Dual Vector Strategies for Gene Therapy Encoding Large Transgenes," Yale J Biol Med. 90:611-623 (2017).

Trapani et al. "Effective delivery of large genes to the retina by dual AAV vectors," EMBO Mol Med. 6(2):194-211 (2014).

Trapani et al. "Improved dual AAV vectors with reduced expression of truncated proteins are safe and effective in the retina of a mouse model of Stargardt disease," Human Molecular Genetics. 24(23):6811-6825 (2015).

Yasunaga et al. "OTOF Encodes Multiple Long and Short Isoforms: Genetic Evidence That the Long Ones Underlie Recessive Deafness DFNB9," Am J Hum Genet. 67:591-600 (2000).

International Search Report and Written Opinion for International Application No. PCT/US2020/017257, mailed Apr. 29, 2020 (22 pages).

Xu et al. "Trans-Splicing Adeno-Associated Viral Vector-Mediated Gene Therapy Is Limited by the Accumulation of Spliced mRNA but Not by Dual Vector Coinfection Efficiency," Hum Gene Ther. 15(9): 896-905 (2004).

Ghosh et al. "A Hybrid Vector System Expands Adeno-associated Viral Vector Packaging Capacity in a Transgene-independent Manner," The American Society of Gene Therapy. 16(1): 124-130 (2008).

Ghosh et al., "Efficient Transgene Reconstitution with Hybrid Dual AAV Vectors Carrying the Minimized Bridging Sequences," Hum Gene Ther. 22(1):77-88 (2011).

Michalski et al., "Genetics of auditory mechano-electrical transduction," Pflugers Arch. 467(1):49-72 (2015).

Skarnes et al., "A conditional knockout resource for the genome-wide study of mouse gene function," available in PMC Feb. 14, 2013, published in final edited form as: Nature. 474(7351):337-342 (2011) (18 pages).

Boye et al., "Transduction and Tropism of an Abbreviated Form of CMV-Chicken B-Actin Promoter (CBA) With AAV in Mouse Retina," ARVO Annual Meeting Abstract May 2006, published in: Investigative Ophthalmology & Visual Science. 47: 852 (2006) (2 pages) (Abstract only).

International Search Report and Written Opinion for International Patent Application No. PCT/US2020/058265, mailed Feb. 9, 2021 (15 pages).

Hirsch et al., "Delivering Transgenic DNA Exceeding the Carrying Capacity of AAV Vectors," available in PMC Aug. 3, 2016, published in final edited form as: Methods Mol Biol. 13382:21-39 (2016) (20 pages).

Majewski and Ott, "GT Repeats Are Associated with Recombination on Human Chromosome 22," Genome Res. 10(8): 1108-1144 (Aug. 2000) (7 pages).

Lostal et al., "Full-Length Dystrophin Reconstitution with Adeno-Associated Viral Vectors, " Human Gene Ther. 25(6): 552-562 (Jun. 2014) (11 pages).

Gao et al., "The Dystrophin Complex: structure, function and implications for therapy," available in PMC Jul. 1, 2016, published in final edited form as: Compr Physiol. 5(3): 1223-1239 (Jul. 2015) (33 pages).

Dyka et al., "Dual adeno-associated virus vectors result in efficient in vitro and in vivo expression of an oversized gene, MYO7A," Human Gene Ther Methods. 25(2): 166-77 (Apr. 2014) (12 pages).

(56) References Cited

OTHER PUBLICATIONS

Pryadkina et al., "A comparison of AAV strategies distinguishes overlapping vectors for efficient systemic delivery of the 6.2 kb Dysferlin coding sequence," Mol Ther Methods Clin Dev. 2: 15009 (Mar. 2015) (12 pages).
Geleoc et al., "Sound strategies for hearing restoration," available in PMC Aug. 29, 2014, published in final edited form as: Science. 344(6184):1241062 (May 2014) (20 pages).
Corns et al., "Mechanotransduction is required for establishing and maintaining mature inner hair cells and regulating efferent innervation," Nat Commun. 9(1):4015 (Oct. 2018) (15 pages).
Yoshimura et al., "Enhanced viral-mediated cochlear gene delivery in adult mice by combining canal fenestration with round window membrane inoculation," Scientific Reports. 8:2980 (with supplemental material) (Feb. 2018) (14 pages).
Pangrsic et al., "Otoferlin: a multi-C2 domain protein essential for hearing," Trends in Neurosciences. 35(11): 671-680 (2012) (10 pages).
Holt et al., "Split otoferlins reunited," EMBO Molecular Medicine. 11:(1)e9995 (Jan. 2019) (3 pages).
Suzuki et al., "Cochlear gene therapy with ancestral AAV in adult mice: complete transduction of inner hair cells without cochlear dysfunction," Scientific Reports. 7(1):45524 (Apr. 2017) (11 pages).
Tertrais et al., "Viral Transfer of Mini-Otoferlins Partially Restores the Fast Component of Exocytosis and Uncovers Ultrafast Endocytosis in Auditory Hair Cells of Otoferlin Knock-Out Mice," J. Neurosci. 39(18):3394-3411 (May 2019) (18 pages).
Petrs-Silva et al., "Novel Properties of Tyrosine-mutant AAV2 Vectors in the Mouse Retina," Molecular Therapy. 19(2):293-301 (Feb. 2011) (9 pages).
American Academy of Audiology, "Children's Hospital of Philadelphia Performs First Gene Therapy Procedure to Treat Genetic Hearing Loss in United States," <https://www.audiology.org/childrens-hospital-of-philadelphia-performs-first-gene-therapy-procedure-to-treat-genetic-hearing-loss-in-united-states/>, dated Jan. 26, 2024 (2 pages).
Yoshimura et al., "Targeted Allele Suppression Prevents Progressive Hearing Loss in the Mature Murine Model of Human TMC1 Deafness," Molecular Therapy. 27(3):681-690 (with supplemental material) (Mar. 2019) (17 pages).
Akil et al., "Surgical Method for Virally Mediated Gene Delivery to the Mouse Inner Ear through the Round Window Membrane," Journal of Visualized Experiments. 97(1):e52187 (Mar. 2015) (7 pages).
Liu et al., "Specific and Efficient Transduction of Cochlear Inner Hair Cells with Recombinant Adeno-associated Virus Type 3 Vector," Molecular Therapy. 12(4):725-733 (Oct. 2005) (9 pages).

"Basics of sound, the Ear, and Hearing," *Hearing Loss: Determining Eligibility for Social Security Benefits*. Edited by Robert A. Dobie and Susan Van Hemel, 42-68 (2004) (61 pages).
Akil et al., "AAV-Mediated Gene Delivery to the Inner Ear," *Adeno-Associated Virus Vectors: Design and Delivery*. Methods in Molecular Biology. Edited by Michael J. Castle, 271-282 (2019) [published online on Jan. 1, 2019] (16 pages).
Langouet-Astrie et al., "Characterization of intravitreally delivered capsid mutant AAV2-Cre vector to induce tissue-specific mutations in murine retinal ganglion cells," Experimental Eye Research. 151(1):61-67 (Jul. 2016) (7 pages).
Li et al., "A novel bispecific molecule delivered by recombinant AAV2 suppresses ocular inflammation and choroidal neovascularization," J. Cell. Mol. Med. 21(8):1555-1571 (Aug. 2017) (17 pages).
Lopes-Pacheco et al., "Self-complementary and tyrosine-mutant rAAV vectors enhance transduction in cystic fibrosis bronchial epithelial cells," Experimental Cell Research. 372:99-107 (Sep. 2018) (9 pages).
Petrs-Silva et al., "High-efficiency Transduction of the Mouse Retina by Tyrosine-mutant AAV Serotype Vectors," Molecular Therapy. 17(3):463-471 (Mar. 2009) (9 pages).
Kilpatrick et al., "Adeno-associated virus-mediated gene delivery into the scala media of the normal and deafened adult mouse ear," Gene Therapy. 18(6):569-578 (Jan. 2011) (10 pages).
Tao et al., "Delivery of Adeno-Associated Virus Vectors in Adult Mammalian Inner-Ear Cell Subtypes Without Auditory Dysfunction," Human Gene Therapy. 29(4):492-506 (Nov. 2017) (15 pages).
Zhang et al., "Cochlear Gene Therapy for Sensorineural Hearing Loss: Current Status and Major Remaining Hurdles for Translational Success," Front. Mol. Neurosci. 11(221):1-15 (Jun. 2018) (15 pages).
Roux et al., "Otoferlin, Defective in a Human Deafness Form, Is Essential for Exocytosis at the Auditory Ribbon Synapse," Cell. 127(2):277-289 (Oct. 2006) (13 pages).
"Genetic Hearing Loss With No. Associated Abnormalities," *Hereditary Hearing Loss and Its Syndromes, Third Edition*. Helga V. Toriello and Shelley D. Smith. 164-165 (2013) (4 pages).
Ahmed et al., "Emerging Gene Therapies for Genetic Hearing Loss," JARO. 18(5):649-670 (Aug. 2017) (22 pages).
Zhang et al., "Temperature sensitive auditory neuropathy," Hearing Research. 335(1):53-63 (Jan. 2016) (11 pages).
Hamosh et al. "OTOFERLIN; OTOF," OMIM. (Apr. 2015) (8 pages) retrieved via The Wayback Machine on Jul. 29, 2015, URL: <https://web.archive.org/web/20150729163826/http://omim.org/entry/603681>.
Kim et al., "Direct isolation and identification of promoters in the human genome," Genome Res. 15(6):830-9 (Jun. 2005) (11 pages).

\* cited by examiner

AAV with ubiquitous promoter:
- Expression in inner hair cells, some outer hair cells and many non-sensory cell types.

AAV with hair cell-specific promoter:
- Expression is restricted to inner hair cells and outer hair cells only.

FIG. 3A
AAV2/9 - Myo15 1kb - GFP
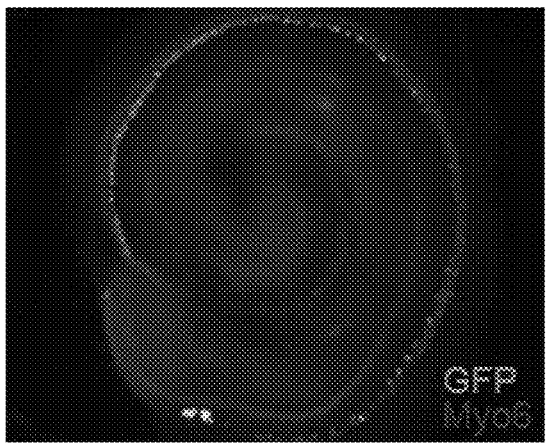
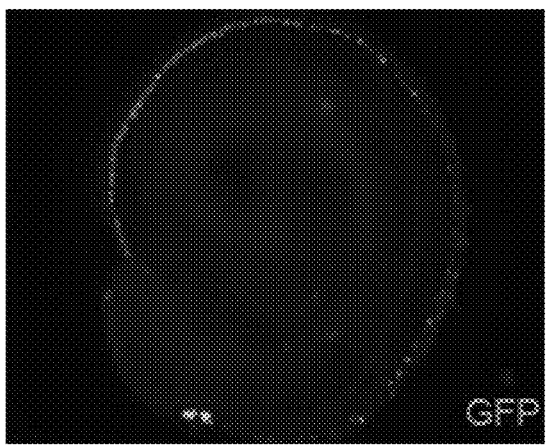
FIG. 3B
AAV2/9 - Myo15 mini intron - GFP
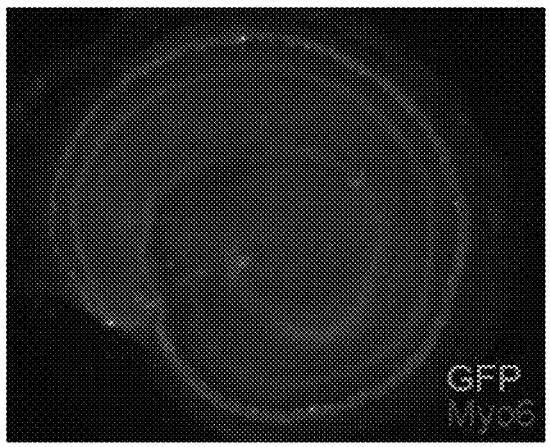
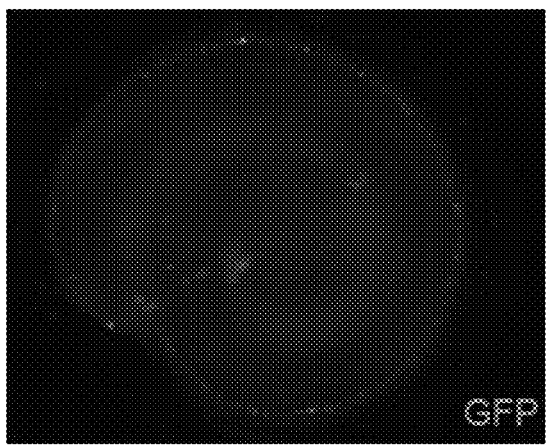

0.6 kb human Myo15

FIG. 4B
1.2 kb human Myo15
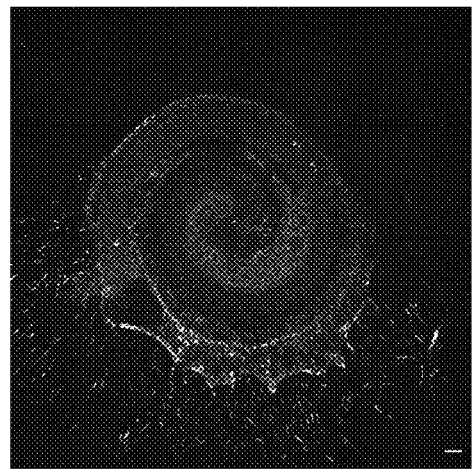
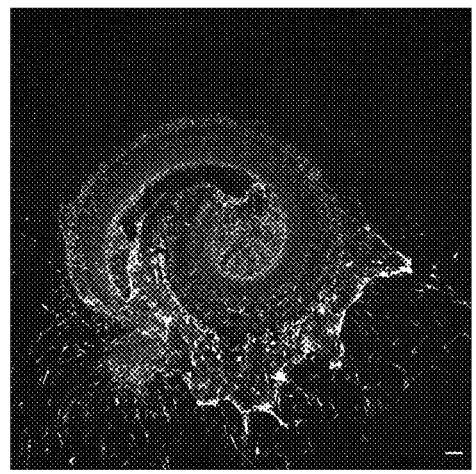

FIG. 4C
1 kb mouse Myo15
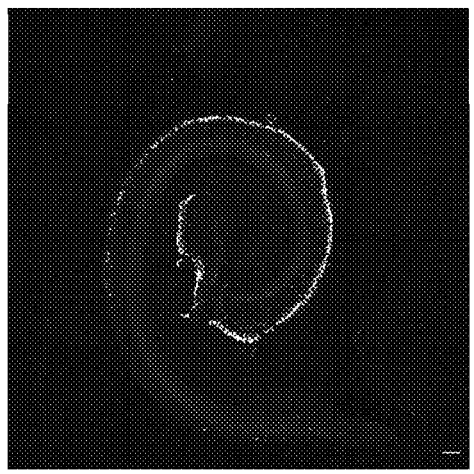
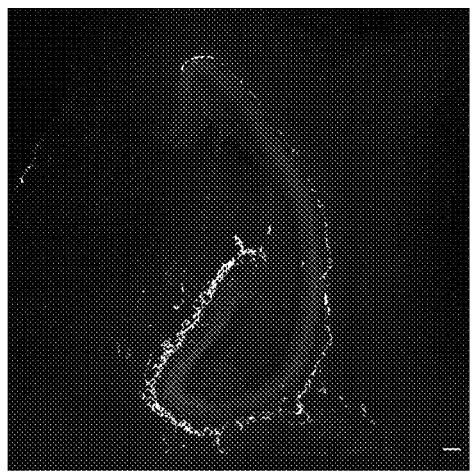

FIG. 4D
1.2 kb hMyo15
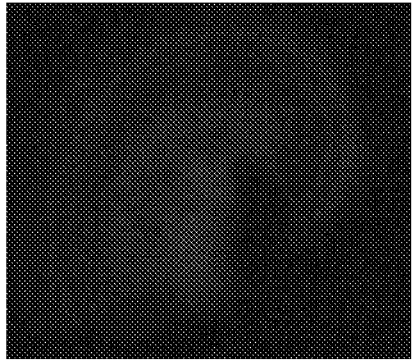
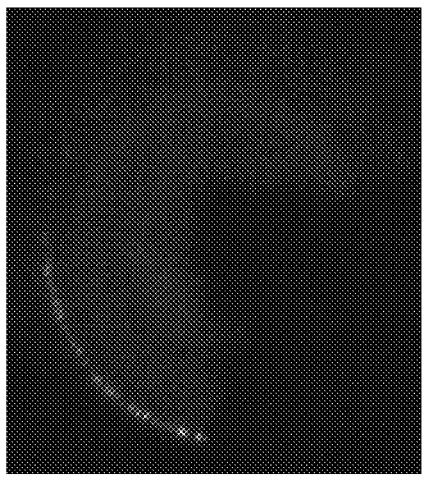
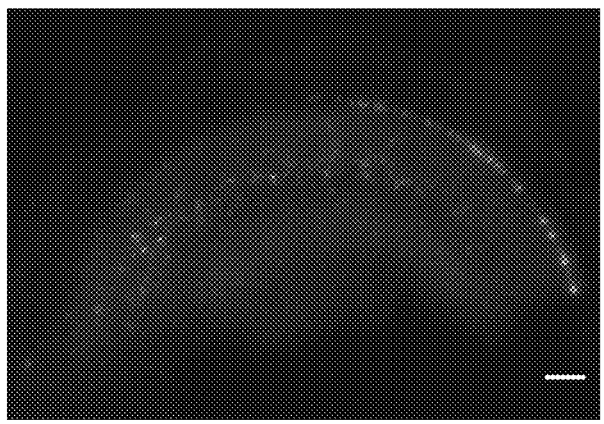
FIG. 4E
1.0 kb mMyo15
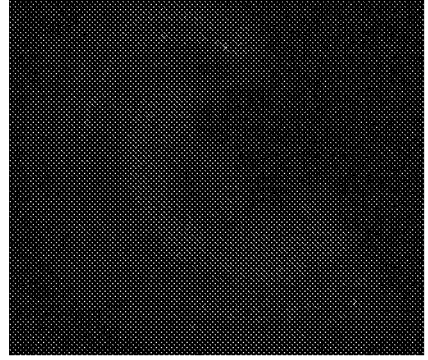
apex
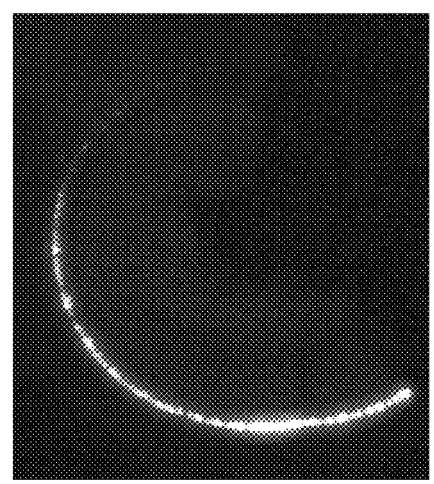
middle
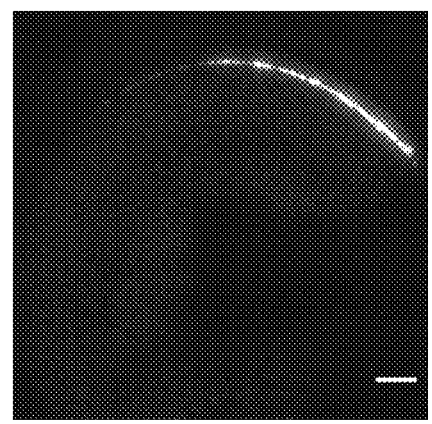
base

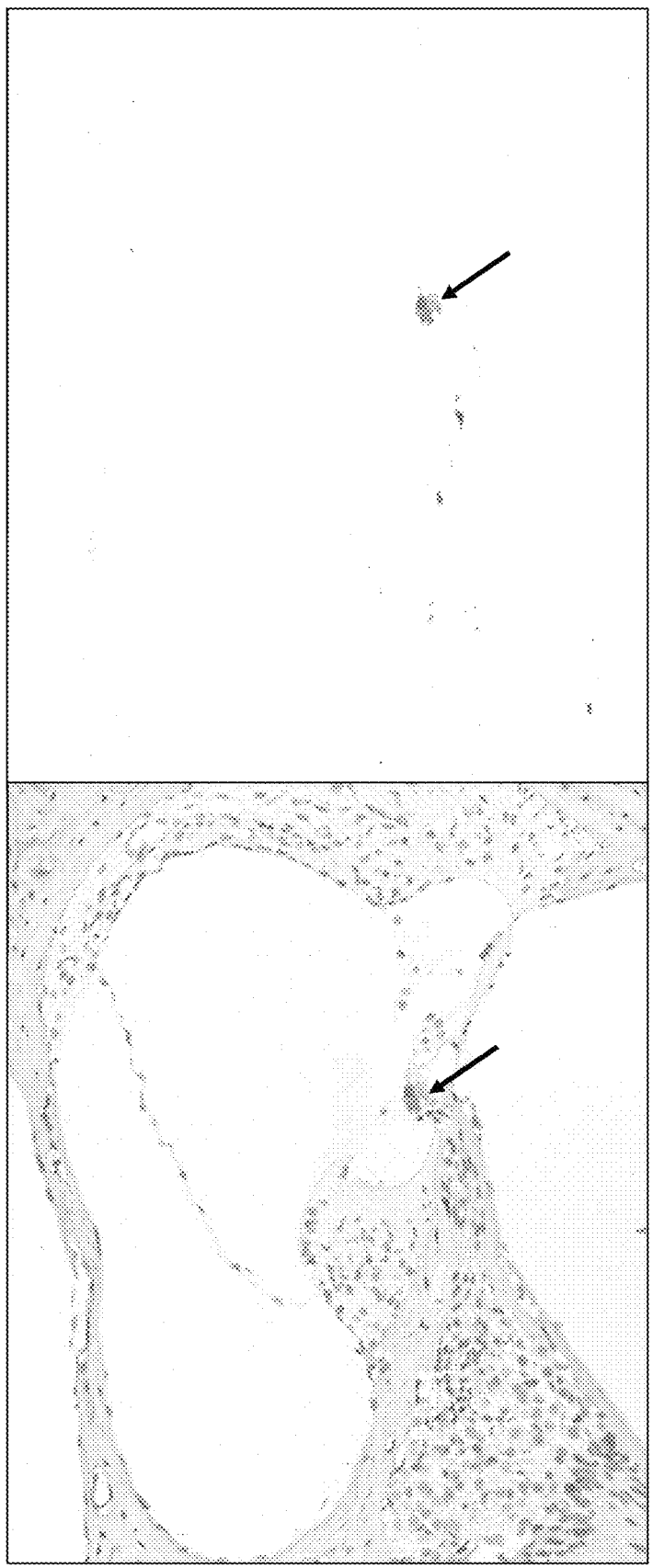
FIG. 4F  1.2 kb hMyo15

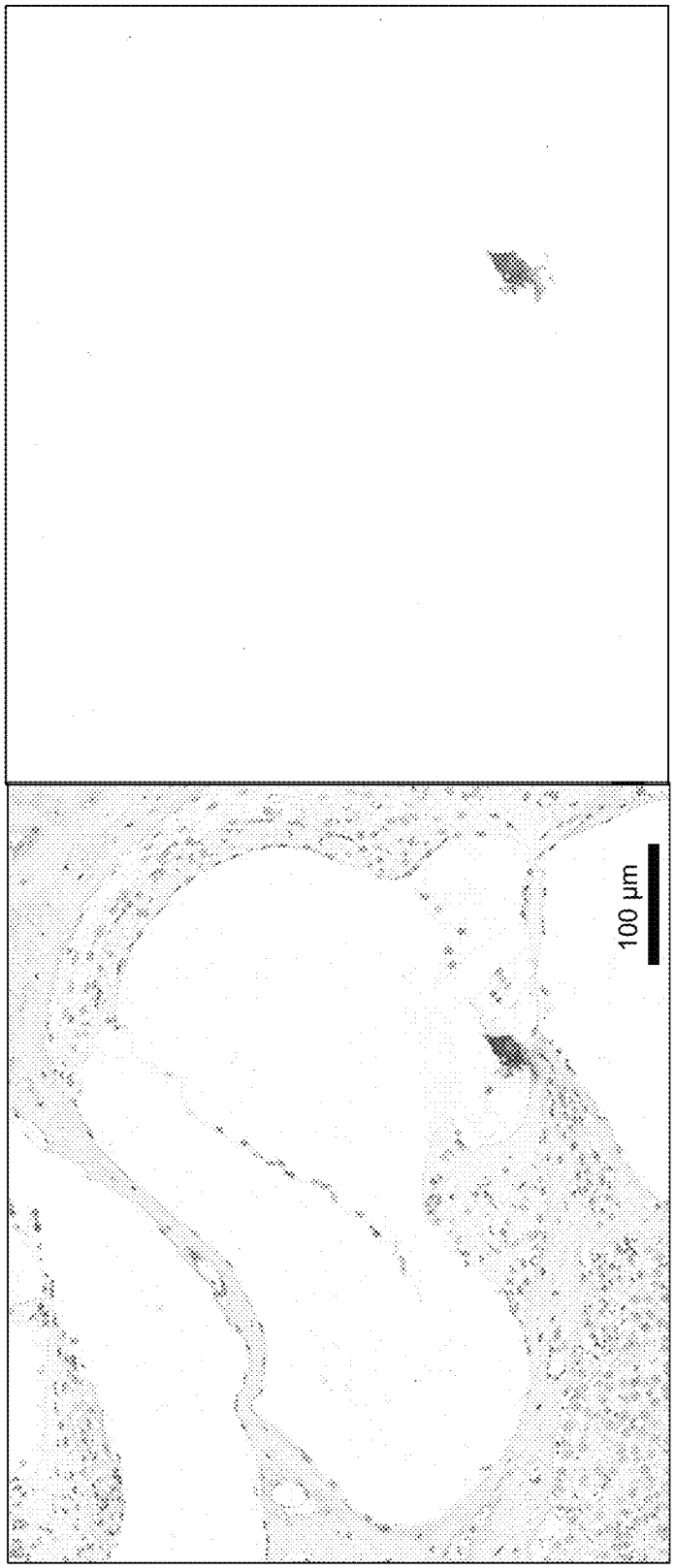

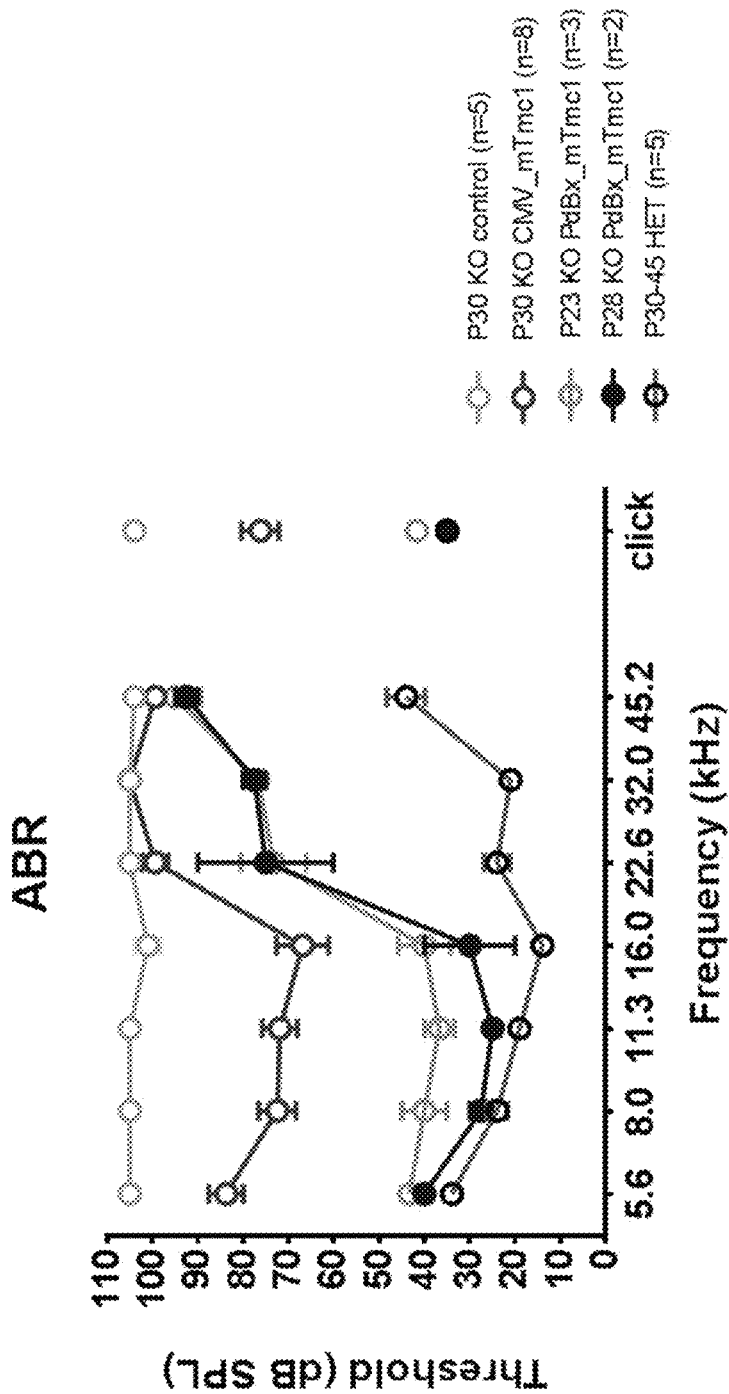

1.2 kb human Myosin 15 promoter-GFP 0.6kb human Myosin 15 promoter-GFP 2.8 kHz

MYOSIN 15 PROMOTERS AND USES THEREOF

SEQUENCE LISTING

The instant application contains a Sequence Listing which has been submitted electronically in ASCII format and is hereby incorporated by reference in its entirety. Said ASCII copy, created Aug. 4, 2021, is named 51471-002005_Sequence_Listing_8_04_21_ST25, and is 26,949 bytes in size.

FIELD OF THE INVENTION

Described herein are polynucleotides containing regions of the Myosin 15 (Myo15) promoter, as well as vectors comprising the same, that can be used to promote expression of a transgene in hair cells (e.g., cochlear hair cells, such as inner hair cells and outer hair cells, and/or vestibular hair cells). Also disclosed are methods of using the polynucleotides and vectors of the invention to achieve expression of transgenes in hair cells for the treatment of hearing loss and/or vestibular dysfunction.

BACKGROUND

Hearing loss is a major public health issue that is estimated to affect nearly 15% of school-age children and one out of three people by age sixty-five. The most common type of hearing loss is sensorineural hearing loss, a type of hearing loss caused by defects in the cells of the inner ear, such as cochlear hair cells, or the neural pathways that project from the inner ear to the brain. Sensorineural hearing loss is often acquired, and has a variety of causes, including acoustic trauma, disease or infection, head trauma, ototoxic drugs, and aging. There are also genetic causes of sensorineural hearing loss, such as mutations in genes involved in the development and function of the inner ear. Mutations in over 90 such genes have been identified, including mutations inherited in an autosomal recessive, autosomal dominant, and X-linked pattern.

Factors that disrupt the development, survival, or integrity of cochlear hair cells, such as genetic mutations, disease or infection, ototoxic drugs, head trauma, and aging, may similarly affect vestibular hair cells and are, therefore, also implicated in vestibular dysfunction, including vertigo, dizziness, and imbalance. Indeed, patients carrying mutations that disrupt hair cell development or function can present with both hearing loss and vestibular dysfunction, or either disorder alone. In recent years, efforts to treat hearing loss have increasingly focused on gene therapy as a possible solution; however, there remain few approaches to specifically target hair cells, which are frequently implicated in hearing loss and vestibular dysfunction. There is a need for new therapeutics to target hair cells for the treatment of sensorineural hearing loss or vestibular dysfunction.

SUMMARY OF THE INVENTION

The invention provides compositions and methods for promoting the expression of a gene of interest, such as a gene that promotes or improves hair cell function or survival, in specific cell types. The compositions and methods described herein relate to polynucleotides that stimulate transcription of a transgene in hair cells of the inner ear (e.g., cochlear hair cells and vestibular hair cells). The polynucleotides described herein may be operably linked to a therapeutic transgene, and may be administered to a patient to treat or prevent hearing loss (e.g., sensorineural hearing loss) and/or vestibular dysfunction (e.g., vertigo, dizziness, or imbalance).

In a first aspect, the invention provides a polynucleotide comprising a first region having at least 85% sequence identity (e.g., 85%, 90%, 95%, 96%, 97%, 98%, 99%, or more, sequence identity) to SEQ ID NO: 1 or a functional portion or derivative thereof including the sequence of SEQ ID NO: 3 and/or SEQ ID NO: 4, joined (e.g., operably linked) to a second region having at least 85% sequence identity (e.g., 85%, 90%, 95%, 96%, 97%, 98%, 99%, or more, sequence identity) to SEQ ID NO: 2 or a functional portion or derivative thereof including the sequence of SEQ ID NO: 8 and/or SEQ ID NO: 9, optionally containing a linker including one to one hundred nucleotides (e.g., 1-5, 1-10, 1-15, 1-20, 1-25, 1-30, 1-35, 1-40, 1-45, 1-50, 1-60, 1-70, 1-80, 1-90, 10-20, 10-30, 10-40, 10-50, 10-60, 10-70, 10-80, 10-90, 10-100, 20-30, 20-40, 20-50, 20-60, 20-70, 20-80, 20-90, or 20-100 nucleotides) between the first region and the second region.

In some embodiments, the first region comprises or consists of the sequence of SEQ ID NO: 1.

In some embodiments, the second region comprises or consists of the sequence of SEQ ID NO: 2.

In some embodiments, the polynucleotide comprises or consists of the sequence of SEQ ID NO: 13. In some embodiments, the polynucleotide comprises or consists of the sequence of SEQ ID NO: 15. In some embodiments, the polynucleotide comprises or consists of the sequence of SEQ ID NO: 16. In some embodiments, the polynucleotide comprises or consists of the sequence of SEQ ID NO: 30. In some embodiments, the polynucleotide comprises or consists of the sequence of SEQ ID NO: 31. In some embodiments, the polynucleotide comprises or consists of the sequence of SEQ ID NO: 36. In some embodiments, the polynucleotide comprises or consists of the sequence of SEQ ID NO: 37.

In another aspect, the invention provides a polynucleotide comprising a first region having at least 85% sequence identity (e.g., 85%, 90%, 95%, 96%, 97%, 98%, 99%, or more, sequence identity) to SEQ ID NO: 2 or a functional portion or derivative thereof including the sequence of SEQ ID NO: 8 and/or SEQ ID NO: 9, joined (e.g., operably linked) to a second region having at least 85% sequence identity (e.g., 85%, 90%, 95%, 96%, 97%, 98%, 99%, or more, sequence identity) to SEQ ID NO: 1 or a functional portion or derivative thereof including the sequence of SEQ ID NO: 3 and/or SEQ ID NO: 4, optionally containing a linker including one to one hundred nucleotides (e.g., 1-5, 1-10, 1-15, 1-20, 1-25, 1-30, 1-35, 1-40, 1-45, 1-50, 1-60, 1-70, 1-80, 1-90, 10-20, 10-30, 10-40, 10-50, 10-60, 10-70, 10-80, 10-90, 10-100, 20-30, 20-40, 20-50, 20-60, 20-70, 20-80, 20-90, or 20-100 nucleotides) between the first region and the second region.

In some embodiments, the first region comprises or consists of the sequence of SEQ ID NO: 2.

In some embodiments, the second region comprises or consists of the sequence of SEQ ID NO: 1.

In some embodiments, the polynucleotide comprises or consists of the sequence of SEQ ID NO: 14. In some embodiments, the polynucleotide comprises or consists of the sequence of SEQ ID NO: 35.

In another aspect, the invention provides a polynucleotide comprising a region having at least 85% sequence identity (e.g., 85%, 90%, 95%, 96%, 97%, 98%, 99%, or more, sequence identity) to SEQ ID NO: 1 or a functional portion or derivative thereof including the sequence of SEQ ID NO: 3 and/or SEQ ID NO: 4.

In some embodiments, the region comprises or consists of the sequence of SEQ ID NO: 1.

In another aspect, the invention provides a polynucleotide comprising a region having at least 85% sequence identity (e.g., 85%, 90%, 95%, 96%, 97%, 98%, 99%, or more, sequence identity) to SEQ ID NO: 2 or a functional portion or derivative thereof including the sequence of SEQ ID NO: 8 and/or SEQ ID NO: 9.

In some embodiments, the region comprises or consists of the sequence of SEQ ID NO: 2.

In some embodiments of any of the foregoing aspects, the functional portion of SEQ ID NO: 1 contains the sequence of SEQ ID NO: 3. In some embodiments of any of the foregoing aspects, the functional portion of SEQ ID NO: 1 contains the sequence of SEQ ID NO: 4. In some embodiments of any of the foregoing aspects, the functional portion of SEQ ID NO: 1 contains the sequence of SEQ ID NO: 3 and the sequence of SEQ ID NO: 4. In some embodiments of any of the foregoing aspects, the functional portion of SEQ ID NO: 1 contains the sequence of SEQ ID NO: 5. In some embodiments of any of the foregoing aspects, the functional portion of SEQ ID NO: 1 contains the sequence of SEQ ID NO: 6. In some embodiments of any of the foregoing aspects, the functional portion of SEQ ID NO: 1 contains the sequence of SEQ ID NO: 7. In some embodiments of any of the foregoing aspects, the functional portion of SEQ ID NO: 1 contains the sequence of SEQ ID NO: 27.

In some embodiments of any of the foregoing aspects, the functional portion of SEQ ID NO: 2 contains the sequence of SEQ ID NO: 8. In some embodiments of any of the foregoing aspects, the functional portion of SEQ ID NO: 2 contains the sequence of SEQ ID NO: 9. In some embodiments of any of the foregoing aspects, the functional portion of SEQ ID NO: 2 contains the sequence of SEQ ID NO: 8 and the sequence of SEQ ID NO: 9. In some embodiments of any of the foregoing aspects, the functional portion of SEQ ID NO: 2 contains the sequence of SEQ ID NO: 28. In some embodiments of any of the foregoing aspects, the functional portion of SEQ ID NO: 2 contains the sequence of SEQ ID NO: 29. In some embodiments of any of the foregoing aspects, the functional portion of SEQ ID NO: 2 contains the sequence of SEQ ID NO: 10. In some embodiments of any of the foregoing aspects, the functional portion of SEQ ID NO: 2 contains the sequence of SEQ ID NO: 11. In some embodiments of any of the foregoing aspects, the functional portion of SEQ ID NO: 2 contains the sequence of SEQ ID NO: 12. In some embodiments of any of the foregoing aspects, the functional portion of SEQ ID NO: 2 contains the sequence of SEQ ID NO: 32.

In another aspect, the invention provides a polynucleotide comprising a first region having at least 85% sequence identity (e.g., 85%, 90%, 95%, 96%, 97%, 98%, 99%, or more, sequence identity) to SEQ ID NO: 17 or a functional portion or derivative thereof including the sequence of SEQ ID NO: 19, joined (e.g., operably linked) to a second region having at least 85% sequence identity (e.g., 85%, 90%, 95%, 96%, 97%, 98%, 99%, or more, sequence identity) to SEQ ID NO: 18 or a functional portion or derivative thereof including the sequence of SEQ ID NO: 20 and/or SEQ ID NO: 21, optionally containing a linker including one to four hundred nucleotides (e.g., 1-5, 1-10, 1-15, 1-20, 1-25, 1-30, 1-35, 1-40, 1-45, 1-50, 1-60, 1-70, 1-80, 1-90, 1-100, 1-125, 1-150, 1-175, 1-200, 1-225, 1-250, 1-275, 1-300, 1-325, 1-350, 1-375, 1-400, 10-20, 10-30, 10-40, 10-50, 10-60, 10-70, 10-80, 10-90, 10-100, 20-30, 20-40, 20-50, 20-60, 20-70, 20-80, 20-90, 20-100, 30-100, 40-100, 50-100, 50-150, 50-200, 50-250, 50-300, 50-350, 50-400, 100-150, 100-200, 100-250, 100-300, 100-350, 100-400, 150-200, 150-250, 150-300, 150-350, 150-400, 200-250, 200-300, 200-350, 200-400, 250-300, 250-350, 250-400, 300-400, or 350-400 nucleotides) between the first region and the second region.

In some embodiments, the first region comprises or consists of the sequence of SEQ ID NO: 17.

In some embodiments, the second region comprises or consists of the sequence of SEQ ID NO: 18.

In some embodiments, the polynucleotide comprises or consists of the sequence of SEQ ID NO: 25.

In some embodiments, the polynucleotide comprises or consists of the sequence of SEQ ID NO: 26.

In another aspect, the invention provides a polynucleotide comprising a first region having at least 85% sequence identity (e.g., 85%, 90%, 95%, 96%, 97%, 98%, 99%, or more, sequence identity) to SEQ ID NO: 18 or a functional portion or derivative thereof including the sequence of SEQ ID NO: 20 and/or SEQ ID NO: 21, joined (e.g., operably linked) to a second region having at least 85% sequence identity (e.g., 85%, 90%, 95%, 96%, 97%, 98%, 99%, or more, sequence identity) to SEQ ID NO: 17 or a functional portion or derivative thereof including the sequence of SEQ ID NO: 19, optionally containing a linker including one to four hundred nucleotides (e.g., 1-5, 1-10, 1-15, 1-20, 1-25, 1-30, 1-35, 1-40, 1-45, 1-50, 1-60, 1-70, 1-80, 1-90, 1-100, 1-125, 1-150, 1-175, 1-200, 1-225, 1-250, 1-275, 1-300, 1-325, 1-350, 1-375, 1-400, 10-20, 10-30, 10-40, 10-50, 10-60, 10-70, 10-80, 10-90, 10-100, 20-30, 20-40, 20-50, 20-60, 20-70, 20-80, 20-90, 20-100, 30-100, 40-100, 50-100, 50-150, 50-200, 50-250, 50-300, 50-350, 50-400, 100-150, 100-200, 100-250, 100-300, 100-350, 100-400, 150-200, 150-250, 150-300, 150-350, 150-400, 200-250, 200-300, 200-350, 200-400, 250-300, 250-350, 250-400, 300-400, or 350-400 nucleotides) between the first region and the second region.

In some embodiments, the first region comprises or consists of the sequence of SEQ ID NO: 18.

In some embodiments, the second region comprises or consists of the sequence of SEQ ID NO: 17.

In another aspect, the invention provides a polynucleotide comprising a region having at least 85% sequence identity (e.g., 85%, 90%, 95%, 96%, 97%, 98%, 99%, or more, sequence identity) to SEQ ID NO: 17 or a functional portion or derivative thereof including the sequence of SEQ ID NO: 19.

In some embodiments, the region comprises or consists of the sequence of SEQ ID NO: 17.

In another aspect, the invention provides a polynucleotide comprising a region having at least 85% sequence identity (e.g., 85%, 90%, 95%, 96%, 97%, 98%, 99%, or more, sequence identity) to SEQ ID NO: 18 or a functional portion or derivative thereof including the sequence of SEQ ID NO: 20 and/or SEQ ID NO: 21.

In some embodiments, the region comprises or consists of the sequence of SEQ ID NO: 18.

In some embodiments of any of the foregoing aspects, the functional portion of SEQ ID NO: 17 contains the sequence of SEQ ID NO: 19.

In some embodiments of any of the foregoing aspects, the functional portion of SEQ ID NO: 18 contains the sequence of SEQ ID NO: 20. In some embodiments of any of the foregoing aspects, the functional portion of SEQ ID NO: 18 contains the sequence of SEQ ID NO: 21. In some embodiments of any of the foregoing aspects, the functional portion of SEQ ID NO: 18 contains the sequence of SEQ ID NO: 20 and the sequence of SEQ ID NO: 21. In some embodiments of any of the foregoing aspects, the functional portion of SEQ ID NO: 18 contains the sequence of SEQ ID NO: 22. In some embodiments of any of the foregoing aspects, the functional portion of SEQ ID NO: 18 contains the sequence of SEQ ID NO: 23. In some embodiments of any of the foregoing aspects, the functional portion of SEQ ID NO: 18 contains the sequence of SEQ ID NO: 24.

In another aspect, the invention provides a polynucleotide having at least 85% sequence identity (e.g., 85%, 90%, 95%, 96%, 97%, 98%, 99%, or more, sequence identity) to the nucleic acid sequence of any one of SEQ ID NOs: 27-35. In some embodiments, the polynucleotide has at least 85% sequence identity (e.g., 85%, 90%, 95%, 96%, 97%, 98%, 99%, or more, sequence identity) to the nucleic acid sequence of SEQ ID NO: 28. In some embodiments, the polynucleotide has at least 85% sequence identity (e.g., 85%, 90%, 95%, 96%, 97%, 98%, 99%, or more, sequence identity) to the nucleic acid sequence of SEQ ID NO: 32. In some embodiments, the polynucleotide has at least 85% sequence identity (e.g., 85%, 90%, 95%, 96%, 97%, 98%, 99%, or more, sequence identity) to the nucleic acid sequence of SEQ ID NO: 33. In some embodiments, the polynucleotide has at least 85% sequence identity (e.g., 85%, 90%, 95%, 96%, 97%, 98%, 99%, or more, sequence identity) to the nucleic acid sequence of SEQ ID NO: 34. In some embodiments, the polynucleotide comprises or consists of the sequence of SEQ ID NO: 28. In some embodiments, the polynucleotide comprises or consists of the sequence of SEQ ID NO: 32. In some embodiments, the polynucleotide the polynucleotide comprises or consists of the sequence of SEQ ID NO: 33. In some embodiments, the polynucleotide comprises or consists of the sequence of SEQ ID NO: 34.

In some embodiments of any of the foregoing aspects, the polynucleotide induces transgene expression when operably linked to a transgene and introduced into a hair cell.

In another aspect, the invention provides a nucleic acid vector containing a polynucleotide of the invention. In some embodiments, the polynucleotide is operably linked to a transgene. In some embodiments, the transgene comprises a nucleic acid sequence encoding a therapeutic protein. In some embodiments, the polynucleotide is capable of directing hair cell-specific expression of the therapeutic protein from the nucleic acid sequence in a mammalian hair cell. In some embodiments, the hair cell is a cochlear hair cell. In some embodiments, the cochlear hair cell is an inner hair cell. In some embodiments, the cochlear hair cell is an outer hair cell. In some embodiments, the hair cell is a vestibular hair cell.

In some embodiments, the therapeutic protein is selected from the group containing ACTG1, FSCN2, RDX, POU4F3, TRIOBP, TPRN, XIRP2, ATOH1, GFI1, CHRNA9, CIB3, CDH23, PCDH15, KNCN, DFNB59, OTOF, MKRN2OS, LHX3, TMC1, MYO15, MYO7A, MYO6, MYO3A, MYO3B, GRXCR1, PTPRQ, LCE6A, LOXHD1, ART1, ATP2B2, CIB2, CACNA2D4, CABP2, EPS8, EPS8L2, ESPN, ESPNL, PRPH2, STRC, SLC8A2, ZCCHC12, LRTOMT2, LRTOMT1, USH1C, ELFN1, TTC24, DYTN, KCP, CCER2, LRTM2, KCNA10, NTF3, CLRN1, CLRN2, SKOR1, TCTEX1 D1, FCRLB, SLC17A8, GRXCR2, BDNF, SERPINE3, NHLH1, HSP70, HSP90, ATF6, PERK, IRE1, and BIP.

In some embodiments, the nucleic acid vector is a plasmid, cosmid, artificial chromosome, or viral vector. In some embodiments, the nucleic acid vector is a viral vector selected from the group consisting of an adeno-associated virus (AAV), an adenovirus, and a lentivirus. In some embodiments, the viral vector is an AAV vector. In some embodiments, the serotype of the AAV vector is selected from the group containing AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, and PHP.S. In some embodiments, the serotype of the AAV vector is AAV1. In some embodiments, the serotype of the AAV vector is AAV9. In some embodiments, the serotype of the AAV vector is AAV6. In some embodiments, the serotype of the AAV vector is Anc80. In some embodiments, the serotype of the AAV vector is Anc80L65. In some embodiments, the serotype of the AAV vector is DJ/9. In some embodiments, the serotype of the AAV vector is 7m8. In some embodiments, the serotype of the AAV vector is AAV2. In some embodiments, the serotype of the AAV vector is AAV2quad(Y-F). In some embodiments, the serotype of the AAV vector is PHP.B. In some embodiments, the serotype of the AAV vector is AAV8.

In another aspect, the invention provides a composition containing a nucleic acid vector of the invention. In some embodiments, the composition further includes a pharmaceutically acceptable excipient.

In another aspect, the invention provides a method of increasing expression of a therapeutic protein in a mammalian hair cell by contacting the mammalian hair cell with a nucleic acid vector of the invention or a composition of the invention. In some embodiments, expression of the therapeutic protein is specifically increased in hair cells.

In some embodiments, the mammalian hair cell is a human hair cell.

In some embodiments, the mammalian hair cell is a cochlear hair cell. In some embodiments, the cochlear hair cell is an inner hair cell. In some embodiments, the cochlear hair cell is an outer hair cell.

In some embodiments, the mammalian hair cell is a vestibular hair cell.

In some embodiments, expression of the therapeutic protein is not substantially increased in inner ear cells that are not hair cells.

In another aspect, the invention provides a method of treating a subject having or at risk of developing hearing loss (e.g., sensorineural hearing loss) by administering to the subject an effective amount of a nucleic acid vector of the invention or a composition of the invention.

In some embodiments, the hearing loss is genetic hearing loss. In some embodiments, the genetic hearing loss is autosomal dominant hearing loss, autosomal recessive hearing loss, or X-linked hearing loss.

In some embodiments, the hearing loss is acquired hearing loss. In some embodiments, the acquired hearing loss is noise-induced hearing loss, age-related hearing loss, disease or infection-related hearing loss, head trauma-related hearing loss, or ototoxic drug-induced hearing loss. In some embodiments, the acquired hearing loss is age-related hearing loss. In some embodiments, the hearing loss is noise-induced hearing loss. In some embodiments, the hearing loss is ototoxic drug-induced hearing loss.

In another aspect, the invention provides a method of treating a subject having or at risk of developing vestibular dysfunction by administering to the subject an effective amount of a nucleic acid vector of the invention or a composition of the invention. In some embodiments, the vestibular dysfunction is vertigo, dizziness, or imbalance (e.g., a balance disorder).

In another aspect, the invention provides a method of promoting hair cell regeneration in a subject in need thereof by administering to the subject an effective amount of a nucleic acid vector of the invention or a composition of the invention. In some embodiments, the hair cell is a cochlear hair cell. In some embodiments, the hair cell is a vestibular hair cell.

In another aspect, the invention provides a method of preventing or reducing ototoxic drug-induced hair cell damage or death by administering to the subject an effective amount of a nucleic acid vector of the invention or a composition of the invention. In some embodiments, the ototoxic drug is selected from the group including aminoglycosides (e.g., gentamycin, neomycin, streptomycin, tobramycin, kanamycin, vancomycin, and amikacin), antineoplastic drugs (e.g., platinum-containing chemotherapeutic agents, such as cisplatin, carboplatin, and oxaliplatin), ethacrynic acid, furosemide, salicylates (e.g., aspirin, particularly at high doses), and quinine. In some embodiments, the hair cell is a cochlear hair cell. In some embodiments, the hair cell is a vestibular hair cell.

In another aspect, the invention provides a method of treating a subject having tinnitus by administering to the subject an effective amount of a nucleic acid vector of the invention or a composition of the invention.

In some embodiments of any of the foregoing aspects, the hearing loss, vestibular dysfunction, or tinnitus is associated with loss of hair cells (e.g., cochlear and/or vestibular hair cells).

In another aspect, the invention provides a method of preventing or reducing hair cell damage or death in a subject in need thereof by administering to the subject an effective amount of a nucleic acid vector of the invention or a composition of the invention. In some embodiments, the hair cell is a cochlear hair cell. In some embodiments, the hair cell is a vestibular hair cell.

In another aspect, the invention provides a method of increasing hair cell survival in a subject in need thereof by administering to the subject an effective amount of a nucleic acid vector of the invention or a composition of the invention. In some embodiments, the hair cell is a cochlear hair cell. In some embodiments, the hair cell is a vestibular hair cell.

In some embodiments of any of the foregoing aspects, the hair cell is a cochlear hair cell. In some embodiments of any of the foregoing aspects, the cochlear hair cell is an inner hair cell. In some embodiments of any of the foregoing aspects, the cochlear hair cell is an outer hair cell. In some embodiments of any of the foregoing aspects, the mammalian hair cell is a vestibular hair cell.

In some embodiments of any of the foregoing aspects, the method further includes the step of evaluating the hearing of the subject prior to administering the nucleic acid vector or composition (e.g., evaluating hearing using standard tests, such as audiometry, auditory brainstem response (ABR), electrocochleography (ECOG), or otoacoustic emissions).

In some embodiments of any of the foregoing aspects, the method further includes the step of evaluating the hearing of the subject after administering the nucleic acid vector or composition (e.g., evaluating hearing using standard tests, such as audiometry, ABR, ECOG, or otoacoustic emissions).

In some embodiments of any of the foregoing aspects, the method further includes the step of evaluating the vestibular function of the subject prior to administering the nucleic acid vector or composition (e.g., evaluating vestibular function using standard tests, such as electronystagmogram (ENG) or videonystagmogram (VNG), posturography, rotary-chair testing, ECOG, vestibular evoked myogenic potentials (VEMP), or specialized clinical balance tests).

In some embodiments of any of the foregoing aspects, the method further includes the step of evaluating the vestibular function of the subject prior to administering the nucleic acid vector or composition (e.g., evaluating vestibular function using standard tests, such as ENG or VNG, posturography, rotary-chair testing, ECOG, VEMP, or specialized clinical balance tests).

In some embodiments of any of the foregoing aspects, the nucleic acid vector or composition is locally administered (e.g., administered to the inner ear, e.g., into the perilymph or endolymph, such as through the oval window, round window, or horizontal canal).

In some embodiments of any of the foregoing aspects, the nucleic acid vector or composition is administered in an amount sufficient to prevent or reduce hearing loss, prevent or reduce vestibular dysfunction, prevent or reduce tinnitus, delay the development of hearing loss, delay the development of vestibular dysfunction, slow the progression of hearing loss, slow the progression of vestibular dysfunction, improve hearing, improve vestibular function, improve hair cell function, prevent or reduce hair cell damage, prevent or reduce hair cell death, or increase hair cell numbers.

In some embodiments of any of the foregoing aspects, the subject is a human.

In another aspect, the invention provides a kit containing a nucleic acid vector of the invention or a composition of the invention.

Definitions

As used herein, the term "about" refers to a value that is within 10% above or below the value being described.

As used herein, "administration" refers to providing or giving a subject a therapeutic agent (e.g., a nucleic acid vector containing a Myosin 15 (Myo15) promoter operably linked to a transgene), by any effective route. Exemplary routes of administration are described herein below.

As used herein, the term "cell type" refers to a group of cells sharing a phenotype that is statistically separable based on gene expression data. For instance, cells of a common cell type may share similar structural and/or functional characteristics, such as similar gene activation patterns and antigen presentation profiles. Cells of a common cell type may include those that are isolated from a common tissue (e.g., epithelial tissue, neural tissue, connective tissue, or muscle tissue) and/or those that are isolated from a common organ, tissue system, blood vessel, or other structure and/or region in an organism.

As used herein, the term "cochlear hair cell" refers to group of specialized cells in the inner ear that are involved in sensing sound. There are two types of cochlear hair cells: inner hair cells and outer hair cells. Damage to cochlear hair cells and genetic mutations that disrupt cochlear hair cell function are implicated in hearing loss and deafness.

As used herein, the terms "conservative mutation," "conservative substitution," and "conservative amino acid substitution" refer to a substitution of one or more amino acids for one or more different amino acids that exhibit similar physicochemical properties, such as polarity, electrostatic charge, and steric volume. These properties are summarized for each of the twenty naturally-occurring amino acids in table 1 below.

TABLE 1

Representative physicochemical properties of naturally-occurring amino acids

| Amino Acid | 3 Letter Code | 1 Letter Code | Side-chain Polarity | Electrostatic character at physiological pH (7.4) | Steric Volume[†] |
|---|---|---|---|---|---|
| Alanine | Ala | A | nonpolar | neutral | small |
| Arginine | Arg | R | polar | cationic | large |
| Asparagine | Asn | N | polar | neutral | intermediate |
| Aspartic acid | Asp | D | polar | anionic | intermediate |
| Cysteine | Cys | C | nonpolar | neutral | intermediate |
| Glutamic acid | Glu | E | polar | anionic | intermediate |
| Glutamine | Gln | Q | polar | neutral | intermediate |
| Glycine | Gly | G | nonpolar | neutral | small |
| Histidine | His | H | polar | Both neutral and cationic forms in equilibrium at pH 7.4 | large |
| Isoleucine | Ile | I | nonpolar | neutral | large |
| Leucine | Leu | L | nonpolar | neutral | large |
| Lysine | Lys | K | polar | cationic | large |
| Methionine | Met | M | nonpolar | neutral | large |
| Phenylalanine | Phe | F | nonpolar | neutral | large |
| Proline | Pro | P | non-polar | neutral | intermediate |
| Serine | Ser | S | polar | neutral | small |
| Threonine | Thr | T | polar | neutral | intermediate |
| Tryptophan | Trp | W | nonpolar | neutral | bulky |
| Tyrosine | Tyr | Y | polar | neutral | large |
| Valine | Val | V | nonpolar | neutral | intermediate |

[†]based on volume in $Å^3$: 50-100 is small, 100-150 is intermediate, 150-200 is large, and >200 is bulky From this table it is appreciated that the conservative amino acid families include (i) G, A, V, L and I; (ii) D and E; (iii) C, S and T; (iv) H, K and R; (v) N and Q; and (vi) F, Y and W. A conservative mutation or substitution is therefore one that substitutes one amino acid for a member of the same amino acid family (e.g., a substitution of Ser for Thr or Lys for Arg).

As used herein, the terms "effective amount," "therapeutically effective amount," and a "sufficient amount" of a composition, vector construct, or viral vector described herein refer to a quantity sufficient to, when administered to the subject in need thereof, including a mammal, for example a human, effect beneficial or desired results, including clinical results, and, as such, an "effective amount" or synonym thereto depends upon the context in which it is being applied. For example, in the context of treating sensorineural hearing loss or vestibular dysfunction, it is an amount of the composition, vector construct, or viral vector sufficient to achieve a treatment response as compared to the response obtained without administration of the composition, vector construct, or viral vector. The amount of a given composition described herein that will correspond to such an amount will vary depending upon various factors, such as the given agent, the pharmaceutical formulation, the route of administration, the type of disease or disorder, the identity of the subject (e.g. age, sex, weight) or host being treated, and the like, but can nevertheless be routinely determined by one skilled in the art. Also, as used herein, a "therapeutically effective amount" of a composition, vector construct, or viral vector of the present disclosure is an amount which results in a beneficial or desired result in a subject as compared to a control. Note that when a combination of active ingredients is administered, the effective amount of the combination may or may not include amounts of each ingredient that would have been effective if administered individually. As defined herein, a therapeutically effective amount of a composition, vector construct, or viral vector of the present disclosure may be readily determined by one of ordinary skill by routine methods known in the art. Dosage regimen may be adjusted to provide the optimum therapeutic response.

As used herein, the term "endogenous" describes a molecule (e.g., a polypeptide, nucleic acid, or cofactor) that is found naturally in a particular organism (e.g., a human) or in a particular location within an organism (e.g., an organ, a tissue, or a cell, such as a human cell, e.g., a human hair cell).

As used herein, the term "express" refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

As used herein, the term "exogenous" describes a molecule (e.g., a polypeptide, nucleic acid, or cofactor) that is not found naturally in a particular organism (e.g., a human) or in a particular location within an organism (e.g., an organ, a tissue, or a cell, such as a human cell, e.g., a human hair cell).

Exogenous materials include those that are provided from an external source to an organism or to cultured matter extracted there from.

As used herein, the term "hair cell-specific expression" refers to production of an RNA transcript or polypeptide primarily within hair cells (e.g., cochlear hair cells and/or vestibular hair cells) as compared to other cell types of the inner ear (e.g., spiral ganglion neurons, glia, or other inner ear cell types). Hair cell-specific expression of a transgene can be confirmed by comparing transgene expression (e.g., RNA or protein expression) between various cell types of the inner ear (e.g., hair cells vs. non-hair cells) using any standard technique (e.g., quantitative RT PCR, immunohistochemistry, Western Blot analysis, or measurement of the fluorescence of a reporter (e.g., GFP) operably linked to a promoter). A hair cell-specific promoter induces expression (e.g., RNA or protein expression) of a transgene to which it is operably linked that is at least 50% greater (e.g., 50%, 75%, 100%, 125%, 150%, 175%, 200% greater or more) in hair cells compared to at least 3 (e.g., 3, 4, 5, 6, 7, 8, 9, 10, or more) of the following inner ear cell types: Border cells, inner phalangeal cells, inner pillar cells, outer pillar cells, first row Deiter cells, second row Deiter cells, third row Deiter cells, Hensen's cells, Claudius cells, inner sulcus cells, outer sulcus cells, spiral prominence cells, root cells, interdental cells, basal cells of the stria vascularis, intermediate cells of the stria vascularis, marginal cells of the stria vascularis, spiral ganglion neurons, Schwann cells.

As used herein, the terms "increasing" and "decreasing" refer to modulating resulting in, respectively, greater or lesser amounts, of function, expression, or activity of a metric relative to a reference. For example, subsequent to administration of a composition in a method described herein, the amount of a marker of a metric (e.g., transgene expression) as described herein may be increased or decreased in a subject by at least 5%, 10%, 15%, 20%, 25%, 30%, 35%, 40%, 45%, 50%, 55%, 60%, 65%, 70%, 75%, 80%, 85%, 90%, 95% or 98% or more relative to the amount of the marker prior to administration. Generally, the metric is measured subsequent to administration at a time that the administration has had the recited effect, e.g., at least one week, one month, 3 months, or 6 months, after a treatment regimen has begun.

As used herein, the term "intron" refers to a region within the coding region of a gene, the nucleotide sequence of which is not translated into the amino acid sequence of the corresponding protein. The term intron also refers to the corresponding region of the RNA transcribed from a gene. Introns are transcribed into pre-mRNA, but are removed during processing, and are not included in the mature mRNA.

As used herein, the term "linker" refers to a series of nucleotides that connects two different regions of a polynucleotide. A linker does not disrupt the function of the two regions of the polynucleotide that it connects.

As used herein, "locally" or "local administration" means administration at a particular site of the body intended for a local effect and not a systemic effect. Examples of local administration are epicutaneous, inhalational, intra-articular, intrathecal, intravaginal, intravitreal, intrauterine, intra-lesional administration, lymph node administration, intratumoral administration, administration to the inner ear, and administration to a mucous membrane of the subject, wherein the administration is intended to have a local and not a systemic effect.

As used herein, the term "operably linked" refers to a first molecule that can be joined to a second molecule, wherein the molecules are so arranged that the first molecule affects the function of the second molecule. The term "operably linked" includes the juxtaposition of two or more components (e.g., a promoter and another sequence element) such that both components function normally and allow for the possibility that at least one of the components can mediate a function that is exerted upon at least one of the other components. The two molecules may or may not be part of a single contiguous molecule and may or may not be adjacent. For example, a promoter is operably linked to a transcribable polynucleotide molecule if the promoter modulates transcription of the transcribable polynucleotide molecule of interest in a cell. In additional embodiments, two portions of a transcription regulatory element are operably linked to one another if they are joined such that the transcription-activating functionality of one portion is not adversely affected by the presence of the other portion. Two transcription regulatory elements may be operably linked to one another by way of a linker nucleic acid (e.g., an intervening non-coding nucleic acid) or may be operably linked to one another with no intervening nucleotides present.

As used herein, the term "plasmid" refers to a to an extrachromosomal circular double stranded DNA molecule into which additional DNA segments may be ligated. A plasmid is a type of vector, a nucleic acid molecule capable of transporting another nucleic acid to which it has been linked. Certain plasmids are capable of autonomous replication in a host cell into which they are introduced (e.g., bacterial plasmids having a bacterial origin of replication and episomal mammalian plasmids). Other vectors (e.g., non-episomal mammalian vectors) can be integrated into the genome of a host cell upon introduction into the host cell, and thereby are replicated along with the host genome. Certain plasmids are capable of directing the expression of genes to which they are operably linked.

As used herein, the terms "nucleic acid" and "polynucleotide," used interchangeably herein, refer to a polymeric form of nucleosides in any length. Typically, a polynucleotide is composed of nucleosides that are naturally found in DNA or RNA (e.g., adenosine, thymidine, guanosine, cytidine, uridine, deoxyadenosine, deoxythymidine, deoxyguanosine, and deoxycytidine) joined by phosphodiester bonds. The term encompasses molecules comprising nucleosides or nucleoside analogs containing chemically or biologically modified bases, modified backbones, etc., whether or not found in naturally occurring nucleic acids, and such molecules may be preferred for certain applications. Where this application refers to a polynucleotide it is understood that both DNA, RNA, and in each case both single- and double-stranded forms (and complements of each single-stranded molecule) are provided. "Polynucleotide sequence" as used herein can refer to the polynucleotide material itself and/or to the sequence information (i.e., the succession of letters used as abbreviations for bases) that biochemically characterizes a specific nucleic acid. A polynucleotide sequence presented herein is presented in a 5' to 3' direction unless otherwise indicated.

As used herein, the terms "complementarity" or "complementary" of nucleic acids means that a nucleotide sequence in one strand of nucleic acid, due to orientation of its nucleobase groups, forms hydrogen bonds with another sequence on an opposing nucleic acid strand. The complementary bases in DNA are typically A with T and C with G. In RNA, they are typically C with G and U with A.

Complementarity can be perfect or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm (melting temperature) of hybridized strands, or by empirical determination of Tm by using routine methods. Tm includes the temperature at which a population of hybridization complexes formed between two nucleic acid strands are 50% denatured (i.e., a population of double-stranded nucleic acid molecules becomes half dissociated into single strands). At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+ 0.41(% G+C), although other known Tm computations take into account nucleic acid structural characteristics.

As used herein, the term "promoter" refers to a recognition site on DNA that is bound by an RNA polymerase. The polymerase drives transcription of the transgene.

"Percent (%) sequence identity" with respect to a reference polynucleotide or polypeptide sequence is defined as the percentage of nucleic acids or amino acids in a candidate sequence that are identical to the nucleic acids or amino acids in the reference polynucleotide or polypeptide sequence, after aligning the sequences and introducing gaps, if necessary, to achieve the maximum percent sequence identity. Alignment for purposes of determining percent nucleic acid or amino acid sequence identity can be achieved in various ways that are within the capabilities of one of skill in the art, for example, using publicly available computer software such as BLAST, BLAST-2, or Megalign software. Those skilled in the art can determine appropriate parameters for aligning sequences, including any algorithms needed to achieve maximal alignment over the full length of the sequences being compared. For example, percent sequence identity values may be generated using the sequence comparison computer program BLAST. As an illustration, the percent sequence identity of a given nucleic acid or amino acid sequence, A, to, with, or against a given nucleic acid or amino acid sequence, B, (which can alternatively be phrased as a given nucleic acid or amino acid sequence, A that has a certain percent sequence identity to, with, or against a given nucleic acid or amino acid sequence, B) is calculated as follows:

100 multiplied by (the fraction X/Y)

where X is the number of nucleotides or amino acids scored as identical matches by a sequence alignment program (e.g., BLAST) in that program's alignment of A and B, and where Y is the total number of nucleic acids in B. It will be appreciated that where the length of nucleic acid or amino acid sequence A is not equal to the length of nucleic acid or amino acid sequence B, the percent sequence identity of A to B will not equal the percent sequence identity of B to A.

The term "derivative" as used herein refers to a nucleic acid, peptide, or protein or a variant or analog thereof comprising one or more mutations and/or chemical modifications as compared to a corresponding full-length wild-type nucleic acid, peptide, or protein. Non-limiting examples of chemical modifications involving nucleic acids include, for example, modifications to the base moiety, sugar moiety, phosphate moiety, phosphate-sugar backbone, or a combination thereof.

As used herein, the term "pharmaceutical composition" refers to a mixture containing a therapeutic agent, optionally in combination with one or more pharmaceutically acceptable excipients, diluents, and/or carriers, to be administered to a subject, such as a mammal, e.g., a human, in order to prevent, treat or control a particular disease or condition affecting or that may affect the subject.

As used herein, the term "pharmaceutically acceptable" refers to those compounds, materials, compositions and/or dosage forms, which are suitable for contact with the tissues of a subject, such as a mammal (e.g., a human) without excessive toxicity, irritation, allergic response and other problem complications commensurate with a reasonable benefit/risk ratio. Preferably, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) isolated from a subject.

As used herein, the term "transcription regulatory element" refers to a nucleic acid that controls, at least in part, the transcription of a gene of interest. Transcription regulatory elements may include promoters, enhancers, and other nucleic acids (e.g., polyadenylation signals) that control or help to control gene transcription. Examples of transcription regulatory elements are described, for example, in Lorence, Recombinant Gene Expression: Reviews and Protocols (Humana Press, New York, NY, 2012).

As used herein, the term "transfection" refers to any of a wide variety of techniques commonly used for the introduction of exogenous DNA into a prokaryotic or eukaryotic host cell, e.g., electroporation, lipofection, calcium phosphate precipitation, DEAE-dextran transfection, Nucleofection, squeeze-poration, sonoporation, optical transfection, magnetofection, impalefection and the like.

As used herein, the terms "subject" and "patient" refer to an animal (e.g., a mammal, such as a human), veterinary animals (e.g., cats, dogs, cows, horses, sheep, pigs, etc.) and experimental animal models of diseases (e.g., mice, rats). A subject to be treated according to the methods described herein may be one who has been diagnosed with hearing loss (e.g., sensorineural hearing loss) or vestibular dysfunction (e.g., dizziness, vertigo, or imbalance) or one at risk of developing these conditions. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

As used herein, the terms "transduction" and "transduce" refer to a method of introducing a vector construct or a part thereof into a cell. Wherein the vector construct is contained in a viral vector such as for example an AAV vector, transduction refers to viral infection of the cell and subsequent transfer and integration of the vector construct or part thereof into the cell genome.

As used herein, "treatment" and "treating" of a state, disorder or condition can include: (1) preventing, delaying, or reducing the incidence and/or likelihood of the appearance of at least one clinical or sub-clinical symptom of the state, disorder or condition developing in a subject that may be afflicted with or predisposed to the state, disorder or condition, but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof; or (3) relieving the disease, i.e., causing regression of the state, disorder or condition or at least one of its clinical or sub-clinical symptoms. The benefit to a subject to be treated is either statistically significant or at least perceptible to the patient or to the physician.

As used herein, the term "vector" includes a nucleic acid vector, e.g., a DNA vector, such as a plasmid, cosmid, or artificial chromosome, an RNA vector, a virus, or any other suitable replicon (e.g., viral vector). A variety of vectors have been developed for the delivery of polynucleotides encoding exogenous proteins into a prokaryotic or eukaryotic cell. Examples of such expression vectors are described in, e.g., Gellissen, Production of Recombinant Proteins: Novel Microbial and Eukaryotic Expression Systems (John Wiley & Sons, Marblehead, M A, 2006). Expression vectors suitable for use with the compositions and methods described herein contain a polynucleotide sequence as well as, e.g., additional sequence elements used for the expression of proteins and/or the integration of these polynucleotide sequences into the genome of a mammalian cell. Certain vectors that can be used for the expression of transgene as described herein include vectors that contain regulatory sequences, such as promoter and enhancer regions, which direct gene transcription. Other useful vectors for expression of a transgene contain polynucleotide sequences that enhance the rate of translation of the transgene or improve the stability or nuclear export of the mRNA that results from gene transcription. These sequence elements include, e.g., 5' and 3' untranslated regions and a polyadenylation signal site in order to direct efficient transcription of the gene carried on the expression vector. The expression vectors suitable for use with the compositions and methods described herein may also contain a polynucleotide encoding a marker for selection of cells that contain such a vector. Examples of a suitable marker include genes that encode resistance to antibiotics, such as ampicillin, chloramphenicol, kanamycin, or nourseothricin.

As used herein, the term "vestibular hair cell" refers to group of specialized cells in the inner ear that are involved in sensing movement and contribute to the sense of balance and spatial orientation. Vestibular hair cells are located in the semicircular canals and otoliths of the inner ear. Damage to vestibular hair cells and genetic mutations that disrupt vestibular hair cell function are implicated in vestibular dysfunction such as vertigo and imbalance disorders.

As used herein, the term "wild-type" refers to a genotype with the highest frequency for a particular gene in a given organism.

BRIEF DESCRIPTION OF THE DRAWINGS

FIGS. 3A-3B are series of fluorescent images of mouse cochlea transduced with an AAV 2/9 viral vector expressing GFP under the control of the murine Myo15 1 kb promoter (SEQ ID NO: 15, FIG. 3A) or the Myo15 mini intron promoter (SEQ ID NO: 16, FIG. 3B). As shown in FIGS. 3A-3B, both the murine Myo15 1 kb (SEQ ID NO: 15) and murine Myo15 mini intron (SEQ ID NO: 16) promoters induced expression of GFP specifically in hair cells.

FIGS. 4A-4G are a series of images of mouse cochlea showing the specificity of murine and human Myo15 promoters. Neonatal mouse cochlear explants were treated in culture with AAV1 vectors encoding GFP under control of either the 0.6 kb human Myo15 promoter (SEQ ID NO: 26; FIG. 4A), 1.2 kb human Myo15 promoter (SEQ ID NO: 25; FIG. 4B) or the 1 kb mouse Myo15 promoter (SEQ ID NO: 15; FIG. 4C) (scale bars=100 μm). GFP signal, as detected with anti-GFP antibody, is shown. In a separate experiment, AAV1-1.2 kb human Myo15-GFP or AAV1-1 kb murine Myo15-GFP was delivered to adult mouse cochlea via round window injection. Whole mount images (FIGS. 4D-4E) or sections (FIGS. 4F-4G) show hair cell-specific signal in the apex, middle, and base of the cochlea, as detected with anti-GFP antibody. Arrows in FIG. 4F point to GFP-labeled cochlear hair cells. As shown in FIGS. 4F and 4G, expression with both the 1.2 kb human Myo15 promoter and 1 kb murine Myo15 promoter was restricted primarily to inner hair cells.

FIG. 5A is a confocal image of the cochlea from a non-human primate that received a local injection of AAV1-CMV-GFP through the round window membrane. Tissue was harvested 28 days after injection. Native GFP fluorescence is shown. GFP expression was detected in a broad array of cell types throughout the organ.

FIG. 5B is a confocal image of the cochlea from a non-human primate that was injected with AAV1-Myo15 (SEQ ID NO: 13)-GFP and processed in the same way as the cochlea in FIG. 5A. GFP expression was restricted to hair cells. FIG. 5C is a magnified view of the hair cells in the box region shown in FIG. 5B.

FIG. 6 is a graph showing that the 1.6 kb Myo15 promoter (SEQ ID NO: 13) enhanced biological efficacy of an AAV-mouse TMC1 vector in Tmc1 knockout (KO) mice compared to the ubiquitous CMV promoter. Tmc1 KO mice were injected at postnatal day 2 (P2) and auditory brainstem response (ABR) was assessed at the indicated ages. ABR thresholds were plotted as a function of stimulus frequency for naïve homozygous (light gray line with open circles) and heterozygous (dark gray line through black circles) Tmc1 KO mice as well as homozygous Tmc1 KO mice injected with AAV-CMV-mouse TMC1 (CMV_mTmc1; dark gray line with open circles) or AAV-Myo15 (SEQ ID NO:13)-mouse TMC1 (PdBx_mTmc1; P23, light gray line through light gray circles; P28, dark gray line with filled circles). Restoration of ABR thresholds was greatly improved in homozygous Tmc1 KO mice injected with AAV-Myo15-mouse TMC1 compared to AAV-CMV-mouse TMC1.

DETAILED DESCRIPTION

Figure 1A:
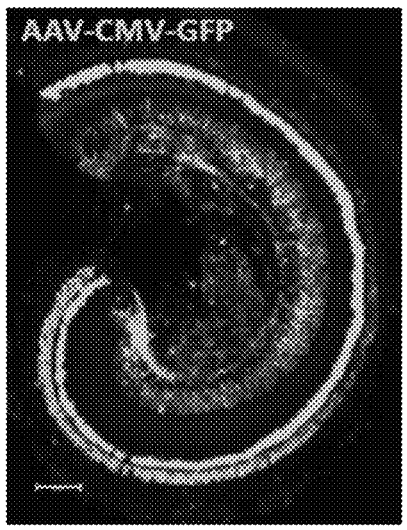
FIGS. 1A-1B are a series of fluorescent images of mouse cochlea transduced with either an adeno-associated virus (AAV) vector expressing GFP under the control of the cytomegalovirus (CMV) promoter (FIG. 1A) or an AAV vector expressing GFP under control of the murine Myo15 promoter (SEQ ID NO: 13, FIG. 1B). AAV-Myo15-GFP virus was infused via posterior semi-circular canal to 6-8-week-old C57Bl/6J male mice. Mice recovered from surgery and were euthanized and perfused with 10% normal buffered formalin 10 days later. The inner ear temporal bone was harvested and decalcified in 8% EDTA for 3 days. The cochlea was dissected from the de-calcified temporal bone and mounted on a slide for confocal imaging. Using a ubiquitous promoter, AAV-CMV-GFP induced GFP expression in many cell types within the cochlea including inner hair cells, outer hair cells, spiral ganglion neurons, mesenchymal cells, and glia (FIG. 1A). Using the hair cell-specific promoter, AAV-Myo15-GFP induced expression exclusively in the inner and outer hair cells (FIG. 1B).

Described herein are compositions and methods for inducing transgene expression specifically in hair cells (e.g., cochlear and/or vestibular hair cells). The invention features polynucleotides containing regions of the Myosin 15 (Myo15) promoter that are capable of expressing a transgene specifically in cochlear hair cells. The invention also features nucleic acid vectors containing these promoters operably linked to polynucleotides encoding polypeptides. The compositions and methods described herein can be used to express polynucleotides encoding hair cell proteins specifically in cochlear and vestibular hair cells, and, therefore, the compositions described herein can be administered to a subject (such as a mammalian subject, for instance, a human) to treat disorders caused by dysfunction of hair cells, such as hearing loss or vestibular dysfunction.

Hair Cells

Hair cells are sensory cells of the auditory and vestibular systems that reside in the inner ear. Cochlear hair cells are the sensory cells of the auditory system and are made up of two main cell types: inner hair cells, which are responsible for sensing sound, and outer hair cells, which are thought to amplify low-level sound. Vestibular hair cells are located in the semicircular canals and otolith organs of the inner ear and are involved in the sensation of movement that contributes to the sense of balance and spatial orientation. Hair cells are named for the stereocilia that protrude from the apical surface of the cell, forming a hair cell bundle. Deflection of the stereocilia (e.g., by sound waves in cochlear hair cells, or by rotation or linear acceleration in vestibular hair cells) leads to the opening of mechanically gated ion channels, which allows hair cells to release neurotransmitters to activate nerves, thereby converting mechanical sound or motion signals into electrical signals that can be transmitted to the brain. Cochlear hair cells are essential for normal hearing, and damage to cochlear hair cells and genetic mutations that disrupt cochlear hair cell function are implicated in hearing loss and deafness. Damage to vestibular hair cells and genetic mutations that disrupt vestibular hair cell function are implicated in vestibular dysfunction, such as loss of balance and vertigo (e.g., dizziness). Gene therapy has recently emerged as an attractive therapeutic approach for treating hearing loss and vestibular dysfunction; however, the field lacks methods for specifically targeting the nucleic acid vectors used in gene therapy to hair cells.

Myosin 15

Myo15 is an unconventional actin-based molecular motor that regulates stereocilia development. Mice carrying mutations in Myo15 have been found to have short stereocilia and profound hearing loss and vestibular dysfunction, and mutations in the human ortholog, Myo15A, cause non-syndromic autosomal recessive deafness, DFNB3. Myo15 has been observed to localize to stereocilia and is indispensable for stereocilia development and maintenance. The pattern of localization indicates that Myo15 may be specifically expressed in hair cells. However, the Myo15 promoter has not previously been isolated and characterized. We identified evolutionarily conserved blocks in orthologous genomic sequences that may constitute regulatory elements of the promoter and found that they are located more than 7200 base pairs (bp) upstream of the translation start site. This genomic region is too large to be used in conjunction with adeno-associated virus (AAV) vectors to deliver transgenes of interest for gene therapy, which have a maximum packaging capacity of 4.7 kb.

The present invention is based, in part, on the discovery of regions upstream of the Myo15 translation start site that can be used to promote expression of a transgene specifically in hair cells (e.g., cochlear and/or vestibular hair cells). The compositions and methods described herein can, thus, be used to express a gene of interest in hair cells (e.g., a gene implicated in hair cell development, function, cell fate specification, regeneration, survival, or maintenance, or a gene known to be disrupted, e.g., mutated, in subjects with hearing loss or vestibular dysfunction) to treat subjects having or at risk of developing hearing loss (e.g., sensorineural hearing loss) and/or vestibular dysfunction (e.g., vertigo, dizziness, or loss of balance).

Murine Myosin 15 Promoters

The polynucleotides of the compositions and methods described herein include nucleic acid sequences from regions of the murine Myo15 locus that are capable of expressing a transgene specifically in hair cells, or variants thereof, such as a nucleic acid sequences that have at least 85% sequence identity (e.g., 85%, 90%, 95%, 96%, 97%, 98%, 99%, or more, sequence identity) to regions of the murine Myo15 locus that are capable of expressing a transgene specifically in hair cells. These regions include nucleic acid sequences immediately preceding the murine Myo15 translation start site and an upstream regulatory element that is located over 5 kb from murine the Myo15 translation start site. The polynucleotides of the compositions and methods described herein can optionally include a linker operably linking the regions of the murine Myo15 locus that are capable of expressing a transgene specifically in hair cells, or the regions of the murine Myo15 locus can be joined directly without an intervening linker.

In some embodiments, the polynucleotides described herein contain a first region (an upstream regulatory element) having at least 85% sequence identity (e.g., 85%, 90%, 95%, 96%, 97%, 98%, 99%, or more, sequence identity) to a region containing the first non-coding exon of the Myo15 gene (nucleic acids from −6755 to −7209 with respect to the murine Myo15 translation start site, the sequence of which is set forth in SEQ ID NO: 1) or a functional portion or derivative thereof joined (e.g., operably linked) to a second region having at least 85% sequence identity (e.g., 85%, 90%, 95%, 96%, 97%, 98%, 99%, or more, sequence identity) to the nucleic acid sequence immediately preceding the translation start site of murine Myo15 (nucleic acids from −1 to −1157 with respect to the murine Myo15 translation start site, the sequence of which is set forth in SEQ ID NO: 2) or a functional portion or derivative thereof. The functional portion of SEQ ID NO: 1 may have the sequence of nucleic acids from −7166 to −7091 with respect to the murine Myo15 translation start site (set forth in SEQ ID NO: 3) and/or the sequence of nucleic acids from −7077 to −6983 with respect to the murine Myo15 translation start site (set forth in SEQ ID NO: 4). The first region may contain the nucleic acid sequence of SEQ ID NO: 3 fused to the nucleic acid sequence of SEQ ID NO: 4 with no intervening nucleic acids, as set forth in SEQ ID NO: 5, or the first region may contain the nucleic acid sequence of SEQ ID NO: 4 fused to the nucleic acid sequence of SEQ ID NO: 3 with no intervening nucleic acids, as set forth in SEQ ID NO: 6. Alternatively, the first region may contain the sequences of SEQ ID NO: 3 and SEQ ID NO: 4 joined by the endogenous intervening nucleic acid sequence (e.g., the first region may have or include the sequence of nucleic acids from −7166 to −6983 with respect to the murine Myo15 translation start site, as set forth in SEQ ID NO: 7 and SEQ ID NO: 27) or a nucleic acid linker. In polynucleotides in which the first region contains both SEQ ID NO: 3 and SEQ ID NO: 4, the two sequences can be included in any order (e.g., SEQ ID NO: 3 may be joined to (e.g., precede) SEQ ID NO: 4, or SEQ ID NO: 4 may be joined to (e.g., precede) SEQ ID NO: 3). The functional portion of SEQ ID NO: 2 may have the sequence of nucleic acids from −590 to −509 with respect to the Myo15 translation start site (set forth in SEQ ID NO: 8) and/or the sequence of nucleic acids from −266 to −161 with respect to the murine Myo15 translation start site (set forth in SEQ ID NO: 9). In some embodiments, the sequence containing SEQ ID NO: 8 has the sequence of SEQ ID NO: 28. In some embodiments, the sequence containing SEQ ID NO: 9 has the sequence of SEQ ID NO: 29. The second region may contain the nucleic acid sequence of SEQ ID NO: 8 fused to the nucleic acid sequence of SEQ ID NO: 9 with no intervening nucleic acids, as set forth in SEQ ID NO: 10, or the second region may contain the nucleic acid sequence of SEQ ID NO: 9 fused to the nucleic acid sequence of SEQ ID NO: 8 with no intervening nucleic acids, as set forth in SEQ ID NO: 11. The second region may contain the nucleic acid sequence of SEQ ID NO: 28 fused to the nucleic acid sequence of SEQ ID NO: 29 with no intervening nucleic acids, as set forth in SEQ ID NO: 32, or the second region may contain the nucleic acid sequence of SEQ ID NO: 29 fused to the nucleic acid sequence of SEQ ID NO: 28 with no intervening nucleic acids. Alternatively, the second region may contain the sequences of SEQ ID NO: 8 and SEQ ID NO: 9 joined by the endogenous intervening nucleic acid sequence (e.g., the second region may have the sequence of nucleic acids from −590 to −161 with respect to the murine Myo15 translation start site, as set forth in SEQ ID NO: 12) or a nucleic acid linker. In polynucleotides in which the second region contains both SEQ ID NO: 8 and SEQ ID NO: 9, the two sequences can be included in any order (e.g., SEQ ID NO: 8 may be joined to (e.g., precede) SEQ ID NO: 9, or SEQ ID NO: 9 may be joined to (e.g., precede) SEQ ID NO: 8).

The first region and the second region of the polynucleotide can be joined directly or can be joined by a nucleic acid linker. For example, the polynucleotide can contain the sequence of SEQ ID NO: 1 or a functional portion or derivative thereof (e.g., any one or more of SEQ ID NOs: 3-7 and 27, e.g., SEQ ID NOs 3 and 4) fused to the sequence of SEQ ID NO: 2 or a functional portion or derivative thereof (e.g., any one or more of SEQ ID NOs: 8-12, 28, 29, and 32, e.g., SEQ ID NOs 8 and 9) with no intervening nucleic acids. For example, the nucleic acid sequence of the polynucleotide that results from direct fusion of SEQ ID NO: 1 to SEQ ID NO: 2 is set forth in SEQ ID NO: 13. Alternatively, a linker can be used to join the sequence of SEQ ID NO: 1 or a functional portion or derivative thereof (e.g., any one or more of SEQ ID NOs: 3-7 and 27, e.g., SEQ ID NOs 3 and 4) to the sequence of SEQ ID NO: 2 or a functional portion or derivative thereof (e.g., any one or more of SEQ ID NOs: 8-12, 28, 29, and 32, e.g., SEQ ID NOs 8 and 9). Exemplary polynucleotides containing functional portions of both SEQ ID NO: 1 and SEQ ID NO: 2 are provided in SEQ ID NOs: 15, 16, 30, and 31.

The length of a nucleic acid linker for use in the polynucleotides described herein can be about 5 kb or less (e.g., about 5 kb, 4.5, kb, 4, kb, 3.5 kb, 3 kb, 2.5 kb, 2 kb, 1.5 kb, 1 kb, 900 bp, 800 bp, 700 bp, 600 bp, 500 bp, 450 bp, 400 bp, 350 bp, 300 bp, 250 bp, 200 bp, 150 bp, 100 bp, 90 bp, 80 bp, 70 bp, 60 bp, 50 bp, 40 bp, 30 bp, 25 bp, 20 bp, 15, bp, 10 bp, 5 bp, 4 bp, 3 bp, 2 bp, or less). Nucleic acid linkers that can be used in the polynucleotides described herein do not disrupt the ability of the polynucleotides of the invention to induce transgene expression in hair cells.

In some embodiments, the sequence of SEQ ID NO: 1 or a functional portion or derivative thereof (e.g., any one or more of SEQ ID NOs: 3-7 and 27, e.g., SEQ ID NOs 3 and 4) is joined (e.g., operably linked) to the sequence of SEQ ID NO: 2 or a functional portion or derivative thereof (e.g., any one or more of SEQ ID NOs: 8-12, 28, 29, and 32, e.g., SEQ ID NOs 8 and 9), and, in some embodiments, the order of the regions is reversed (e.g., the sequence of SEQ ID NO: 2 or a functional portion or derivative thereof (e.g., any one or more of SEQ ID NOs: 8-12, 28, 29, and 32, e.g., SEQ ID NOs 8 and 9) is joined (e.g., operably linked) to the sequence of SEQ ID NO: 1 or a functional portion or derivative thereof (e.g., any one or more of SEQ ID NOs: 3-7 and 27, e.g., SEQ ID NOs 3 and 4)). For example, the nucleic acid sequence of the polynucleotide that results from direct fusion of SEQ ID NO: 2 to SEQ ID NO: 1 is set forth in SEQ ID NO: 14. An example of a polynucleotide in which a functional portion or derivative of SEQ ID NO: 2 precedes a functional portion or derivative of SEQ ID NO: 1 is provided in SEQ ID NO: 35. Regardless of order, the sequence of SEQ ID NO: 1 or a functional portion or derivative thereof and the sequence of SEQ ID NO: 2 or a functional portion or derivative thereof can be joined by direct fusion or a nucleic acid linker, as described above.

In some embodiments, the polynucleotides described herein contain a region having at least 85% sequence identity (e.g., 85%, 90%, 95%, 96%, 97%, 98%, 99%, or more, sequence identity) to a region containing the first non-coding exon of the Myo15 gene (nucleic acids from −6755 to −7209 with respect to the murine Myo15 translation start site, the sequence of which is set forth in SEQ ID NO: 1) or a functional portion or derivative thereof. The functional portion of SEQ ID NO: 1 may have the sequence of nucleic acids from −7166 to −7091 with respect to the murine Myo15 translation start site (set forth in SEQ ID NO: 3) and/or the sequence of nucleic acids from −7077 to −6983 with respect to the Myo15 translation start site (set forth in SEQ ID NO: 4). The polynucleotide may contain the nucleic acid sequence of SEQ ID NO: 3 fused to the nucleic acid sequence of SEQ ID NO: 4 with no intervening nucleic acids, as set forth in SEQ ID NO: 5, or the polynucleotide may contain the nucleic acid sequence of SEQ ID NO: 4 fused to the nucleic acid of SEQ ID NO: 3 with no intervening nucleic acids, as set forth in SEQ ID NO: 6. Alternatively, the polynucleotide may contain the sequences of SEQ ID NO: 3 and SEQ ID NO: 4 joined by the endogenous intervening nucleic acid sequence (e.g., the first region may have or include the sequence of nucleic acids from −7166 to −6983 with respect to the murine Myo15 translation start site, as set forth in SEQ ID NO: 7 and SEQ ID NO: 27) or a nucleic acid linker. In polynucleotides that contain both SEQ ID NO: 3 and SEQ ID NO: 4, the two sequences can be included in any order (e.g., SEQ ID NO: 3 may be joined to (e.g., precede) SEQ ID NO: 4, or SEQ ID NO: 4 may be joined to (e.g., precede) SEQ ID NO: 3).

In some embodiments, the polynucleotides described herein contain a region having at least 85% sequence identity (e.g., 85%, 90%, 95%, 96%, 97%, 98%, 99%, or more, sequence identity) to the nucleic acid sequence immediately upstream of the murine Myo15 translation start site (nucleic acids from −1 to −1157 with respect to the murine Myo15 translation start site, the sequence of which is set forth in SEQ ID NO: 2) or a functional portion or derivative thereof. The functional portion of SEQ ID NO: 2 may have the sequence of nucleic acids from −590 to −509 with respect to the murine Myo15 translation start site (set forth in SEQ ID NO: 8) and/or the sequence of nucleic acids from −266 to −161 with respect to the murine Myo15 translation start site (set forth in SEQ ID NO: 9). In some embodiments, the sequence containing SEQ ID NO: 8 has the sequence of SEQ ID NO: 28. In some embodiments, the sequence containing SEQ ID NO: 9 has the sequence of SEQ ID NO: 29. The polynucleotide may contain the nucleic acid sequence of SEQ ID NO: 8 fused to the nucleic acid sequence of SEQ ID NO: 9 with no intervening nucleic acids, as set forth in SEQ ID NO: 10, or the polynucleotide may contain the nucleic acid sequence of SEQ ID NO: 9 fused to the nucleic acid sequence of SEQ ID NO: 8 with no intervening nucleic acids, as set forth in SEQ ID NO: 11. The polynucleotide may contain the nucleic acid sequence of SEQ ID NO: 28 fused to the nucleic acid sequence of SEQ ID NO: 29 with no intervening nucleic acids, as set forth in SEQ ID NO: 32, or the second region may contain the nucleic acid sequence of SEQ ID NO: 29 fused to the nucleic acid sequence of SEQ ID NO: 28 with no intervening nucleic acids. Alternatively, the polynucleotide may contain the sequences of SEQ ID NO: 8 and SEQ ID NO: 9 joined by the endogenous intervening nucleic acid sequence (e.g., the second region may have the sequence of nucleic acids from −590 to −161 with respect to the murine Myo15 translation start site, as set forth in SEQ ID NO: 12) or a nucleic acid linker. In polynucleotides that contain both SEQ ID NO: 8 and SEQ ID NO: 9, the two sequences can be included in any order (e.g., SEQ ID NO: 8 may be joined to (e.g., precede) SEQ ID NO: 9, or SEQ ID NO: 9 may be joined to (e.g., precede) SEQ ID NO: 8).

In some embodiments, the polynucleotides described herein contain a portion or derivative of a region having at least 85% sequence identity (e.g., 85%, 90%, 95%, 96%, 97%, 98%, 99%, or more, sequence identity) to a region containing the first non-coding exon of the Myo15 gene (nucleic acids from −6755 to −7209 with respect to the murine Myo15 translation start site, the sequence of which is set forth in SEQ ID NO: 1) flanked on either side by a portion or derivative of a region having at least 85% sequence identity (e.g., 85%, 90%, 95%, 96%, 97%, 98%, 99%, or more, sequence identity) to the nucleic acid sequence immediately upstream of the murine Myo15 translation start site (nucleic acids from −1 to −1157 with respect to the murine Myo15 translation start site, the sequence of which is set forth in SEQ ID NO: 2). For example, a functional portion or derivative of SEQ ID NO: 2, such as SEQ ID NO: 8 or 28 may be directly fused or joined by a nucleic acid linker to a portion of SEQ ID NO: 1, such as any one of SEQ ID NOs: 3-7 and 27, which is directly fused or joined by a nucleic acid linker to a different functional portion of SEQ ID NO: 2, such as SEQ ID NO: 9 or 29. In other embodiments, a functional portion or derivative of SEQ ID NO: 2, such as SEQ ID NO: 9 or 29 may be directly fused or joined by a nucleic acid linker to a portion of SEQ ID NO: 1, such as any one of SEQ ID NOs: 3-7 and 27, which is directly fused or joined by a nucleic acid linker to a different functional portion of SEQ ID NO: 2, such as SEQ ID NO: 8 or 28. For example, polynucleotides having at least 85% sequence identity (e.g., 85%, 90%, 95%, 96%, 97%, 98%, 99%, or more, sequence identity) to the nucleic acid sequence of SEQ ID NOs: 28, 27, and 29 can be fused to produce a polynucleotide having at least 85% sequence identity (e.g., 85%, 90%, 95%, 96%, 97%, 98%, 99%, or more, sequence identity) to the nucleic acid sequence of SEQ ID NO: 33. In some embodiments, polynucleotides having at least 85% sequence identity (e.g., 85%, 90%, 95%, 96%, 97%, 98%, 99%, or more, sequence identity) to the nucleic acid sequence of SEQ ID NOs: 29, 27, and 28 can be fused to produce a polynucleotide having at least 85% sequence identity (e.g., 85%, 90%, 95%, 96%, 97%, 98%, 99%, or more, sequence identity) to the nucleic acid sequence of SEQ ID NO: 34.

Human Myosin 15 Promoters

The polynucleotides of the compositions and methods described herein may also include nucleic acid sequences from regions of the human Myo15 locus that are capable of expressing a transgene specifically in hair cells, or variants thereof, such as a nucleic acid sequences that have at least 85% sequence identity (e.g., 85%, 90%, 95%, 96%, 97%, 98%, 99%, or more, sequence identity) to regions of the human Myo15 locus that are capable of expressing a transgene specifically in hair cells. The polynucleotides of the compositions and methods described herein can optionally include a linker operably linking the regions of the human Myo15 locus that are capable of expressing a transgene specifically in hair cells, or the regions of the human Myo15 locus can be joined directly without an intervening linker.

In some embodiments, the polynucleotides described herein contain a first region having at least 85% sequence identity (e.g., 85%, 90%, 95%, 96%, 97%, 98%, 99%, or more, sequence identity) to the sequence set forth in SEQ ID NO: 17 or a functional portion or derivative thereof joined (e.g., operably linked) to a second region having at least 85% sequence identity (e.g., 85%, 90%, 95%, 96%, 97%, 98%, 99%, or more, sequence identity) to the sequence set forth in SEQ ID NO: 18 or a functional portion or derivative thereof. The functional portion of SEQ ID NO: 17 may have the sequence set forth in SEQ ID NO: 19. The functional portion of SEQ ID NO: 18 may have the sequence set forth in SEQ ID NO: 20 and/or the sequence set forth in SEQ ID NO: 21. The second region may contain the nucleic acid sequence of SEQ ID NO: 20 fused to the nucleic acid sequence of SEQ ID NO: 21 with no intervening nucleic acids, as set forth in SEQ ID NO: 22, or the second region may contain the nucleic acid sequence of SEQ ID NO: 21 fused to the nucleic acid sequence of SEQ ID NO: 20 with no intervening nucleic acids, as set forth in SEQ ID NO: 23. Alternatively, the second region may contain the sequences of SEQ ID NO: 20 and SEQ ID NO: 21 joined by the endogenous intervening nucleic acid sequence (as set forth in SEQ ID NO: 24) or a nucleic acid linker. In polynucleotides in which the second region contains both SEQ ID NO: 20 and SEQ ID NO: 21, the two sequences can be included in any order (e.g., SEQ ID NO: 20 may be joined to (e.g., precede) SEQ ID NO: 21, or SEQ ID NO: 21 may be joined to (e.g., precede) SEQ ID NO: 20).

The first region and the second region of the polynucleotide can be joined directly or can be joined by a nucleic acid linker. For example, the polynucleotide can contain the sequence of SEQ ID NO: 17 or a functional portion or derivative thereof (e.g., SEQ ID NO: 19) fused to the sequence of SEQ ID NO: 18 or a functional portion or derivative thereof (e.g., any one or more of SEQ ID NOs: 20-24, e.g., SEQ ID NOs: 20 and/or 21) with no intervening nucleic acids. Alternatively, a linker can be used to join the sequence of SEQ ID NO: 17 or a functional portion or derivative thereof (e.g., SEQ ID NO: 19) to the sequence of SEQ ID NO: 18 or a functional portion or derivative thereof (e.g., any one or more of SEQ ID NOs: 20-24, e.g., SEQ ID NOs: 20 and/or 21). Exemplary polynucleotides containing functional portions of both SEQ ID NO: 17 and SEQ ID NO: 18 are provided in SEQ ID NOs: 25 and 26.

In some embodiments, the sequence of SEQ ID NO: 17 or a functional portion or derivative thereof (e.g., SEQ ID NO: 19) is joined (e.g., operably linked) to the sequence of SEQ ID NO: 18 or a functional portion or derivative thereof (e.g., any one or more of SEQ ID NOs: 20-24, e.g., SEQ ID NOs: 20 and 21), and, in some embodiments, the order of the regions is reversed (e.g., the sequence of SEQ ID NO: 18 or a functional portion or derivative thereof (e.g., any one or more of SEQ ID NOs: 20-24, e.g., SEQ ID NOs: 20 and/or 21) is joined (e.g., operably linked) to the sequence of SEQ ID NO: 17 or a functional portion or derivative thereof (e.g., SEQ ID NO: 19). Regardless of order, the sequence of SEQ ID NO: 17 or a functional portion or derivative thereof and the sequence of SEQ ID NO: 18 or a functional portion or derivative thereof can be joined by direct fusion or a nucleic acid linker, as described above.

In some embodiments, the polynucleotides described herein contain a region having at least 85% sequence identity (e.g., 85%, 90%, 95%, 96%, 97%, 98%, 99%, or more, sequence identity) to a region containing the sequence set forth in SEQ ID NO: 17 or a functional portion or derivative thereof. The functional portion of SEQ ID NO: 17 may have the sequence of nucleic acids set forth in SEQ ID NO: 19.

In some embodiments, the polynucleotides described herein contain a region having at least 85% sequence identity (e.g., 85%, 90%, 95%, 96%, 97%, 98%, 99%, or more, sequence identity) to the sequence set forth in SEQ ID NO: 18 or a functional portion or derivative thereof. The functional portion of SEQ ID NO: 18 may have the sequence set forth in SEQ ID NO: 20 and/or the sequence set forth in SEQ ID NO: 21. The polynucleotide may contain the nucleic acid sequence of SEQ ID NO: 20 fused to the nucleic acid sequence of SEQ ID NO: 21 with no intervening nucleic acids, as set forth in SEQ ID NO: 22, or the polynucleotide may contain the nucleic acid sequence of SEQ ID NO: 21 fused to the nucleic acid sequence of SEQ ID NO: 20 with no intervening nucleic acids, as set forth in SEQ ID NO: 23. Alternatively, the polynucleotide may contain the sequences of SEQ ID NO: 20 and SEQ ID NO: 21 joined by the endogenous intervening nucleic acid sequence (e.g., as set forth in SEQ ID NO: 24) or a nucleic acid linker. In polynucleotides that contain both SEQ ID NO: 20 and SEQ ID NO: 21, the two sequences can be included in any order (e.g., SEQ ID NO: 20 may be joined to (e.g., precede) SEQ ID NO: 21, or SEQ ID NO: 21 may be joined to (e.g., precede) SEQ ID NO: 20).

The length of a nucleic acid linker for use in the polynucleotides described herein can be about 5 kb or less (e.g., about 5 kb, 4.5, kb, 4, kb, 3.5 kb, 3 kb, 2.5 kb, 2 kb, 1.5 kb, 1 kb, 900 bp, 800 bp, 700 bp, 600 bp, 500 bp, 450 bp, 400 bp, 350 bp, 300 bp, 250 bp, 200 bp, 150 bp, 100 bp, 90 bp, 80 bp, 70 bp, 60 bp, 50 bp, 40 bp, 30 bp, 25 bp, 20 bp, 15, bp, 10 bp, 5 bp, 4 bp, 3 bp, 2 bp, or less). Nucleic acid linkers that can be used in the polynucleotides described herein do not disrupt the ability of the polynucleotides of the invention to induce transgene expression in hair cells.

The foregoing nucleic acid sequences are summarized in Table 2, below.

TABLE 2

Exemplary nucleotide sequences for use in the polynucleotides described herein

| SEQ ID NO. | Description of nucleic acid sequence | Nucleic Acid Sequence |
|---|---|---|
| 1 | Region containing non-coding exon 1 of murine Myo15 (-6755 to -7209) | CTGCAGCTCAGCCTACTACTTGCTTTCCAGGCTGTTCCTAGT TCCCATGTCAGCTGCTTGTGCTTTCCAGAGACAAAACAGGA ATAATAGATGTCATTAAATATACATTGGGCCCCAGGCGGTCA ATGTGGCAGCCTGAGCCTCCTTTCCATCTCTGTGGAGGCAG ACATAGGACCCCCAACAAACAGCATGCAGGTTGGGAGCCAG CCACAGGACCCAGGTAAGGGGCCCTGGGTCCTTAAGCTTCT GCCACTGGCTCCGGCATTGCAGAGAGAAGAGAAGGGGCGG CAGAGCTGAACCTTAGCCTTGCCTTCCTGGGTACCCTTCTG AGCCTCACTGTCTTCTGTGAGATGGGCAAAGTGCGGGTGTG ACTCCTTGGCAACGGTGTTACACCAGGGCAGGTAAAGTTGT AGTTATTTGTGGGGTACACCAGGACTGTTAAAGGTGTAACTA T |
| 2 | Region immediately preceding the translation start site of murine Myo15 (-1 to -1157) | GGTCTCACCCAGCATTTTCACTTCTAATAAGTTCAAATGTGA TACGGCACCTTTCTAAAAATTAGTTTTCAGGGAAATAGGGTT CAAAACTGGTAGTGGTAGGGTCCATTCTCACGACCCCCAGG CCTGCTAACCCTGACCAAGCTACCTATTACTTACCCTCCTCT TTCTCCTCCTCCTCTTTCTCCTTCTCCTGCTTCCCCTCTTCCT TCTCCCTCCCTTCCTCTCCCTCCTCCCCCTCCTTGGCTGTGA TCAGATCCAGAGCCTGAATGAGCCTCCTGACCCCACACCCC CACTAGCATGGGCCTGCAAGTGCCCAGAAGTCCCTCCTGCC TCCTAAACTGCCCAGCCGATCCATTAGCTCTTCCTTCTTCCC AGTGAAAGAAGCAGGCACAGCCTGTCCCTCCCGTTCTACAG AAAGGAAGCTACAGCACAGGGAGGGCAAAGGCCTTCCTG GGACTAGACAGTTGATCAACAGCAGGACTGGAGAGCTGGG CTCCATTTTTGTTCCTTGGTGCCCTGCCCCTCCCCATGACCT GCAGAGACATTCAGCCTGCCAGGCTTTATGAGGTGGGAGCT GGGCTCTCCCTGATGTATTATTCAGCTCCCTGGAGTTGGCC AGCTCCTGTTACACTGGCCACAGCCCTGGGCATCCGCTTCT CACTTCTAGTTTCCCCTCCAAGGTAATGTGGTGGGTCATGAT CATTCTATCCTGGCTTCAGGGACCTGACTCCACTTTGGGGC CATTCGAGGGGTCTAGGGTAGATGATGTCCCCCTGTGGGGA TTAATGTCCTGCTCTGTAAAACTGAGCTAGCTGAGATCCAGG AGGGCTTGGCCAGAGACAGCAAGTTGTTGCCATGGTGACTT TAAAGCCAGGTTGCTGCCCCAGCACAGGCCTCCCAGTCTAC CCTCACTAGAAAACAACACCCAGGCACTTTCCACCACCTCTC AAAGGTGAAACCCAAGGCTGGTCTAGAGAATGAATTATGGA TCCTCGCTGTCCGTGCCACCCAGCTAGTCCCAGCGGCTCAG ACACTGAGGAGAGACTGTAGGTTCAGCTACAAGCAAAAGA CCTAGCTGGTCTCCAAGCAGTGTCTCCAAGTCCCTGAACCT GTGACACCTGCCCCAGGCATCATCAGGCACAGAGGGCCAC C |
| 3 | Portion of SEQ ID NO: 1 (-7166 to -7091) | CCCATGTCAGCTGCTTGTGCTTTCCAGAGACAAAACAGGAA TAATAGATGTCATTAAATATACATTGGGCCCCAGG |
| 4 | Portion of SEQ ID NO: 1 (-7077 to -6983) | AGCCTGAGCCTCCTTTCCATCTCTGTGGAGGCAGACATAGG ACCCCCAACAAACAGCATGCAGGTTGGGAGCCAGCCACAG GACCCAGGTAAGGG |
| 5 | Portion of SEQ ID NO: 1 (SEQ ID NO: 3 fused to SEQ ID NO: 4) | CCCATGTCAGCTGCTTGTGCTTTCCAGAGACAAAACAGGAA TAATAGATGTCATTAAATATACATTGGGCCCCAGGAGCCTGA GCCTCCTTTCCATCTCTGTGGAGGCAGACATAGGACCCCCA ACAAACAGCATGCAGGTTGGGAGCCAGCCACAGGACCCAG GTAAGGG |

TABLE 2-continued

Exemplary nucleotide sequences for use in the polynucleotides described herein

| SEQ ID NO. | Description of nucleic acid sequence | Nucleic Acid Sequence |
|---|---|---|
| 6 | Portion of SEQ ID NO: 1 (SEQ ID NO: 4 fused to SEQ ID NO: 3) | AGCCTGAGCCTCCTTTCCATCTCTGTGGAGGCAGACATAGG ACCCCCAACAAACAGCATGCAGGTTGGGAGCCAGCCACAG GACCCAGGTAAGGGCCCATGTCAGCTGCTTGTGCTTTCCAG AGACAAAACAGGAATAATAGATGTCATTAAATATACATTGGG CCCCAGG |
| 7 | Portion of SEQ ID NO: 1 (-7166 to -6983) | CCCATGTCAGCTGCTTGTGCTTTCCAGAGACAAAACAGGAA TAATAGATGTCATTAAATATACATTGGGCCCCAGGCGGTCAA TGTGGCAGCCTGAGCCTCCTTTCCATCTCTGTGGAGGCAGA CATAGGACCCCCAACAAACAGCATGCAGGTTGGGAGCCAG CCACAGGACCCAGGTAAGGG |
| 8 | Portion of SEQ ID NO: 2 (-590 to -509) | TGAGGTGGGAGCTGGGCTCTCCCTGATGTATTATTCAGCTC CCTGGAGTTGGCCAGCTCCTGTTACACTGGCCACAGCCCTG |
| 9 | Portion of SEQ ID NO: 2 (-266 to -161) | CACAGGCCTCCCAGTCTACCCTCACTAGAAAACAACACCCA GGCACTTTCCACCACCTCTCAAAGGTGAAACCCAAGGCTGG TCTAGAGAATGAATTATGGATCCT |
| 10 | Portion of SEQ ID NO: 2 (SEQ ID NO: 8 fused to SEQ ID NO: 9) | TGAGGTGGGAGCTGGGCTCTCCCTGATGTATTATTCAGCTC CCTGGAGTTGGCCAGCTCCTGTTACACTGGCCACAGCCCTG CACAGGCCTCCCAGTCTACCCTCACTAGAAAACAACACCCA GGCACTTTCCACCACCTCTCAAAGGTGAAACCCAAGGCTGG TCTAGAGAATGAATTATGGATCCT |
| 11 | Portion of SEQ ID NO: 2 (SEQ ID NO: 9 fused to SEQ ID NO: 8) | CACAGGCCTCCCAGTCTACCCTCACTAGAAAACAACACCCA GGCACTTTCCACCACCTCTCAAAGGTGAAACCCAAGGCTGG TCTAGAGAATGAATTATGGATCCTTGAGGTGGGAGCTGGGC TCTCCCTGATGTATTATTCAGCTCCCTGGAGTTGGCCAGCTC CTGTTACACTGGCCACAGCCCTG |
| 12 | Portion of SEQ ID NO: 2 (-590 to -161) | TGAGGTGGGAGCTGGGCTCTCCCTGATGTATTATTCAGCTC CCTGGAGTTGGCCAGCTCCTGTTACACTGGCCACAGCCCTG GGCATCCGCTTCTCACTTCTAGTTTCCCCTCCAAGGTAATGT GGTGGGTCATGATCATTCTATCCTGGCTTCAGGGACCTGAC TCCACTTTGGGGCCATTCGAGGGGTCTAGGGTAGATGATGT CCCCCTGTGGGGATTAATGTCCTGCTCTGTAAAACTGAGCT AGCTGAGATCCAGGAGGGCTTGGCCAGAGACAGCAAGTTG TTGCCATGGTGACTTTAAAGCCAGGTTGCTGCCCCAGCACA GGCCTCCCAGTCTACCCTCACTAGAAAACAACACCCAGGCA CTTTCCACCACCTCTCAAAGGTGAAACCCAAGGCTGGTCTA GAGAATGAATTATGGATCCT |
| 13 | SEQ ID NO: 1 fused to SEQ ID NO: 2 | CTGCAGCTCAGCCTACTACTTGCTTTCCAGGCTGTTCCTAGT TCCCATGTCAGCTGCTTGTGCTTTCCAGAGACAAAACAGGA ATAATAGATGTCATTAAATATACATTGGGCCCCAGGCGGTCA ATGTGGCAGCCTGAGCCTCCTTTCCATCTCTGTGGAGGCAG ACATAGGACCCCCAACAAACAGCATGCAGGTTGGGAGCCAG CCACAGGACCCAGGTAAGGGGCCCTGGGTCCTTAAGCTTCT GCCACTGGCTCCGGCATTGCAGAGAGAAGAGAAGGGGCGG CAGAGCTGAACCTTAGCCTTGCCTTCCTGGGTACCCTTCTG AGCCTCACTGTCTTCTGTGAGATGGGCAAAGTGCGGGTGTG ACTCCTTGGCAACGGTGTTACACCAGGGCAGGTAAAGTTGT AGTTATTTGTGGGGTACACCAGGACTGTTAAAGGTGTAACTA TGGTCTCACCCAGCATTTTCACTTCTAATAAGTTCAAATGTG ATACGGCACCTTTCTAAAAATTAGTTTTCAGGGAAATAGGGT TCAAAACTGGTAGTGGTAGGGTCCATTCTCACGACCCCCAG GCCTGCTAACCCTGACCAAGCTACCTATTACTTACCCTCCTC TTTCTCCTCCTCCTCTTTCTCCTTCTCCTGCTTCCCCTCTTCC TTCTCCCTCCCTTCCTCTCCCTCCTCCCCCTCCTTGGCTGTG ATCAGATCCAGAGCCTGAATGAGCCTCCTGACCCCACACCC CCACTAGCATGGGCCTGCAAGTGCCCAGAAGTCCCTCCTGC CTCCTAAACTGCCCAGCCGATCCATTAGCTCTTCCTTCTTCC CAGTGAAAGAAGCAGGCACAGCCTGTCCCTCCCGTTCTACA GAAAGGAAGCTACAGCACAGGGAGGGCCAAAGGCCTTCCT GGGACTAGACAGTTGATCAACAGCAGGACTGGAGAGCTGG GCTCCATTTTTGTTCCTTGGTGCCCTGCCCCTCCCCATGACC TGCAGAGACATTCAGCCTGCCAGGCTTTATGAGGTGGGAGC TGGGCTCTCCCTGATGTATTATTCAGCTCCCTGGAGTTGGC CAGCTCCTGTTACACTGGCCACAGCCCTGGGCATCCGCTTC TCACTTCTAGTTTCCCCTCCAAGGTAATGTGGTGGGTCATGA TCATTCTATCCTGGCTTCAGGGACCTGACTCCACTTTGGGG CCATTCGAGGGGTCTAGGGTAGATGATGTCCCCCTGTGGG GATTAATGTCCTGCTCTGTAAAACTGAGCTAGCTGAGATCCA |

TABLE 2-continued

Exemplary nucleotide sequences for use in the polynucleotides described herein

| SEQ ID NO. | Description of nucleic acid sequence | Nucleic Acid Sequence |
|---|---|---|
| | | GGAGGGCTTGGCCAGAGACAGCAAGTTGTTGCCATGGTGA CTTTAAAGCCAGGTTGCTGCCCCAGCACAGGCCTCCCAGTC TACCCTCACTAGAAAACAACACCCAGGCACTTTCCACCACCT CTCAAAGGTGAAACCCAAGGCTGGTCTAGAGAATGAATTAT GGATCCTCGCTGTCCGTGCCACCCAGCTAGTCCCAGCGGC TCAGACACTGAGGAGAGACTGTAGGTTCAGCTACAAGCAAA AAGACCTAGCTGGTCTCCAAGCAGTGTCTCCAAGTCCCTGA ACCTGTGACACCTGCCCCAGGCATCATCAGGCACAGAGGG CCACC |
| 14 | SEQ ID NO: 2 fused to SEQ ID NO: 1 | GGTCTCACCCAGCATTTTCACTTCTAATAAGTTCAAATGTGA TACGGCACCTTTCTAAAAATTAGTTTTCAGGGAAATAGGGTT CAAAACTGGTAGTGGTAGGGTCCATTCTCACGACCCCCAGG CCTGCTAACCCTGACCAAGCTACCTATTACTTACCCTCCTCT TTCTCCTCCTCCTCTTTCTCCTTCTCCTGCTTCCCCTCTTCCT TCTCCCTCCCTTCCTCTCCCTCCTCCCCCTCCTTGGCTGTGA TCAGATCCAGAGCCTGAATGAGCCTCCTGACCCCACACCCC CACTAGCATGGGCCTGCAAGTGCCCAGAAGTCCCTCCTGCC TCCTAAACTGCCCAGCCGATCCATTAGCTCTTCCTTCTTCCC AGTGAAAGAAGCAGGCACAGCCTGTCCCTCCCGTTCTACAG AAAGGAAGCTACAGCACAGGGAGGGCCAAAGGCCTTCCTG GGACTAGACAGTTGATCAACAGCAGGACTGGAGAGCTGGG CTCCATTTTGTTCCTTGGTGCCCTGCCCCTCCCCATGACCT GCAGAGACATTCAGCCTGCCAGGCTTTATGAGGTGGGAGCT GGGCTCTCCCTGATGTATTATTCAGCTCCCTGGAGTTGGCC AGCTCCTGTTACACTGGCCACAGCCCTGGGCATCCGCTTCT CACTTCTAGTTTCCCCTCCAAGGTAATGTGGTGGGTCATGAT CATTCTATCCTGGCTTCAGGGACCTGACTCCACTTTGGGGC CATTCGAGGGGTCTAGGGTAGATGATGTCCCCCTGTGGGGA TTAATGTCCTGCTCTGTAAAACTGAGCTAGCTGAGATCCAGG AGGGCTTGGCCAGAGACAGCAAGTTGTTGCCATGGTGACTT TAAAGCCAGGTTGCTGCCCCAGCACAGGCCTCCCAGTCTAC CCTCACTAGAAAACAACACCCAGGCACTTTCCACCACCTCTC AAAGGTGAAACCCAAGGCTGGTCTAGAGAATGAATTATGGA TCCTCGCTGTCCGTGCCACCCAGCTAGTCCCAGCGGCTCAG ACACTGAGGAGAGACTGTAGGTTCAGCTACAAGCAAAAGA CCTAGCTGGTCTCCAAGCAGTGTCTCCAAGTCCCTGAACCT GTGACACCTGCCCCAGGCATCATCAGGCACAGAGGGCCAC CCTGCAGCTCAGCCTACTACTTGCTTTCCAGGCTGTTCCTAG TTCCCATGTCAGCTGCTTGTGCTTTCCAGAGACAAAACAGGA ATAATAGATGTCATTAAATATACATTGGGCCCCAGGCGGTCA ATGTGGCAGCCTGAGCCTCCTTTCCATCTCTGTGGAGGCAG ACATAGGACCCCAACAAACAGCATGCAGGTTGGGAGCCAG CCACAGGACCCAGGTAAGGGGCCCTGGGTCCTTAAGCTTCT GCCACTGGCTCCGGCATTGCAGAGAGAAGAGAAGGGGCGG CAGAGCTGAACCTTAGCCTTGCCTTCCTGGGTACCCTTCTG AGCCTCACTGTCTTCTGTGAGATGGGCAAAGTGCGGGTGTG ACTCCTTGGCAACGGTGTTACACCAGGGCAGGTAAAGTTGT AGTTATTTGTGGGGTACACCAGGACTGTTAAAGGTGTAACTA T |
| 15 | Portion of SEQ ID NO: 1 that contains SEQ ID NO: 3 and SEQ ID NO: 4 fused to portion of SEQ ID NO: 2 that contains SEQ ID NO: 8 and SEQ ID NO: 9 | CTGCAGCTCAGCCTACTACTTGCTTTCCAGGCTGTTCCTAGT TCCCATGTCAGCTGCTTGTGCTTTCCAGAGACAAAACAGGA ATAATAGATGTCATTAAATATACATTGGGCCCCAGGCGGTCA ATGTGGCAGCCTGAGCCTCCTTTCCATCTCTGTGGAGGCAG ACATAGGACCCCAACAAACAGCATGCAGGTTGGGAGCCAG CCACAGGACCCAGGTAAGGGGCCCTGGGTCCTTAAGCTTCT GCCACTGGCTCCGGCATTGCAGAGAGAAGAGAAGGGGCGG CAGACTGGAGAGCTGGGCTCCATTTTGTTCCTTGGTGCCC TGCCCCTCCCCATGACCTGCAGAGACATTCAGCCTGCCAGG CTTTATGAGGTGGGAGCTGGGCTCTCCCTGATGTATTATTCA GCTCCCTGGAGTTGGCCAGCTCCTGTTACACTGGCCACAGC CCTGGGCATCCGCTTCTCACTTCTAGTTTCCCCTCCAAGGTA ATGTGGTGGGTCATGATCATTCTATCCTGGCTTCAGGGACC TGACTCCACTTTGGGGCCATTCGAGGGGTCTAGGGTAGATG ATGTCCCCCTGTGGGGATTAATGTCCTGCTCTGTAAAACTGA GCTAGCTGAGATCCAGGAGGGCTTGGCCAGAGACAGCAAG TTGTTGCCATGGTGACTTTAAAGCCAGGTTGCTGCCCCAGC ACAGGCCTCCCAGTCTACCCTCACTAGAAAACAACACCCAG GCACTTTCCACCACCTCTCAAAGGTGAAACCCAAGGCTGGT CTAGAGAATGAATTATGGATCCTCGCTGTCCGTGCCACCCA GCTAGTCCCAGCGGCTCAGACACTGAGGAGAGACTGTAGG TTCAGCTACAAGCAAAAGACCTAGCTGGTCTCCAAGCAGT GTCTCCAAGTCCCTGAACCTGTGACACCTGCCCCAGGCATC ATCAGGCACAGAGGGCCACC |

TABLE 2-continued

Exemplary nucleotide sequences for use in the polynucleotides described herein

| SEQ ID NO. | Description of nucleic acid sequence | Nucleic Acid Sequence |
|---|---|---|
| 16 | Portion of SEQ ID NO: 1 that contains SEQ ID NO: 3 and SEQ ID NO: 4 fused to portion of SEQ ID NO: 2 that contains SEQ ID NO: 8 and SEQ ID NO: 9 | CTGCAGCTCAGCCTACTACTTGCTTTCCAGGCTGTTCCTAGT TCCCATGTCAGCTGCTTGTGCTTTCCAGAGACAAAACAGGA ATAATAGATGTCATTAAATATACATTGGGCCCCAGGCGGTCA ATGTGGCAGCCTGAGCCTCCTTTCCATCTCTGTGGAGGCAG ACATAGGACCCCAACAAACAGCATGCAGGTTGGGAGCCAG CCACAGGACCCAGGTAAGGGGCCCTGGGTCCTTTTTATGAG GTGGGAGCTGGGCTCTCCCTGATGTATTATTCAGCTCCCTG GAGTTGGCCAGCTCCTGTTACACTGGCCACAGCCCTGGGCA TCCGCTGCCATGGTGACTTTAAAGCCAGGTTGCTGCCCCAG CACAGGCCTCCCAGTCTACCCTCACTAGAAAACAACACCCA GGCACTTTCCACCACCTCTCAAAGGTGAAACCCAAGGCTGG TCTAGAGAATGAATTATGGATCCTCGCTGTCCGTGCCACCC AGCTAGTCCCAGCGGCTCAGACACTG |
| 17 | Region 1 of the human Myo15 promoter | GTATGCCTTTTGAGATGGATGCAGCAGGTTCTGTGAGGCTG CCAGGAGGGGTAGAGTTCCCGGGGGCCTCGGGCCCCGCT GGAGTGTGGAGCAGGCCCATGCTCAGCTCTCCAGGCTGTT CGTGGCTCCCCTGTCAGCTGCTCACTCCTTTCCAGAGACAA AACAGGAATAATAGACATCATTAAATATACATAGGGCCCCAG GCGGTCGGCGTGGTGGGCTGGGCCTCCCTTCC |
| 18 | Region 2 of human Myo15 promoter | TGCCCTGCCTTCTGAGCCGGCAGCCTGGCTCCCCACCCCAT GTATTATTCAGCTCCTGAGAGCCAGCCAGCTCCTGTTACACT GACCGCAGCCCAGCACCTGCTCTGCCCATTCCCCTCCTCCC TTGCCTAGGACCTAGAGGGTTCAAAGTTCTCCTCCAAGATG ACTTGGTGGGCTTTGGCCATCCCACCCTAGGCCCCACTTCT GGCCCAGTGCAGGTGTGCTGGTGATTTAGGGCAGGTGGCA TTCCATCTCTGTGGCTCAATGTCTTCCTCTGTGAAGCCGAAG TGACCCAAGGGCTCCCTTCATGGGGTTGAGCCAGCTGTGG CCCAGGGAGGGCCTAACCAGGATGAGCACTGATGTTGCCAT GACGACTCCGAGGCCAGAATGTCTCCCCCAGCACAGGCCT CATAGGCAGGCTTCCCCATCCTGGTAAACAACACCCACACA CTTTCTACTACTGCTCTAGGGTGAAACCCAAGGCGCTCTAG AGGAGATGAATTATGGATCCGCCCTCCCGGAATCCTGGCTC GGCCCTCCCCACGCCACCCAGGGCCAGTCGGGTCTGCTCA CAGCCCGAGGAGGCCGCGTGTCCAGCCGCGGGCAAGAGA CAGAGCAGGTCCCTGTGTCTCCAAGTCCCTGAGCCCGTGAC ACCGGCCCCAGGCCCTGTAGAGAGCAGGCAGCCACC |
| 19 | Portion of SEQ ID NO: 17 | CCCCTGTCAGCTGCTCACTCCTTTCCAGAGACAAAACAGGA ATAATAGACATCATTAAATATACATAGGGCCCCAGG |
| 20 | Portion of SEQ ID NO: 18 | TGAGCCGGCAGCCTGGCTCCCCACCCCATGTATTATTCAGC TCCTGAGAGCCAGCCAGCTCCTGTTACACTGACCGCAGCCC |
| 21 | Portion of SEQ ID NO: 18 | CACAGGCCTCATAGGCAGGCTTCCCCATCCTGGTAAACAAC ACCCACACACTTTCTACTACTGCTCTAGGGTGAAACCCAAG GCGCTCTAGAGGAGATGAATTATGGATCC |
| 22 | Portion of SEQ ID NO: 18 (SEQ ID NO: 20 fused to SEQ ID NO: 21) | TGAGCCGGCAGCCTGGCTCCCCACCCCATGTATTATTCAGC TCCTGAGAGCCAGCCAGCTCCTGTTACACTGACCGCAGCCC CACAGGCCTCATAGGCAGGCTTCCCCATCCTGGTAAACAAC ACCCACACACTTTCTACTACTGCTCTAGGGTGAAACCCAAG GCGCTCTAGAGGAGATGAATTATGGATCC |
| 23 | Portion of SEQ ID NO: 18 (SEQ ID NO: 21 fused to SEQ ID NO: 20) | CACAGGCCTCATAGGCAGGCTTCCCCATCCTGGTAAACAAC ACCCACACACTTTCTACTACTGCTCTAGGGTGAAACCCAAG GCGCTCTAGAGGAGATGAATTATGGATCCTGAGCCGGCAGC CTGGCTCCCCACCCCATGTATTATTCAGCTCCTGAGAGCCA GCCAGCTCCTGTTACACTGACCGCAGCCC |
| 24 | Portion of SEQ ID NO: 18 (contiguous sequence including SEQ ID NO: 20 and SEQ ID NO: 21) | TGAGCCGGCAGCCTGGCTCCCCACCCCATGTATTATTCAGC TCCTGAGAGCCAGCCAGCTCCTGTTACACTGACCGCAGCCC AGCACCTGCTCTGCCCATTCCCCTCCTCCCTTGCCTAGGAC CTAGAGGGTTCAAAGTTCTCCTCCAAGATGACTTGGTGGGC TTTGGCCATCCCACCCTAGGCCCCACTTCTGGCCCAGTGCA GGTGTGCTGGTGATTTAGGGCAGGTGGCATTCCATCTCTGT GGCTCAATGTCTTCCTCTGTGAAGCCGAAGTGACCCAAGGG CTCCCTTCATGGGGTTGAGCCAGCTGTGGCCCAGGGAGGG CCTAACCAGGATGAGCACTGATGTTGCCATGACGACTCCGA GGCCAGAATGTCTCCCCCAGCACAGGCCTCATAGGCAGGC TTCCCCATCCTGGTAAACAACACCCACACACTTTCTACTACT GCTCTAGGGTGAAACCCAAGGCGCTCTAGAGGAGATGAATT ATGGATCC |

TABLE 2-continued

Exemplary nucleotide sequences for use in the polynucleotides described herein

| SEQ ID NO. | Description of nucleic acid sequence | Nucleic Acid Sequence |
|---|---|---|
| 25 | Polynucleotide containing SEQ ID NO: 17 and SEQ ID NO: 18 | GTATGCCTTTTGAGATGGATGCAGCAGGTTCTGTGAGGCTG CCAGGAGGGGTAGAGTTCCCGGGGGCCTCGGGCCCCGCT GGAGTGTGGAGCAGGCCCATGCTCAGCTCTCCAGGCTGTT CGTGGCTCCCCTGTCAGCTGCTCACTCCTTTCCAGAGACAA AACAGGAATAATAGACATCATTAAATATACATAGGGCCCCAG GCGGTCGGCGTGGTGGGCTGGGCCTCCCTTCCCCATAACA CTGAGCTGCTCTGCTGGGCCAACCGTGCTCCTGGGCCAGC CAGAGGACCCCCATGAGGCGGCATGCAGGCGGGGAGCAG GCCACAGAACGCAGGTAAGGAGACCTTAGCCTAGAGTCCTT GGGGTCTGTCACTGGCCACCCTCGCATCCCAGGCTGCAGG AAACTGAGGCCCAGAGAGGACAAGGACTTTCCTGGACCCAC ACAGCCAGTCAGTGACAGAGCCTAGGGTCTGAGCCAGGCC TGACCCAACCTCCATTTCTGCCTCTCTACCCCTGCCCCCGC CCCAACACACACACACACACAAGTGGAGTTCCACTGAAACG CCCCTCCTTGCCCTGCCTTCTGAGCCGGCAGCCTGGCTCCC CACCCCATGTATTATTCAGCTCCTGAGAGCCAGCCAGCTCC TGTTACACTGACCGCAGCCCAGCACCTGCTCTGCCCATTCC CCTCCTCCCTTGCCTAGGACCTAGAGGGTTCAAAGTTCTCC TCCAAGATGACTTGGTGGGCTTTGGCCATCCCACCCTAGGC CCCACTTCTGGCCCAGTGCAGGTGTGCTGGTGATTTAGGGC AGGTGGCATTCCATCTCTGTGGCTCAATGTCTTCCTCTGTGA AGCCGAAGTGACCCAAGGGCTCCCTTCATGGGGTTGAGCC AGCTGTGGCCCAGGGAGGGCCTAACCAGGATGAGCACTGA TGTTGCCATGACGACTCCGAGGCCAGAATGTCTCCCCCAGC ACAGGCCTCATAGGCAGGCTTCCCCATCCTGGTAAACAACA CCCACACACTTTCTACTACTGCTCTAGGGTGAAACCCAAGG CGCTCTAGAGGAGATGAATTATGGATCCGCCCTCCCGGAAT CCTGGCTCGGCCCTCCCCACGCCACCCAGGGCCAGTCGGG TCTGCTCACAGCCCGAGGAGGCCGCGTGTCCAGCCGCGGG CAAGAGACAGAGCAGGTCCCTGTGTCTCCAAGTCCCTGAGC CCGTGACACCGGCCCCAGGCCCTGTAGAGAGCAGGCAGCC ACC |
| 26 | Polynucleotide containing SEQ ID NO: 19, SEQ ID NO: 20, and SEQ ID NO: 21 | GCAGGCCCATGCTCAGCTCTCCAGGCTGTTCGTGGCTCCCC TGTCAGCTGCTCACTCCTTTCCAGAGACAAAACAGGAATAAT AGACATCATTAAATATACATAGGGCCCCAGGCGGTCGGCGT GGTGGGCTGGGCCTCCCTTCCCCATAACACTGAGCTGCTCT GCTGGGCCAACCGTGCTCCTGGGCCAGCCAGAGGACCCCC ATGAGGCGGCATGCAGGCGGGGAGCAGGCCACAGAACGCA GGTAAGGAGACCTTGCCTTCTGAGCCGGCAGCCTGGCTCC CCACCCCATGTATTATTCAGCTCCTGAGAGCCAGCCAGCTC CTGTTACACTGACCGCAGCCCAGCACCTGCTCTGCCCATTC CCTCCTCCCTTGCCTAGGACCTAGAGGGTTCAAAGTTCTC CTCCAAGATGACTTGGTGGGCTTTGGCCATCGGGCCTAACC AGGATGAGCACTGATGTTGCCATGACGACTCCGAGGCCAGA ATGTCTCCCCCAGCACAGGCCTCATAGGCAGGCTTCCCCAT CCTGGTAAACAACACCCACACACTTTCTACTACTGCTCTAGG GTGAAACCCAAGGCGCTCTAGAGGAGATGAATTATGGATCC GCCCTCCCGGAATCCTGGCTCGGCCCTCCCCACGC |
| 27 | Portion of SEQ ID NO: 1 that contains SEQ ID NO: 3 and SEQ ID NO: 4 | CTGCAGCTCAGCCTACTACTTGCTTTCCAGGCTGTTCCTAGT TCCCATGTCAGCTGCTTGTGCTTTCCAGAGACAAAACAGGA ATAATAGATGTCATTAAATATACATTGGGCCCCAGGCGGTCA ATGTGGCAGCCTGAGCCTCCTTTCCATCTCTGTGGAGGCAG ACATAGGACCCCCAACAAACAGCATGCAGGTTGGGAGCCAG CCACAGGACCCAGGTAAGGGGCCCTGGGTCCTT |
| 28 | Portion of SEQ ID NO: 2 that contains SEQ ID NO: 8 | TTTATGAGGTGGGAGCTGGGCTCTCCCTGATGTATTATTCAG CTCCCTGGAGTTGGCCAGCTCCTGTTACACTGGCCACAGCC CTGGGCATCCGC |
| 29 | Portion of SEQ ID NO: 2 that contains SEQ ID NO: 9 | TGCCATGGTGACTTTAAAGCCAGGTTGCTGCCCCAGCACAG GCCTCCCAGTCTACCCTCACTAGAAAACAACACCCAGGCAC TTTCCACCACCTCTCAAAGGTGAAACCCAAGGCTGGTCTAG AGAATGAATTATGGATCCTCGCTGTCCGTGCCACCCAGCTA GTCCCAGCGGCTCAGACACTG |
| 30 | SEQ ID NO: 27 fused to SEQ ID NO: 28 | CTGCAGCTCAGCCTACTACTTGCTTTCCAGGCTGTTCCTAGT TCCCATGTCAGCTGCTTGTGCTTTCCAGAGACAAAACAGGA ATAATAGATGTCATTAAATATACATTGGGCCCCAGGCGGTCA ATGTGGCAGCCTGAGCCTCCTTTCCATCTCTGTGGAGGCAG ACATAGGACCCCCAACAAACAGCATGCAGGTTGGGAGCCAG |

TABLE 2-continued

Exemplary nucleotide sequences for use in the polynucleotides described herein

| SEQ ID NO. | Description of nucleic acid sequence | Nucleic Acid Sequence |
|---|---|---|
| | | CCACAGGACCCAGGTAAGGGGCCCTGGGTCCTTTTTATGAG GTGGGAGCTGGGCTCTCCCTGATGTATTATTCAGCTCCCTG GAGTTGGCCAGCTCCTGTTACACTGGCCACAGCCCTGGGCA TCCGC |
| 31 | SEQ ID NO: 27 fused to SEQ ID NO: 29 | CTGCAGCTCAGCCTACTACTTGCTTTCCAGGCTGTTCCTAGT TCCCATGTCAGCTGCTTGTGCTTTCCAGAGACAAAACAGGA ATAATAGATGTCATTAAATATACATTGGGCCCCAGGCGGTCA ATGTGGCAGCCTGAGCCTCCTTTCCATCTCTGTGGAGGCAG ACATAGGACCCCCAACAAACAGCATGCAGGTTGGGAGCCAG CCACAGGACCCAGGTAAGGGGCCCTGGGTCCTTTGCCATG GTGACTTTAAAGCCAGGTTGCTGCCCCAGCACAGGCCTCCC AGTCTACCCTCACTAGAAAACAACACCCAGGCACTTTCCACC ACCTCTCAAAGGTGAAACCCAAGGCTGGTCTAGAGAATGAA TTATGGATCCTCGCTGTCCGTGCCACCCAGCTAGTCCCAGC GGCTCAGACACTG |
| 32 | SEQ ID NO: 28 fused to SEQ ID NO: 29 | TTTATGAGGTGGGAGCTGGGCTCTCCCTGATGTATTATTCAG CTCCCTGGAGTTGGCCAGCTCCTGTTACACTGGCCACAGCC CTGGGCATCCGCTGCCATGGTGACTTTAAAGCCAGGTTGCT GCCCCAGCACAGGCCTCCCAGTCTACCCTCACTAGAAAACA ACACCCAGGCACTTTCCACCACCTCTCAAAGGTGAAACCCA AGGCTGGTCTAGAGAATGAATTATGGATCCTCGCTGTCCGT GCCACCCAGCTAGTCCCAGCGGCTCAGACACTG |
| 33 | SEQ ID NO: 28 fused to SEQ ID NO: 27, which is fused to SEQ ID NO: 29 | TTTATGAGGTGGGAGCTGGGCTCTCCCTGATGTATTATTCAG CTCCCTGGAGTTGGCCAGCTCCTGTTACACTGGCCACAGCC CTGGGCATCCGCTGCAGCTCAGCCTACTACTTGCTTTCCA GGCTGTTCCTAGTTCCCATGTCAGCTGCTTGTGCTTTCCAGA GACAAAACAGGAATAATAGATGTCATTAAATATACATTGGGC CCCAGGCGGTCAATGTGGCAGCCTGAGCCTCCTTTCCATCT CTGTGGAGGCAGACATAGGACCCCCAACAAACAGCATGCAG GTTGGGAGCCAGCCACAGGACCCAGGTAAGGGGCCCTGGG TCCTTTGCCATGGTGACTTTAAAGCCAGGTTGCTGCCCCAG CACAGGCCTCCCAGTCTACCCTCACTAGAAAACAACACCCA GGCACTTTCCACCACCTCTCAAAGGTGAAACCCAAGGCTGG TCTAGAGAATGAATTATGGATCCTCGCTGTCCGTGCCACCC AGCTAGTCCCAGCGGCTCAGACACTG |
| 34 | SEQ ID NO: 29 fused to SEQ ID NO: 27, which is fused to SEQ ID NO: 28 | TGCCATGGTGACTTTAAAGCCAGGTTGCTGCCCCAGCACAG GCCTCCCAGTCTACCCTCACTAGAAAACAACACCCAGGCAC TTTCCACCACCTCTCAAAGGTGAAACCCAAGGCTGGTCTAG AGAATGAATTATGGATCCTCGCTGTCCGTGCCACCCAGCTA GTCCCAGCGGCTCAGACACTGCTGCAGCTCAGCCTACTACT TGCTTTCCAGGCTGTTCCTAGTTCCCATGTCAGCTGCTTGTG CTTTCCAGAGACAAAACAGGAATAATAGATGTCATTAAATAT ACATTGGGCCCCAGGCGGTCAATGTGGCAGCCTGAGCCTC CTTTCCATCTCTGTGGAGGCAGACATAGGACCCCCAACAAA CAGCATGCAGGTTGGGAGCCAGCCACAGGACCCAGGTAAG GGGCCCTGGGTCCTTTTTATGAGGTGGGAGCTGGGCTCTCC CTGATGTATTATTCAGCTCCCTGGAGTTGGCCAGCTCCTGTT ACACTGGCCACAGCCCTGGGCATCCGC |
| 35 | SEQ ID NO: 28 fused to SEQ ID NO: 29, which is fused to SEQ ID NO: 27 | TTTATGAGGTGGGAGCTGGGCTCTCCCTGATGTATTATTCAG CTCCCTGGAGTTGGCCAGCTCCTGTTACACTGGCCACAGCC CTGGGCATCCGCTGCCATGGTGACTTTAAAGCCAGGTTGCT GCCCCAGCACAGGCCTCCCAGTCTACCCTCACTAGAAAACA ACACCCAGGCACTTTCCACCACCTCTCAAAGGTGAAACCCA AGGCTGGTCTAGAGAATGAATTATGGATCCTCGCTGTCCGT GCCACCCAGCTAGTCCCAGCGGCTCAGACACTGCTGCAGC TCAGCCTACTACTTGCTTTCCAGGCTGTTCCTAGTTCCCATG TCAGCTGCTTGTGCTTTCCAGAGACAAAACAGGAATAATAGA TGTCATTAAATATACATTGGGCCCCAGGCGGTCAATGTGGC AGCCTGAGCCTCCTTTCCATCTCTGTGGAGGCAGACATAGG ACCCCCAACAAACAGCATGCAGGTTGGGAGCCAGCCACAG GACCCAGGTAAGGGGCCCTGGGTCCTTT |

TABLE 2-continued

Exemplary nucleotide sequences for use in the polynucleotides described herein

| SEQ ID NO. | Description of nucleic acid sequence | Nucleic Acid Sequence |
|---|---|---|
| 36 | Portion of SEQ ID NO: 1 that contains SEQ ID NO: 3 and SEQ ID NO: 4 fused to portion of SEQ ID NO: 2 that contains SEQ ID NO: 8 and SEQ ID NO: 9 | TGCAGCTCAGCCTACTACTTGCTTTCCAGGCTGTTCCTAGTT<br>CCCATGTCAGCTGCTTGTGCTTTCCAGAGACAAAACAGGAA<br>TAATAGATGTCATTAAATATACATTGGGCCCCAGGCGGTCAA<br>TGTGGCAGCCTGAGCCTCCTTTCCATCTCTGTGGAGGCAGA<br>CATAGGACCCCCAACAAACAGCATGCAGGTTGGGAGCCAG<br>CCACAGGACCCAGGTAAGGGGCCCTGGGTCCTTAAGCTTCT<br>GCCACTGGCTCCGGCATTGCAGAGAGAAGAGAAGGGGCGG<br>CAGACTGGAGAGCTGGGCTCCATTTTTGTTCCTTGGTGCCC<br>TGCCCCTCCCCATGACCTGCAGAGACATTCAGCCTGCCAGG<br>CTTTATGAGGTGGGAGCTGGGCTCTCCCTGATGTATTATTCA<br>GCTCCCTGGAGTTGGCCAGCTCCTGTTACACTGGCCACAGC<br>CCTGGGCATCCGCTTCTCACTTCTAGTTTCCCCTCCAAGGTA<br>ATGTGGTGGGTCATGATCATTCTATCCTGGCTTCAGGGACC<br>TGACTCCACTTTGGGGCCATTCGAGGGGTCTAGGGTAGATG<br>ATGTCCCCTGTGGGGATTAATGTCCTGCTCTGTAAAACTGA<br>GCTAGCTGAGATCCAGGAGGGCTTGGCCAGAGACAGCAAG<br>TTGTTGCCATGGTGACTTTAAAGCCAGGTTGCTGCCCCAGC<br>ACAGGCCTCCCAGTCTACCCTCACTAGAAAACAACACCCAG<br>GCACTTTCCACCACCTCTCAAAGGTGAAACCCAAGGCTGGT<br>CTAGAGAATGAATTATGGATCCTCGCTGTCCGTGCCACCCA<br>GCTAGTCCCAGCGGCTCAGACACTGAGGAGAGACTGTAGG<br>TTCAGCTACAAGCAAAAAGACCTAGCTGGTCTCCAAGCAGT<br>GTCTCCAAGTCCCTGAACCTGTGACACCTGCCCCAGGCATC<br>ATCAGGCACAGAGGGCCACC |
| 37 | Portion of SEQ ID NO: 1 that contains SEQ ID NO: 3 and SEQ ID NO: 4 fused to portion of SEQ ID NO: 2 that contains SEQ ID NO: 8 and SEQ ID NO: 9 | TGCAGCTCAGCCTACTACTTGCTTTCCAGGCTGTTCCTAGTT<br>CCCATGTCAGCTGCTTGTGCTTTCCAGAGACAAAACAGGAA<br>TAATAGATGTCATTAAATATACATTGGGCCCCAGGCGGTCAA<br>TGTGGCAGCCTGAGCCTCCTTTCCATCTCTGTGGAGGCAGA<br>CATAGGACCCCCAACAAACAGCATGCAGGTTGGGAGCCAG<br>CCACAGGACCCAGGTAAGGGGCCCTGGGTCCTTTTTATGAG<br>GTGGGAGCTGGGCTCTCCCTGATGTATTATTCAGCTCCCTG<br>GAGTTGGCCAGCTCCTGTTACACTGGCCACAGCCCTGGGCA<br>TCCGCTGCCATGGTGACTTTAAAGCCAGGTTGCTGCCCCAG<br>CACAGGCCTCCCAGTCTACCCTCACTAGAAAACAACACCCA<br>GGCACTTTCCACCACCTCTCAAAGGTGAAACCCAAGGCTGG<br>TCTAGAGAATGAATTATGGATCCTCGCTGTCCGTGCCACCC<br>AGCTAGTCCCAGCGGCTCAGACACTG |

Additional polynucleotides useful in conjunction with the compositions and methods described herein include nucleic acid molecules that have at least 85% sequence identity (e.g., 85%, 90%, 95%, 96%, 97%, 98%, 99%, or more, sequence identity) to the nucleic acid sequences set forth in Table 2 as well as functional portions or derivatives of the nucleic acid sequences set forth in Table 2.

The foregoing polynucleotides can be included in a nucleic acid vector and operably linked to a transgene to express the transgene specifically in hair cells (e.g., cochlear hair cells and/or vestibular hair cells). In some embodiments, the transgene encodes a protein that is implicated in hair cell function, hair cell development, hair cell fate specification, hair cell regeneration, hair cell survival, or hair cell maintenance, or the transgene is the wild-type version of a gene that has been found to be mutated in subjects having hearing loss, deafness, auditory neuropathy, tinnitus, or vestibular dysfunction (e.g., vertigo, dizziness, or loss of balance). According to the methods described herein, a subject can be administered a composition containing one or more of the foregoing polynucleotides (e.g., one or more of the polynucleotides listed in Table 2) operably linked to a transgene encoding a therapeutic protein for the treatment of hearing loss and/or vestibular dysfunction. In some embodiments, the transgene encodes a protein selected from the group consisting of Actin Gamma 1 (ACTG1), Fascin Actin-Bundling Protein 2, Retinal (FSCN2), Radixin (RDX), POU Class 4 Homeobox 3 (POU4F3), TRIO and F-Actin Binding Protein (TRIOBP), Taperin (TPRN), Xin Actin Binding Repeat Containing 2 (XIRP2), Atonal BHLH Transcription Factor 1 (ATOH1), Growth Factor Independent 1 Transcriptional Repressor (GFI1), Cholinergic Receptor Nicotinic Alpha 9 Subunit (CHRNA9), Calcium and Integrin Binding Family Member 3 (CIB3), Cadherin 23 (CDH23), Protocadherin 15 (PCDH15), Kinocilin (KNCN), Pejvakin (DFNB59), Otoferlin (OTOF), MKRN2 Opposite Strand (MKRN2OS), LIM Homeobox Protein 3 (LHX3), Transmembrane Channel Like 1 (TMC1), Myosin 15 (MYO15), Myosin 7A (MYO7A), Myosin 6 (MYO6), Myosin IIIA (MYO3A), Myosin IIIB (MYO3B), Glutaredoxin Domain Containing Cysteine-Rich Protein 1 (GRXCR1), Protein Tyrosine Phosphatase, Receptor Type Q (PTPRQ), Late Cornified Envelope 6A (LCE6A), Lipoxygenase Homology Domain-containing Protein 1 (LOXHD1), ADP-Ribosyl-transferase 1 (ART1), ATPase Plasma Membrane Ca2+ Transporting 2 (ATP2B2), Calcium and Integrin Binding Family Member 2 (CIB2), Calcium Voltage-Gated Channel Auxiliary Subunit Alpha2delta 4(CACNA2D4), Calcium Binding Protein 2 (CABP2), Epidermal Growth Factor Receptor Pathway Substrate 8 (EPS8), EPS8 Like 2 (EPS8L2), Espin (ESPN), Espin Like (ESPNL), Peripherin 2 (PRPH2), Stereocilin (STRC), Solute Carrier Family 8 Member A2 (SLC8A2), Zinc Finger CCHC-Type Containing Protein 12 (ZCCHC12), Leucine Rich Transmembrane and O-methyltransferase Domain Containing (LRTOMT2, LRTOMT1), USH1 Protein Network Component Harmonin (USH1 C), Extracellular Leucine Rich Repeat and Fibronectin Type III Domain Containing 1 (ELFN1), Tetratricopeptide Repeat Protein 24 (TTC24), Dystrotelin (DYTN), Kielin/Chordin-Like Protein (KCP), Coiled-coil Glutamate Rich Protein 2 (CCER2), Leucine-rich Repeat and Transmembrane Domain-containing protein 2 (LRTM2), Potassium Voltage-Gated Channel Subfamily A Member 10 (KCNA10), Neurotrophin 3 (NTF3), Clarin 1 (CLRN1), Clarin 2 (CLRN2), SKI Family Transcriptional Corepressor 1 (SKOR1), Tctex1 Domain Containing Protein 1 (TCTEX1 D1), Fc Receptor Like B (FCRLB), Solute Carrier Family 17 Member 8 (SLC17A8), Glutaredoxin Domain Containing Cysteine-Rich Protein 2 (GRXCR2), Brain-derived Neurotrophic Factor (BDNF), Serpin Family E Member 3 (SERPINE3), Nescient Helix-loop Helix 1 (NHLH1), Heat Shock Protein 70 (HSP70), Heat Shock Protein 90 (HSP90), Activating Transcription Factor 6 (ATF6), Eukaryotic Translation Initiation Factor 2 Alpha Kinase 3 (PERK), Serine/Threonine-Protein Kinase/Endoribonuclease IRE1 (IRE1), and Binding Immunoglobulin Protein (BIP).

Expression of Exogenous Nucleic Acids in Mammalian Cells

Mutations in a variety of genes, such as MYO7A, POU4F3, SLC17A8, and TMC1, have been linked to sensorineural hearing loss, and some of these mutations, such as mutations in MYO7A, are also associated with vestibular dysfunction. The compositions and methods described herein can be used to induce or increase the expression of proteins encoded by genes of interest (e.g., the wild-type form of genes implicated in hearing loss and/or vestibular dysfunction, or genes involved in hair cell development, function, cell fate specification, regeneration, survival, or maintenance) specifically in hair cells (e.g., cochlear and/or vestibular hair cells) by administering a nucleic acid vector that contains a Myo15 promoter (e.g., a polynucleotide that contains a first region having at least 85% sequence identity (e.g., 85%, 90%, 95%, 96%, 97%, 98%, 99%, or more, sequence identity) to SEQ ID NO: 1 or a functional portion or derivative thereof and/or a second region having at least 85% sequence identity (e.g., 85%, 90%, 95%, 96%, 97%, 98%, 99%, or more, sequence identity) to SEQ ID NO: 2 or a functional portion or derivative thereof, optionally containing a linker joining the first region and the second region) operably linked to a nucleic acid sequence that encodes a protein of interest. A wide array of methods has been established for the delivery of proteins to mammalian cells and for the stable expression of genes encoding proteins in mammalian cells.

Proteins that can be expressed in connection with the compositions described herein (e.g., when the transgene encoding the protein is operably linked to a polynucleotide that contains a first region having at least 85% sequence identity (e.g., 85%, 90%, 95%, 96%, 97%, 98%, 99%, or more, sequence identity) to SEQ ID NO: 1 or a functional portion or derivative thereof and/or a second region having at least 85% sequence identity (e.g., 85%, 90%, 95%, 96%, 97%, 98%, 99%, or more, sequence identity) to SEQ ID NO: 2 or a functional portion or derivative thereof) are proteins that are expressed in healthy hair cells (e.g., cochlear and/or vestibular hair cells, e.g., proteins that play a role in hair cell development, function, regeneration, cell fate specification, survival, or maintenance, or proteins that are deficient in subjects with sensorineural hearing loss or vestibular dysfunction) or other therapeutic proteins of interest. Proteins that can be expressed in hair cells using the compositions and methods described herein include ACTG1, FSCN2, RDX, POU4F3, TRIOBP, TPRN, XIRP2, ATOH1, GFI1, CHRNA9, CIB3, CDH23, PCDH15, KNCN, DFNB59, OTOF, MKRN2OS, LHX3, TMC1, MYO15, MYO7A, MYO6, MYO3A, MYO3B, GRXCR1, PTPRQ, LCE6A, LOXHD1, ART1, ATP2B2, CIB2, CACNA2D4, CABP2, EPS8, EPS8L2, ESPN, ESPNL, PRPH2, STRC, SLC8A2, ZCCHC12, LRTOMT2, LRTOMT1, USH1C, ELFN1, TTC24, DYTN, KCP, CCER2, LRTM2, KCNA10, NTF3, CLRN1, CLRN2, SKOR1, TCTEX1 D1, FCRLB, SLC17A8, GRXCR2, BDNF, SERPINE3, NHLH1, HSP70, HSP90, ATF6, PERK, IRE1, and BIP.

Polynucleotides Encoding Proteins of Interest

One platform that can be used to achieve therapeutically effective intracellular concentrations of proteins of interest in mammalian cells is via the stable expression of the gene encoding the protein of interest (e.g., by integration into the nuclear or mitochondrial genome of a mammalian cell, or by episomal concatemer formation in the nucleus of a mammalian cell). The gene is a polynucleotide that encodes the primary amino acid sequence of the corresponding protein. In order to introduce exogenous genes into a mammalian cell, genes can be incorporated into a vector. Vectors can be introduced into a cell by a variety of methods, including transformation, transfection, transduction, direct uptake, projectile bombardment, and by encapsulation of the vector in a liposome. Examples of suitable methods of transfecting or transforming cells include calcium phosphate precipitation, electroporation, microinjection, infection, lipofection and direct uptake. Such methods are described in more detail, for example, in Green, et al., Molecular Cloning: A Laboratory Manual, Fourth Edition (Cold Spring Harbor University Press, New York 2014); and Ausubel, et al., Current Protocols in Molecular Biology (John Wiley & Sons, New York 2015), the disclosures of each of which are incorporated herein by reference.

Proteins of interest can also be introduced into a mammalian cell by targeting a vector containing a gene encoding a protein of interest to cell membrane phospholipids. For example, vectors can be targeted to the phospholipids on the extracellular surface of the cell membrane by linking the vector molecule to a VSV-G protein, a viral protein with affinity for all cell membrane phospholipids. Such a construct can be produced using methods well known to those of skill in the field.

Recognition and binding of the polynucleotide encoding a protein of interest by mammalian RNA polymerase is important for gene expression. As such, one may include sequence elements within the polynucleotide that exhibit a high affinity for transcription factors that recruit RNA polymerase and promote the assembly of the transcription complex at the transcription initiation site. Such sequence elements include, e.g., a mammalian promoter, the sequence of which can be recognized and bound by specific transcription initiation factors and ultimately RNA polymerase. Examples of mammalian promoters have been described in Smith, et al., Mol. Sys. Biol., 3:73, online publication, the disclosure of which is incorporated herein by reference. The promoter used in the methods and compositions described herein is a polynucleotide that contains first region having at least 85% sequence identity (e.g., 85%, 90%, 95%, 96%, 97%, 98%, 99%, or more, sequence identity) to SEQ ID NO: 1 or a functional portion or derivative thereof and/or a second region having at least 85% sequence identity (e.g., 85%, 90%, 95%, 96%, 97%, 98%, 99%, or more, sequence identity) to SEQ ID NO: 2 or a functional portion or derivative thereof, that optionally contains a linker between the first region and the second region.

Once a polynucleotide encoding a protein of interest has been incorporated into the nuclear DNA of a mammalian cell, the transcription of this polynucleotide can be induced by methods known in the art. For example, expression can be induced by exposing the mammalian cell to an external chemical reagent, such as an agent that modulates the binding of a transcription factor and/or RNA polymerase to the mammalian promoter and thus regulates gene expression. The chemical reagent can serve to facilitate the binding of RNA polymerase and/or transcription factors to the mammalian promoter, e.g., by removing a repressor protein that has bound the promoter. Alternatively, the chemical reagent can serve to enhance the affinity of the mammalian promoter for RNA polymerase and/or transcription factors such that the rate of transcription of the gene located downstream of the promoter is increased in the presence of the chemical reagent. Examples of chemical reagents that potentiate polynucleotide transcription by the above mechanisms include tetracycline and doxycycline. These reagents are commercially available (Life Technologies, Carlsbad, CA) and can be administered to a mammalian cell in order to promote gene expression according to established protocols.

Other DNA sequence elements that may be included in polynucleotides for use in the compositions and methods described herein include enhancer sequences. Enhancers represent another class of regulatory elements that induce a conformational change in the polynucleotide comprising the gene of interest such that the DNA adopts a three-dimensional orientation that is favorable for binding of transcription factors and RNA polymerase at the transcription initiation site. Thus, polynucleotides for use in the compositions and methods described herein include those that encode a protein of interest and additionally include a mammalian enhancer sequence. Many enhancer sequences are now known from mammalian genes, and examples include enhancers from the genes that encode mammalian globin, elastase, albumin, α-fetoprotein, and insulin. Enhancers for use in the compositions and methods described herein also include those that are derived from the genetic material of a virus capable of infecting a eukaryotic cell. Examples include the SV40 enhancer on the late side of the replication origin (bp 100-270), the cytomegalovirus early promoter enhancer, the polyoma enhancer on the late side of the replication origin, and adenovirus enhancers. Additional enhancer sequences that induce activation of eukaryotic gene transcription include the CMV enhancer and RSV enhancer. An enhancer may be spliced into a vector containing a polynucleotide encoding a protein of interest, for example, at a position 5' or 3' to this gene. In a preferred orientation, the enhancer is positioned at the 5' side of the promoter, which in turn is located 5' relative to the polynucleotide encoding a protein of interest.

The nucleic acid vectors containing a Myo15 promoter described herein may include a Woodchuck Posttranscriptional Regulatory Element (WPRE). The WPRE acts at the transcriptional level, by promoting nuclear export of transcripts and/or by increasing the efficiency of polyadenylation of the nascent transcript, thus increasing the total amount of mRNA in the cell. The addition of the WPRE to a vector can result in a substantial improvement in the level of transgene expression from several different promoters, both in vitro and in vivo.

In some embodiments, the nucleic acid vectors containing a Myo15 promoter described herein include a reporter sequence, which can be useful in verifying the expression of a gene operably linked to a Myo15 promoter, for example, in cells and tissues (e.g., in hair cells, such as cochlear and/or vestibular hair cells). Reporter sequences that may be provided in a transgene include DNA sequences encoding β-lactamase, β-galactosidase (LacZ), alkaline phosphatase, thymidine kinase, green fluorescent protein (GFP), chloramphenicol acetyltransferase (CAT), luciferase, and others well known in the art. When associated with regulatory elements that drive their expression, such as a Myo15 promoter, the reporter sequences provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA), and immunohistochemistry. For example, where the marker sequence is the LacZ gene, the presence of the vector carrying the signal is detected by assays for β-galactosidase activity. Where the transgene is green fluorescent protein or luciferase, the vector carrying the signal may be measured visually by color or light production in a luminometer.

Methods for the Delivery of Exogenous Nucleic Acids to Target Cells

Techniques that can be used to introduce a transgene, such as a transgene operably linked to a Myo15 promoter described herein, into a target cell (e.g., a mammalian cell) are well known in the art. For instance, electroporation can be used to permeabilize mammalian cells (e.g., human target cells) by the application of an electrostatic potential to the cell of interest. Mammalian cells, such as human cells, subjected to an external electric field in this manner are subsequently predisposed to the uptake of exogenous nucleic acids. Electroporation of mammalian cells is described in detail, e.g., in Chu et al., Nucleic Acids Research 15:1311 (1987), the disclosure of which is incorporated herein by reference. A similar technique, Nucleofection™, utilizes an applied electric field in order to stimulate the uptake of exogenous polynucleotides into the nucleus of a eukaryotic cell. Nucleofection™ and protocols useful for performing this technique are described in detail, e.g., in Distler et al., Experimental Dermatology 14:315 (2005), as well as in US 2010/0317114, the disclosures of each of which are incorporated herein by reference.

Additional techniques useful for the transfection of target cells include the squeeze-poration methodology. This technique induces the rapid mechanical deformation of cells in order to stimulate the uptake of exogenous DNA through membranous pores that form in response to the applied stress. This technology is advantageous in that a vector is not required for delivery of nucleic acids into a cell, such as a human target cell. Squeeze-poration is described in detail, e.g., in Sharei et al., Journal of Visualized Experiments 81:e50980 (2013), the disclosure of which is incorporated herein by reference.

Lipofection represents another technique useful for transfection of target cells. This method involves the loading of nucleic acids into a liposome, which often presents cationic functional groups, such as quaternary or protonated amines, towards the liposome exterior. This promotes electrostatic interactions between the liposome and a cell due to the anionic nature of the cell membrane, which ultimately leads to uptake of the exogenous nucleic acids, for instance, by direct fusion of the liposome with the cell membrane or by endocytosis of the complex. Lipofection is described in detail, for instance, in U.S. Pat. No. 7,442,386, the disclosure of which is incorporated herein by reference. Similar techniques that exploit ionic interactions with the cell membrane to provoke the uptake of foreign nucleic acids include contacting a cell with a cationic polymer-nucleic acid complex. Exemplary cationic molecules that associate with polynucleotides so as to impart a positive charge favorable for interaction with the cell membrane include activated dendrimers (described, e.g., in Dennig, Topics in Current Chemistry 228:227 (2003), the disclosure of which is incorporated herein by reference) polyethylenimine, and diethylaminoethyl (DEAE)-dextran, the use of which as a transfection agent is described in detail, for instance, in Gulick et al., Current Protocols in Molecular Biology 40:1:9.2:9.2.1 (1997), the disclosure of which is incorporated herein by reference. Magnetic beads are another tool that can be used to transfect target cells in a mild and efficient manner, as this methodology utilizes an applied magnetic field in order to direct the uptake of nucleic acids. This technology is described in detail, for instance, in US 2010/0227406, the disclosure of which is incorporated herein by reference.

Another useful tool for inducing the uptake of exogenous nucleic acids by target cells is laserfection, also called optical transfection, a technique that involves exposing a cell to electromagnetic radiation of a particular wavelength in order to gently permeabilize the cells and allow polynucleotides to penetrate the cell membrane. The bioactivity of this technique is similar to, and in some cases found superior to, electroporation.

Impalefection is another technique that can be used to deliver genetic material to target cells. It relies on the use of nanomaterials, such as carbon nanofibers, carbon nanotubes, and nanowires. Needle-like nanostructures are synthesized perpendicular to the surface of a substrate. DNA containing the gene, intended for intracellular delivery, is attached to the nanostructure surface. A chip with arrays of these needles is then pressed against cells or tissue. Cells that are impaled by nanostructures can express the delivered gene(s). An example of this technique is described in Shalek et al., PNAS 107: 1870 (2010), the disclosure of which is incorporated herein by reference.

Magnetofection can also be used to deliver nucleic acids to target cells. The magnetofection principle is to associate nucleic acids with cationic magnetic nanoparticles. The magnetic nanoparticles are made of iron oxide, which is fully biodegradable, and coated with specific cationic proprietary molecules varying upon the applications. Their association with the gene vectors (DNA, siRNA, viral vector, etc.) is achieved by salt-induced colloidal aggregation and electrostatic interaction. The magnetic particles are then concentrated on the target cells by the influence of an external magnetic field generated by magnets. This technique is described in detail in Scherer et al., Gene Therapy 9:102 (2002), the disclosure of which is incorporated herein by reference.

Another useful tool for inducing the uptake of exogenous nucleic acids by target cells is sonoporation, a technique that involves the use of sound (typically ultrasonic frequencies) for modifying the permeability of the cell plasma membrane permeabilize the cells and allow polynucleotides to penetrate the cell membrane. This technique is described in detail, e.g., in Rhodes et al., Methods in Cell Biology 82:309 (2007), the disclosure of which is incorporated herein by reference.

Microvesicles represent another potential vehicle that can be used to modify the genome of a target cell according to the methods described herein. For instance, microvesicles that have been induced by the co-overexpression of the glycoprotein VSV-G with, e.g., a genome-modifying protein, such as a nuclease, can be used to efficiently deliver proteins into a cell that subsequently catalyze the site-specific cleavage of an endogenous polynucleotide sequence so as to prepare the genome of the cell for the covalent incorporation of a polynucleotide of interest, such as a gene or regulatory sequence. The use of such vesicles, also referred to as Gesicles, for the genetic modification of eukaryotic cells is described in detail, e.g., in Quinn et al., Genetic Modification of Target Cells by Direct Delivery of Active Protein [abstract]. In: Methylation changes in early embryonic genes in cancer [abstract], in: Proceedings of the 18th Annual Meeting of the American Society of Gene and Cell Therapy; 2015 May 13, Abstract No. 122.

Vectors for Delivery of Exogenous Nucleic Acids to Target Cells

In addition to achieving high rates of transcription and translation, stable expression of an exogenous gene in a mammalian cell can be achieved by integration of the polynucleotide comprising the gene into the nuclear genome of the mammalian cell. A variety of vectors for the delivery and integration of polynucleotides encoding exogenous proteins into the nuclear DNA of a mammalian cell have been developed. Examples of expression vectors are described in, e.g., Gellissen, Production of Recombinant Proteins: Novel Microbial and Eukaryotic Expression Systems (John Wiley & Sons, Marblehead, MA, 2006). Expression vectors for use in the compositions and methods described herein contain a Myo15 promoter (e.g., a polynucleotide that contains first region having at least 85% sequence identity (e.g., 85%, 90%, 95%, 96%, 97%, 98%, 99%, or more, sequence identity) to SEQ ID NO: 1 or a functional portion or derivative thereof and/or a second region having at least 85% sequence identity (e.g., 85%, 90%, 95%, 96%, 97%, 98%, 99%, or more, sequence identity) to SEQ ID NO: 2 or a functional portion or derivative thereof, that optionally contains a linker between the first region and the second region) operably linked to a polynucleotide sequence that encodes a protein of interest, as well as, e.g., additional sequence elements used for the expression of these agents and/or the integration of these polynucleotide sequences into the genome of a mammalian cell. Vectors that can contain a Myo15 promoter operably linked to a transgene encoding a protein of interest include plasmids (e.g., circular DNA molecules that can autonomously replicate inside a cell), cosmids (e.g., pWE or sCos vectors), artificial chromosomes (e.g., a human artificial chromosome (HAC), a yeast artificial chromosome (YAC), a bacterial artificial chromosome (BAC), or a P1-derived artificial chromosome (PAC)), and viral vectors. Certain vectors that can be used for the expression of a protein of interest include plasmids that contain regulatory sequences, such as enhancer regions, which direct gene transcription. Other useful vectors for expression of a protein of interest contain polynucleotide sequences that enhance the rate of translation of these genes or improve the stability or nuclear export of the mRNA that results from gene transcription. These sequence elements include, e.g., 5' and 3' untranslated regions, an internal ribosomal entry site (IRES), and polyadenylation signal site in order to direct efficient transcription of the gene carried on the expression vector. The expression vectors suitable for use with the compositions and methods described herein may also contain a polynucleotide encoding a marker for selection of cells that contain such a vector. Examples of a suitable marker include genes that encode resistance to antibiotics, such as ampicillin, chloramphenicol, kanamycin, or nourseothricin.

Viral Vectors for Nucleic Acid Delivery

Viral genomes provide a rich source of vectors that can be used for the efficient delivery of a gene of interest into the genome of a target cell (e.g., a mammalian cell, such as a human cell). Viral genomes are particularly useful vectors for gene delivery because the polynucleotides contained within such genomes are typically incorporated into the nuclear genome of a mammalian cell by generalized or specialized transduction. These processes occur as part of the natural viral replication cycle, and do not require added proteins or reagents in order to induce gene integration. Examples of viral vectors include a retrovirus (e.g., Retroviridae family viral vector), adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, modified vaccinia Ankara (MVA), fowlpox and canarypox). Other viruses include Norwalk virus, togavirus, flavivirus, reoviruses, papovavirus, hepadnavirus, human papilloma virus, human foamy virus, and hepatitis virus, for example. Examples of retroviruses include: avian leukosis-sarcoma, avian C-type viruses, mammalian C-type, B-type viruses, D-type viruses, oncoretroviruses, HTLV-BLV group, lentivirus, alpharetrovirus, gammaretrovirus, spumavirus (Coffin, J. M., Retroviridae: The viruses and their replication, Virology, Third Edition (Lippincott-Raven, Philadelphia, 1996)). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, U.S. Pat. No. 5,801,030, the disclosure of which is incorporated herein by reference as it pertains to viral vectors for use in gene therapy.

AAV Vectors for Nucleic Acid Delivery

In some embodiments, polynucleotides of the compositions and methods described herein are incorporated into rAAV vectors and/or virions in order to facilitate their introduction into a cell. rAAV vectors useful in the compositions and methods described herein are recombinant nucleic acid constructs that include (1) a Myo15 promoter described herein (e.g., a polynucleotide that contains first region having at least 85% sequence identity (e.g., 85%, 90%, 95%, 96%, 97%, 98%, 99%, or more, sequence identity) to SEQ ID NO: 1 or a functional portion or derivative thereof and/or a second region having at least 85% sequence identity (e.g., 85%, 90%, 95%, 96%, 97%, 98%, 99%, or more, sequence identity) to SEQ ID NO: 2 or a functional portion or derivative thereof, that optionally contains a linker between the first region and the second region), (2) a heterologous sequence to be expressed, and (3) viral sequences that facilitate stability and expression of the heterologous genes. The viral sequences may include those sequences of AAV that are required in cis for replication and packaging (e.g., functional ITRs) of the DNA into a virion. In typical applications, the transgene encodes a therapeutic protein that can promote hair cell development, hair cell function, hair cell regeneration, hair cell fate specification, hair cell survival, or hair cell maintenance, or a wild-type form of a hair cell protein that is mutated in subjects with forms of hereditary hearing loss or vestibular dysfunction that may be useful for improving hearing or vestibular function in subjects carrying mutations that have been associated with hearing loss, deafness, or vestibular dysfunction (e.g., dizziness, vertigo, or imbalance). Such rAAV vectors may also contain marker or reporter genes. Useful rAAV vectors have one or more of the AAV WT genes deleted in whole or in part, but retain functional flanking ITR sequences. The AAV ITRs may be of any serotype suitable for a particular application. For use in the methods and compositions described herein, the ITRs can be AAV2 ITRs. Methods for using rAAV vectors are described, for example, in Tal et al., J. Biomed. Sci. 7:279 (2000), and Monahan and Samulski, Gene Delivery 7:24 (2000), the disclosures of each of which are incorporated herein by reference as they pertain to AAV vectors for gene delivery.

The polynucleotides and vectors described herein (e.g., a Myo15 promoter operably linked to a transgene encoding a protein of interest) can be incorporated into a rAAV virion in order to facilitate introduction of the polynucleotide or vector into a cell. The capsid proteins of AAV compose the exterior, non-nucleic acid portion of the virion and are encoded by the AAV cap gene. The cap gene encodes three viral coat proteins, VP1, VP2 and VP3, which are required for virion assembly. The construction of rAAV virions has been described, for instance, in U.S. Pat. Nos. 5,173,414; 5,139,941; 5,863,541; 5,869,305; 6,057,152; and 6,376,237; as well as in Rabinowitz et al., J. Virol. 76:791 (2002) and Bowles et al., J. Virol. 77:423 (2003), the disclosures of each of which are incorporated herein by reference as they pertain to AAV vectors for gene delivery.

rAAV virions useful in conjunction with the compositions and methods described herein include those derived from a variety of AAV serotypes including AAV 1, 2, 3, 4, 5, 6, 7, 8, 9, 10, rh10, rh39, rh43, rh74, Anc80, Anc80L65, DJ/8, DJ/9, 7m8, PHP.B, PHP.eb, and PHP.S. For targeting hair cells, AAV1, AAV2, AAV2quad(Y-F), AAV6, AAV9, Anc80, Anc80L65, DJ/9, 7m8, and PHP.B may be particularly useful. Serotypes evolved for transduction of the retina may also be used in the methods and compositions described herein. Construction and use of AAV vectors and AAV proteins of different serotypes are described, for instance, in Chao et al., Mol. Ther. 2:619 (2000); Davidson et al., Proc. Natl. Acad. Sci. USA 97:3428 (2000); Xiao et al., J. Virol. 72:2224 (1998); Halbert et al., J. Virol. 74:1524 (2000); Halbert et al., J. Virol. 75:6615 (2001); and Auricchio et al., Hum. Molec. Genet. 10:3075 (2001), the disclosures of each of which are incorporated herein by reference as they pertain to AAV vectors for gene delivery.

Also useful in conjunction with the compositions and methods described herein are pseudotyped rAAV vectors. Pseudotyped vectors include AAV vectors of a given serotype (e.g., AAV9) pseudotyped with a capsid gene derived from a serotype other than the given serotype (e.g., AAV1, AAV2, AAV3, AAV4, AAV5, AAV6, AAV7, AAV8, etc.). Techniques involving the construction and use of pseudotyped rAAV virions are known in the art and are described, for instance, in Duan et al., J. Virol. 75:7662 (2001); Halbert et al., J. Virol. 74:1524 (2000); Zolotukhin et al., Methods, 28:158 (2002); and Auricchio et al., Hum. Molec. Genet. 10:3075 (2001).

AAV virions that have mutations within the virion capsid may be used to infect particular cell types more effectively than non-mutated capsid virions. For example, suitable AAV mutants may have ligand insertion mutations for the facilitation of targeting AAV to specific cell types. The construction and characterization of AAV capsid mutants including insertion mutants, alanine screening mutants, and epitope tag mutants is described in Wu et al., J. Virol. 74:8635 (2000). Other rAAV virions that can be used in methods described herein include those capsid hybrids that are generated by molecular breeding of viruses as well as by exon shuffling. See, e.g., Soong et al., Nat. Genet., 25:436 (2000) and Kolman and Stemmer, Nat. Biotechnol. 19:423 (2001).

Pharmaceutical Compositions

The polynucleotides described herein (e.g., a polynucleotide that contains first region having at least 85% sequence identity (e.g., 85%, 90%, 95%, 96%, 97%, 98%, 99%, or more, sequence identity) to SEQ ID NO: 1 or a functional portion or derivative thereof and/or a second region having at least 85% sequence identity (e.g., 85%, 90%, 95%, 96%, 97%, 98%, 99%, or more, sequence identity) to SEQ ID NO: 2 or a functional portion or derivative thereof, that optionally contains a linker between the first region and the second region) may be operably linked to a transgene (e.g., a transgene encoding a protein of interest) and incorporated into a vehicle for administration into a patient, such as a human patient suffering from sensorineural hearing loss and/or vestibular dysfunction. Pharmaceutical compositions containing vectors, such as viral vectors, that contain a polynucleotide described herein operably linked to a therapeutic transgene can be prepared using methods known in the art. For example, such compositions can be prepared using, e.g., physiologically acceptable carriers, excipients or stabilizers (Remington: The Science and Practice of Pharmacology 22nd edition, Allen, L. Ed. (2013); incorporated herein by reference), and in a desired form, e.g., in the form of lyophilized formulations or aqueous solutions.

Mixtures of nucleic acid vectors (e.g., viral vectors) containing a polynucleotide described herein (e.g., a polynucleotide that contains first region having at least 85% sequence identity (e.g., 85%, 90%, 95%, 96%, 97%, 98%, 99%, or more, sequence identity) to SEQ ID NO: 1 or a functional portion or derivative thereof and/or a second region having at least 85% sequence identity (e.g., 85%, 90%, 95%, 96%, 97%, 98%, 99%, or more, sequence identity) to SEQ ID NO: 2 or a functional portion or derivative thereof, that optionally contains a linker between the first region and the second region) operably linked to a therapeutic transgene may be prepared in water suitably mixed with one or more excipients, carriers, or diluents. Dispersions may also be prepared in glycerol, liquid polyethylene glycols, and mixtures thereof and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (described in U.S. Pat. No. 5,466,468, the disclosure of which is incorporated herein by reference). In any case the formulation may be sterile and may be fluid to the extent that easy syringability exists. Formulations may be stable under the conditions of manufacture and storage and may be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For example, a solution containing a pharmaceutical composition described herein may be suitably buffered, if necessary, and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion. Some variation in dosage will necessarily occur depending on the condition of the subject being treated. For local administration to the inner ear, the composition may be formulated to contain a synthetic perilymph solution. An exemplary synthetic perilymph solution includes 20-200 mM NaCl, 1-5 mM KCl, 0.1-10 mM $CaCl_2$), 1-10 mM glucose, and 2-50 mM HEPEs, with a pH between about 6 and 9 and an osmolality of about 300 mOsm/kg. The person responsible for administration will, in any event, determine the appropriate dose for the individual subject. Moreover, for human administration, preparations may meet sterility, pyrogenicity, general safety, and purity standards as required by FDA Office of Biologics standards.

Methods of Treatment

The compositions described herein may be administered to a subject with sensorineural hearing loss and/or vestibular dysfunction by a variety of routes, such as local administration to the inner ear (e.g., administration into the perilymph or endolymph, e.g., through the oval window, round window, or a semicircular canal (e.g., the horizontal canal), e.g., administration to a cochlear or vestibular hair cell), intravenous, parenteral, intradermal, transdermal, intramuscular, intranasal, subcutaneous, percutaneous, intratracheal, intraperitoneal, intraarterial, intravascular, inhalation, perfusion, lavage, and oral administration. The most suitable route for administration in any given case will depend on the particular composition administered, the patient, pharmaceutical formulation methods, administration methods (e.g., administration time and administration route), the patients age, body weight, sex, severity of the disease being treated, the patient's diet, and the patient's excretion rate. Compositions may be administered once, or more than once (e.g., once annually, twice annually, three times annually, bi-monthly, or monthly).

Subjects that may be treated as described herein are subjects having or at risk of developing sensorineural hearing loss and/or vestibular dysfunction (e.g., subjects having or at risk of developing hearing loss, vestibular dysfunction, or both). The compositions and methods described herein can be used to treat subjects having or at risk of developing damage to cochlear hair cells (e.g., damage related to acoustic trauma, disease or infection, head trauma, ototoxic drugs, or aging), subjects having or at risk of developing damage to vestibular hair cells (e.g., damage related to disease or infection, head trauma, ototoxic drugs, or aging), subjects having or at risk of developing sensorineural hearing loss, deafness, or auditory neuropathy, subjects having or at risk of developing vestibular dysfunction (e.g., dizziness, vertigo, or imbalance), subjects having tinnitus (e.g., tinnitus alone, or tinnitus that is associated with sensorineural hearing loss or vestibular dysfunction), subjects having a genetic mutation associated with hearing loss and/or vestibular dysfunction, or subjects with a family history of hereditary hearing loss, deafness, auditory neuropathy, tinnitus, or vestibular dysfunction. In some embodiments, the subject has hearing loss and/or vestibular dysfunction that is associated with or results from loss of hair cells (e.g., cochlear or vestibular hair cells). The methods described herein may include a step of screening a subject for mutations in genes known to be associated with hearing loss or vestibular dysfunction prior to treatment with or administration of the compositions described herein. A subject can be screened for a genetic mutation using standard methods known to those of skill in the art (e.g., genetic testing). The methods described herein may also include a step of assessing hearing and/or vestibular function in a subject prior to treatment with or administration of the compositions described herein. Hearing can be assessed using standard tests, such as audiometry, auditory brainstem response (ABR), electrocochleography (ECOG), and otoacoustic emissions. Vestibular function may be assessed using standard tests, such as eye movement testing (e.g., electronystagmogram (ENG) or videonystagmogram (VNG)), posturography, rotary-chair testing, ECOG, vestibular evoked myogenic potentials (VEMP), and specialized clinical balance tests, such as those described in Mancini and Horak, Eur J Phys Rehabil Med, 46:239 (2010). The compositions and methods described herein may also be administered as a preventative treatment to patients at risk of developing hearing loss and/or vestibular dysfunction, e.g., patients who have a family history of hearing loss or vestibular dysfunction (e.g., inherited hearing loss or vestibular dysfunction), patients carrying a genetic mutation associated with hearing loss or vestibular dysfunction who do not yet exhibit hearing impairment or vestibular dysfunction or patients exposed to risk factors for acquired hearing loss (e.g., disease or infection, head trauma, ototoxic drugs, or aging) or vestibular dysfunction (e.g., acoustic trauma, disease or infection, head trauma, ototoxic drugs, or aging).

The compositions and methods described herein can be used to promote or induce hair cell regeneration in a subject (e.g., cochlear and/or vestibular hair cell regeneration). Subjects that may benefit from compositions that promote or induce hair cell regeneration include subjects suffering from hearing loss or vestibular dysfunction as a result of loss of hair cells (e.g., loss of hair cells related to trauma (e.g., acoustic trauma or head trauma), disease or infection, ototoxic drugs, or aging), and subjects with abnormal hair cells (e.g., hair cells that do not function properly when compared to normal hair cells), damaged hair cells (e.g., hair cell damage related to trauma (e.g., acoustic trauma or head trauma), disease or infection, ototoxic drugs, or aging), or reduced hair cell numbers due to genetic mutations or congenital abnormalities. The compositions and methods described herein can also be used to promote or increase hair cell survival (e.g., increase survival of damaged hair cells, promote repair of damaged hair cells, or preserve hair cells in a subject at risk of loss of hair cells (e.g., loss of hair cells due to age, exposure to loud noise, disease or infection, head trauma or ototoxic drugs)).

The compositions and methods described herein can also be used to prevent or reduce ototoxic drug-induced hair cell damage or death (e.g., cochlear and/or vestibular hair cell damage or death) in subjects who have been treated with ototoxic drugs, or who are currently undergoing or soon to begin treatment with ototoxic drugs. Ototoxic drugs are toxic to the cells of the inner ear, and can cause sensorineural hearing loss, vestibular dysfunction (e.g., vertigo, dizziness, or imbalance), tinnitus, or a combination of these symptoms. Drugs that have been found to be ototoxic include aminoglycoside antibiotics (e.g., gentamycin, neomycin, streptomycin, tobramycin, kanamycin, vancomycin, and amikacin), viomycin, antineoplastic drugs (e.g., platinum-containing chemotherapeutic agents, such as cisplatin, carboplatin, and oxaliplatin), loop diuretics (e.g., ethacrynic acid and furosemide), salicylates (e.g., aspirin, particularly at high doses), and quinine. In some embodiments, the methods described herein prevent or reduce hair cell damage or death related to acoustic trauma, disease or infection, head trauma, or aging.

The transgene operably linked to a Myo15 promoter (e.g., a polynucleotide that contains a first region having at least 85% sequence identity (e.g., 85%, 90%, 95%, 96%, 97%, 98%, 99%, or more, sequence identity) to SEQ ID NO: 1 or a functional portion or derivative thereof and/or a second region having at least 85% sequence identity (e.g., 85%, 90%, 95%, 96%, 97%, 98%, 99%, or more, sequence identity) to SEQ ID NO: 2 or a functional portion or derivative thereof) for treatment of a subject as described herein can be a transgene that encodes a protein expressed in healthy hair cells (e.g., cochlear and/or vestibular hair cells, e.g., a protein that plays a role in hair cell development, function, cell fate specification, regeneration, survival, or maintenance, or a protein that is deficient in a subject with sensorineural hearing loss and/or vestibular dysfunction) or another therapeutic protein of interest. The transgene may be selected based on the cause of the subject's hearing loss or vestibular dysfunction (e.g., if the subject's hearing loss or vestibular dysfunction is associated with a particular genetic mutation, the transgene can be a wild-type form of the gene that is mutated in the subject, or if the subject has hearing loss associated with loss of hair cells, the transgene can encode a protein that promotes hair cell regeneration), the severity of the subject's hearing loss or vestibular dysfunction, the health of the subject's hair cells, the subject's age, the subject's family history of hearing loss or vestibular dysfunction, or other factors. The proteins that may be expressed by a transgene operably linked to a Myo15 promoter for treatment of a subject as described herein include ACTG1, FSCN2, RDX, POU4F3, TRIOBP, TPRN, XIRP2, ATOH1, GFI1, CHRNA9, CIB3, CDH23, PCDH15, KNCN, DFNB59, OTOF, MKRN2OS, LHX3, TMC1, MYO15, MYO7A, MYO6, MYO3A, MYO3B, GRXCR1, PTPRQ, LCE6A, LOXHD1, ART1, ATP2B2, CIB2, CACNA2D4, CABP2, EPS8, EPS8L2, ESPN, ESPNL, PRPH2, STRC, SLC8A2, ZCCHC12, LRTOMT2, LRTOMT1, USH1C, ELFN1, TTC24, DYTN, KCP, CCER2, LRTM2, KCNA10, NTF3, CLRN1, CLRN2, SKOR1, TCTEX1 D1, FCRLB, SLC17A8, GRXCR2, BDNF, SERPINE3, NHLH1, HSP70, HSP90, ATF6, PERK, IRE1, and BIP.

Treatment may include administration of a composition containing the nucleic acid vectors (e.g., AAV viral vectors) containing a Myo15 promoter described herein in various unit doses. Each unit dose will ordinarily contain a predetermined-quantity of the therapeutic composition. The quantity to be administered, and the particular route of administration and formulation, are within the skill of those in the clinical arts. A unit dose need not be administered as a single injection but may comprise continuous infusion over a set period of time. Dosing may be performed using a syringe pump to control infusion rate in order to minimize damage to the inner ear (e.g., the cochlea). In cases in which the nucleic acid vectors are AAV vectors (e.g., AAV1, AAV2, AAV2quad(Y-F), AAV3, AAV4, AAV5, AAV6, AAV7, AAV8, AAV9, AAV10, AAV11, rh10, rh39, rh43, rh74, Anc80, Anc80L65, DJ/8, DJ/9, 7m8, PHP.B, PHP.eb, or PHP.S vectors), the viral vectors may be administered to the patient at a dose of, for example, from about $1\times10^{10}$ vector genomes (VG) to $1\times10^{15}$ VG (e.g., $1\times10^{10}$VG, $2\times10^{10}$VG, $3\times10^{10}$VG, $4\times10^{10}$VG, $5\times10^{10}$ VG, $6\times10^{10}$VG, $7\times10^{10}$VG, $8\times10^{10}$VG, $9\times10^{10}$VG, $1\times10^{11}$ VG, $2\times10^{11}$ VG, $3\times10^{11}$ VG, $4\times10^{11}$ VG, $5\times10^{11}$ VG, $6\times10^{11}$ VG, $7\times10^{11}$ VG, $8\times10^{11}$ VG, $9\times10^{11}$ VG, $1\times10^{12}$VG, $2\times10^{12}$VG, $3\times10^{12}$ VG, $4\times10^{12}$ VG, $5\times10^{12}$ VG, $6\times10^{12}$ VG, $7\times10^{12}$ VG, $8\times10^{12}$ VG, $9\times10^{12}$ VG, $1\times10^{13}$ VG, $2\times10^{13}$ VG, $3\times10^{13}$ VG, $4\times10^{13}$ VG, $5\times10^{13}$ VG, $6\times10^{13}$ VG, $7\times10^{13}$ VG, $8\times10^{13}$ VG, $9\times10^{13}$ VG, $1\times10^{14}$ VG, $2\times10^{14}$ VG, $3\times10^{14}$ VG, $4\times10^{14}$ VG, $5\times10^{14}$ VG, $6\times10^{14}$ VG, $7\times10^{14}$ VG, $8\times10^{14}$ VG, $9\times10^{14}$ VG, $1\times10^{15}$ VG) in a volume of 1 µL to 200 µL (e.g., 1, 2, 3, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, or 200 µL).

The compositions described herein are administered in an amount sufficient to improve hearing, improve vestibular function (e.g., improve balance or reduce dizziness or vertigo), reduce tinnitus, increase expression of a therapeutic protein encoded by a transgene, increase function of a therapeutic protein encoded by a transgene, prevent or reduce hair cell damage, prevent or reduce hair cell death (e.g., ototoxic drug-induced hair cell death, age-related hair cell death, or noise (e.g., acoustic trauma)-related hair cell death), promote or increase hair cell development, increase hair cell numbers (e.g., promote or induce hair cell regeneration), increase or promote hair cell survival, or improve hair cell function. Hearing may be evaluated using standard hearing tests (e.g., audiometry, ABR, electrocochleography (ECOG), and otoacoustic emissions) and may be improved by 5% or more (e.g., 5%, 10%, 15%, 20%, 30%, 40%, 50%, 60%, 70%, 80%, 90%, 100%, 125%, 150%, 200% or more) compared to hearing measurements obtained prior to treatment. Vestibular function may be evaluated using standard tests for balance and vertigo (e.g., eye movement testing (e.g., ENG or VNG), posturography, rotary-chair testing, ECOG, VEMP, and specialized clinical balance tests) and may be improved by 5% or more (e.g., 5%, 10%, 15%, 20%, 30%, 40%, 50%, 60%, 70%, 80%, 90%, 100%, 125%, 150%, 200% or more) compared to measurements obtained prior to treatment. In some embodiments, the compositions are administered in an amount sufficient to improve the subject's ability to understand speech. The compositions described herein may also be administered in an amount sufficient to slow or prevent the development or progression of sensorineural hearing loss and/or vestibular dysfunction (e.g., in subjects who carry a genetic mutation associated with hearing loss or vestibular dysfunction, who have a family history of hearing loss or vestibular dysfunction (e.g., hereditary hearing loss or vestibular dysfunction), or who have been exposed to risk factors associated with hearing loss or vestibular dysfunction (e.g., ototoxic drugs, head trauma, acoustic trauma, or infection) but do not exhibit hearing impairment or vestibular dysfunction (e.g., vertigo, dizziness, or imbalance), or in subjects exhibiting mild to moderate hearing loss or vestibular dysfunction). Expression of the therapeutic protein encoded by the transgene operably linked to a Myo15 promoter in the nucleic acid vector administered to the subject may be evaluated using immunohistochemistry, Western blot analysis, quantitative real-time PCR, or other methods known in the art for detection protein or mRNA, and may be increased by 5% or more (e.g., 5%, 10%, 15%, 20%, 30%, 40%, 50%, 60%, 70%, 80%, 90%, 100%, 125%, 150%, 200% or more) compared to expression prior to administration of the compositions described herein. Hair cell numbers, hair cell function, or function of the therapeutic protein encoded by the nucleic acid vector administered to the subject may be evaluated indirectly based on hearing tests or tests of vestibular function, and may be increased by 5% or more (e.g., 5%, 10%, 15%, 20%, 30%, 40%, 50%, 60%, 70%, 80%, 90%, 100%, 125%, 150%, 200% or more) compared to hair cell numbers, hair cell function, or function of the therapeutic protein prior to administration of the compositions described herein. Hair cell damage or death may be reduced by 5% or more (e.g., 5%, 10%, 15%, 20%, 30%, 40%, 50%, 60%, 70%, 80%, 90%, 100%, 125%, 150%, 200% or more) compared to hair cell damage and death typically observed in untreated subjects. These effects may occur, for example, within 1 week, 2 weeks, 3 weeks, 4 weeks, 5 weeks, 6 weeks, 7 weeks, 8 weeks, 9 weeks, 10 weeks, 15 weeks, 20 weeks, 25 weeks, or more, following administration of the compositions described herein. The patient may be evaluated 1 month, 2 months, 3 months, 4 months, 5 months, 6 months or more following administration of the composition depending on the dose and route of administration used for treatment. Depending on the outcome of the evaluation, the patient may receive additional treatments.

Kits

The compositions described herein can be provided in a kit for use in treating sensorineural hearing loss or vestibular dysfunction. Compositions may include a polynucleotide described herein (e.g., a polynucleotide that contains first region having at least 85% sequence identity (e.g., 85%, 90%, 95%, 96%, 97%, 98%, 99%, or more, sequence identity) to SEQ ID NO: 1 or a functional portion or derivative thereof and/or a second region having at least 85% sequence identity (e.g., 85%, 90%, 95%, 96%, 97%, 98%, 99%, or more, sequence identity) to SEQ ID NO: 2 or a functional portion or derivative thereof, that optionally contains a linker between the first region and the second region), nucleic acid vectors containing such polynucleotides, and nucleic acid vectors containing a polynucleotide described herein operably linked to a transgene encoding a protein of interest (e.g., a protein that can be expressed in hair cells to treat hearing loss and/or vestibular dysfunction). The nucleic acid vectors may be packaged in an AAV virus capsid (e.g., AAV1, AAV2, AAV2quad(Y-F), AAV6, AAV9, Anc80, Anc80L65, DJ/9, 7m8, or PHP.B). The kit can further include a package insert that instructs a user of the kit, such as a physician, to perform the methods described herein. The kit may optionally include a syringe or other device for administering the composition.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1: Generation of the Murine Myo15 Promoter

Regions of evolutionary conservation in the vertebrate Myo15 promoter were first identified using the UCSC Genome Browser (genome.ucsc.edu). The region immediately upstream of the Myo15 translation start site (−1 to −1157, SEQ ID NO: 1) and an upstream region containing non-coding exon1 of the Myo15 gene (−6755 to −7209, SEQ ID NO: 2) were synthesized and joined together as a single DNA fragment by de novo gene synthesis (SEQ ID NO: 13). The total size of the truncated Myo15 promoter is 1611 bp versus more than 7000 bp for the entire genomic region.

Experiments evaluating tropism (cell type targeting) and the extent and duration of transgene expression by the Myo15 promoter relative to the cytomegalovirus (CMV) promoter in mouse cochlea resulted in the Myo15 promoter, but not the CMV promoter, yielding selective expression in cochlear hair cells. An AAV construct was created with Myo15 driving expression of Aequorea coerulescens green fluorescent protein (AcGFP) to analyze the progression of gene expression relative to the matched standard AAV construct with CMV. Transgene expression was evaluated in experiments in which virus was delivered to the mouse cochlea in neonatal mice, in adult mice, and ex vivo in cochlear explants.

Figure 1B:
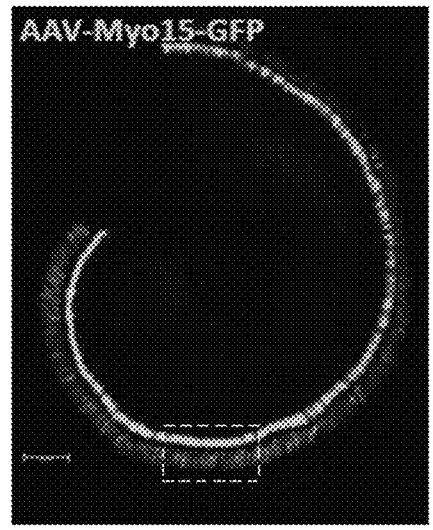
Figure 2:
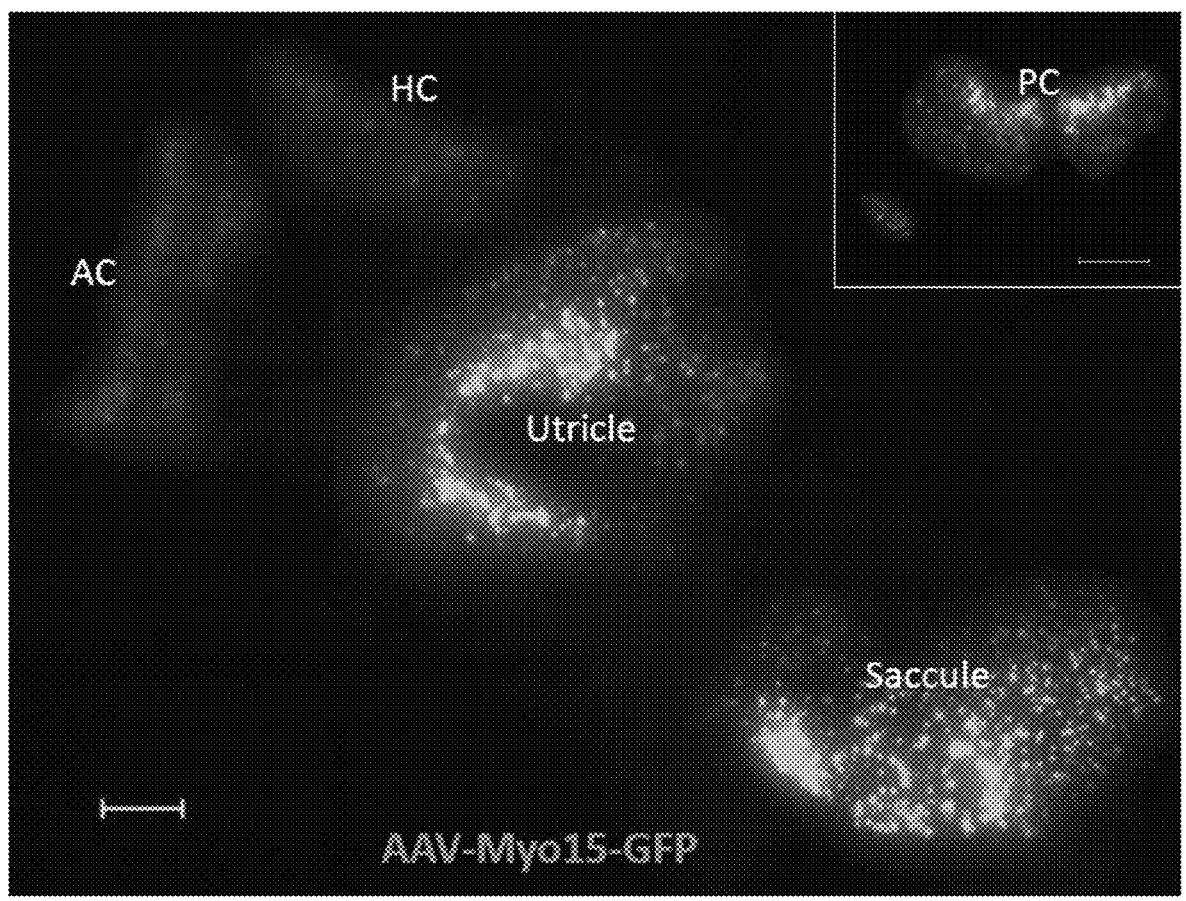
FIG. 2 is a fluorescent image of regions of the mouse vestibular system (utricle, saccule, posterior crista (PC), anterior crista (AC), and horizontal crista (HC)) transduced with an AAV vector expressing GFP under control of the murine Myo15 promoter (SEQ ID NO: 13, FIG. 2). AAV-Myo15-GFP virus was infused via posterior semi-circular canal to 6-8-week-old C57Bl/6J male mice. Mice recovered from surgery and were euthanized and perfused with 10% normal buffered formalin 10 days later. The inner ear temporal bone was harvested and decalcified in 8% EDTA for 3 days. The vestibular organs were dissected from the de-calcified temporal bone and mounted on a slide for imaging. Using the hair cell-specific promoter, AAV-Myo15-GFP induced expression exclusively in vestibular hair cells (FIG. 2).

To evaluate transgene expression, AAV-Myo15-GFP virus was infused via posterior semi-circular canal to 6-8-week-old C57Bl/6J male mice. Mice recovered from surgery and were euthanized and perfused with 10% normal buffered formalin 10 days later. The inner ear temporal bone was harvested and decalcified in 8% EDTA for 3 days. The cochlea or vestibular system were dissected from the decalcified temporal bone and mounted on a slide for imaging. Using a ubiquitous promoter, AAV-CMV-GFP induced GFP expression in many cell types within the cochlea including inner hair cells, outer hair cells, spiral ganglion neurons, mesenchymal cells, and glia (FIG. 1A). Using the hair cell-specific promoter, AAV-Myo15-GFP induced expression exclusively in the inner and outer hair cells (FIG. 1B). In the vestibular system, AAV-Myo15-GFP induced expression exclusively in vestibular hair cells (FIG. 2).

Example 2: Generation of a Minimal Myo15 Promoter

A series of promoters are generated and placed upstream of a fluorescent reporter (e.g., GFP, AcGFP, or luciferase). Promoters that are generated include:
1) SEQ ID NO: 3 fused to SEQ ID NO: 2;
2) SEQ ID NO: 4 fused to SEQ ID NO: 2;
3) A fusion of SEQ ID NO: 3 and SEQ ID NO: 4 (e.g., SEQ ID NO: 5, 6, or 7) fused to SEQ ID NO: 2;
4) SEQ ID NO: 8 fused to SEQ ID NO: 9 (e.g., SEQ ID NO: 10, 11, or 12);
5) SEQ ID NO: 1 fused to a fusion of SEQ ID NO: 8 and SEQ ID NO: 9 (e.g., SEQ ID NO: 10, 11 or 12);
6) SEQ ID NO: 3 fused to a fusion of SEQ ID NO: 8 and SEQ ID NO: 9 (e.g., SEQ ID NO: 10, 11, or 12);
7) SEQ ID NO: 4 fused to a fusion of SEQ ID NO: 8 and SEQ ID NO: 9 (e.g., SEQ ID NO: 10, 11, or 12);
8) A fusion of SEQ ID NO: 3 and SEQ ID NO: 4 (e.g., SEQ ID NO: 5, 6, or, 7) fused to a fusion of SEQ ID NO: 8 and SEQ ID NO: 9 (e.g., SEQ ID NO: 10, 11, or 12);
9) A fusion of SEQ ID NO: 3 and SEQ ID NO: 4 (e.g., SEQ ID NO: 5, 6, or 7);
11) SEQ ID NO: 1;
12) SEQ ID NO: 2;
13) SEQ ID NO: 17;
14) SEQ ID NO: 18;
15) SEQ ID NO: 17 fused to SEQ ID NO: 18;
16) SEQ ID NO: 18 fused to SEQ ID NO: 17;
17) SEQ ID NO: 19 fused to SEQ ID NO: 18;
18) SEQ ID NO: 20 fused to SEQ ID NO: 21 (e.g., SEQ ID NO: 22, 23, or 24);
19) SEQ ID NO: 17 fused to a fusion of SEQ ID NO: 20 and SEQ ID NO: 21 (e.g., SEQ ID NO: 22, 23, or 24); and
20) SEQ ID NO: 19 fused to a fusion of SEQ ID NO: 20 and SEQ ID NO: 21 (e.g., SEQ ID NO: 22, 23, or 24).

The promoter constructs are packaged into an AAV serotype capable of transducing hair cells (e.g., AAV1, AAV2, AAV6, AAV9, Anc80, or Anc80L65).

Viral promoter constructs are used to infect organotypic cochlear explants. After 48 hours of incubation with virus, explants are imaged and analyzed using fluorescence intensity of the reporter to gauge hair cell-specific expression.

Example 3: Administration of a Composition Containing a Nucleic Acid Vector Containing a Myo15 Promoter to a Subject with Sensorineural Hearing Loss According to the methods disclosed herein, a physician of skill in the art can treat a patient, such as a human patient, with sensorineural hearing loss so as to improve or restore hearing. To this end, a physician of skill in the art can administer to the human patient a composition containing an AAV vector (e.g., AAV1, AAV2, AAV2quad(Y-F), AAV6, AAV9, Anc80, Anc80L65, DJ/9, 7m8, or PHP.B) containing a polynucleotide that contains first region having at least 85% sequence identity (e.g., 85%, 90%, 95%, 96%, 97%, 98%, 99%, or more, sequence identity) to SEQ ID NO: 1 or a functional portion or derivative thereof (e.g., any one or more of SEQ ID NOs: 3-7, e.g., SEQ ID NOs 3 and 4) and/or a second region having at least 85% sequence identity (e.g., 85%, 90%, 95%, 96%, 97%, 98%, 99%, or more, sequence identity) to SEQ ID NO: 2 or a functional portion or derivative thereof (e.g., any one or more of SEQ ID NOs: 8-12, e.g., SEQ ID NOs: 8 and 9), that optionally contains a linker between the first region and the second region, operably linked to a transgene that encodes a therapeutic protein. For example, the polynucleotide operably linked to the transgene that encodes a therapeutic protein may be SEQ ID NO: 13, SEQ ID NO: 15, SEQ ID NO: 16, SEQ ID NO: 36, or SEQ ID NO: 37. The composition containing the AAV vector may be administered to the patient, for example, by local administration to the inner ear (e.g., injection into the perilymph), to treat sensorineural hearing loss.

Following administration of the composition to a patient, a practitioner of skill in the art can monitor the expression of the therapeutic protein encoded by the transgene, and the patient's improvement in response to the therapy, by a variety of methods. For example, a physician can monitor the patient's hearing by performing standard tests, such as audiometry, ABR, electrocochleography (ECOG), and otoacoustic emissions following administration of the composition. A finding that the patient exhibits improved hearing in one or more of the tests following administration of the composition compared to hearing test results prior to administration of the composition indicates that the patient is responding favorably to the treatment. Subsequent doses can be determined and administered as needed.

Example 4: Murine Myo15 Promoter Sequences Containing Portions of SEQ ID NO: 1 and SEQ ID NO: 2 Induce Transgene Expression in Hair Cells Neonatal cochlear explants were established from P0 wildtype CD1 mice. Briefly, neonatal mice were euthanized according to IACUC approved protocols. Inner ears were removed from the head and the cochlea was carefully removed using microdissection. The modiolus was removed from the center of the coil and the roof of the cochlear duct was removed exposing the sensory epithelium. Cochlear explants were plated, lumenal side of the cochlear duct facing up, on Mat-tek dishes coated in 15% Matrigel. Cochlear explant culture media consisting of DMEM with 10% FBS and 10 ug/mL ciproflaxin was added directly to the culture. Virus containing the Myo15 1 kb (SEQ ID NO: 15) promoter or the Myo15 mini intron (SEQ ID NO: 16) promoter (AAV 2/9-Myo15 1 kb-GFP or AAV2/9-Myo15 mini intron-GFP) was added to the culture media at a concentration of 1E+10 genome copies/mL. Cultures were incubated in media containing virus for 48 hours in standard culture conditions of 5% $CO_2$ at 37° C. Cultures were then fixed in 4% PFA, permeabilized with 0.01% TritonX100, and blocked with 10% normal donkey serum before antibody staining. Antibodies used: Rabbit anti-Myo6 (Proteus), Donkey anti-Rabbit Alexa 568 (Thermo Fisher). As shown in FIGS. 3A-3B, both the Myo15 1 kb (SEQ ID NO: 15) and Myo15 mini intron (SEQ ID NO: 16) promoters induced expression of GFP specifically in hair cells.

Figure 4A:
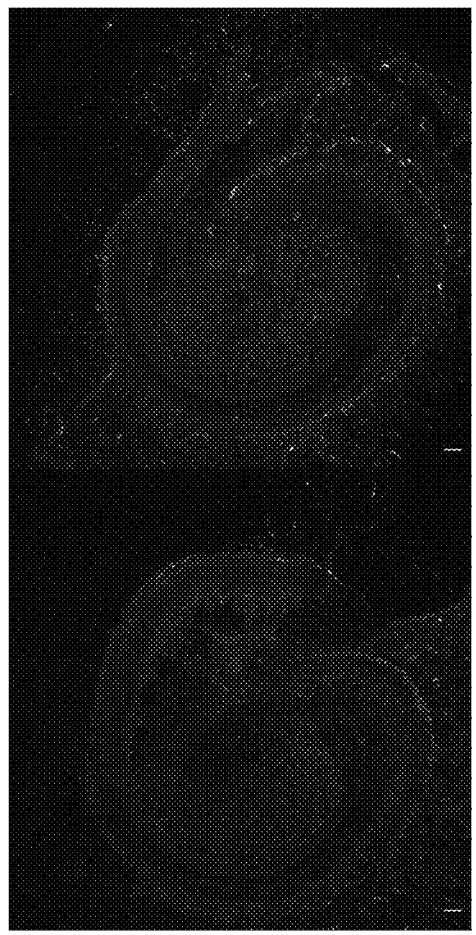

Example 5: Myo15 Promoter Sequences Induce Transgene Expression in Hair Cells in Murine Cochlea Neonatal cochlear explants were established from P0 wildtype B6.CAST-Cdh23Al+/Kjn mice. Briefly, neonatal mice were euthanized according to IACUC approved protocols. Inner ears were removed from the head and the cochlea was carefully removed using microdissection. The modiolus was removed from the center of the coil and the roof of the cochlear duct was removed exposing the sensory epithelium. Cochlear explants were plated, lumenal side of the cochlear duct facing up, on prepared 3D rat tail collagen matrices. Cochlear explant culture media consisting of DMEM with 7% FBS and 1 U/μL penicillin G was added directly to the culture. Virus containing the murine Myo15 1 kb (SEQ ID NO: 15) promoter, human Myo15 0.6 kb (SEQ ID NO: 26), or human Myo15 1.2 kb (SEQ ID NO: 25) promoter (AAV1-Myo15 1 kb-GFP, AAV1-Myo15 0.6 kb-GFP, or AAV1-Myo15 1.2 kb-GFP) was added to the culture media at a concentration of 1E+11 vg/culture. Cultures were incubated in media containing virus for 72 hours in standard culture conditions of 5% $CO_2$ at 37° C. Cultures were then fixed in 4% PFA, permeabilized with 0.01% TritonX100, and blocked with 10% normal donkey serum before anti-GFP antibody staining. GFP signal, as detected with anti-GFP antibody, is shown (FIGS. 4A-4C). In a separate experiment, AAV1-1.2 kb human Myo15-GFP or AAV1-1 kb murine Myo15-GFP was delivered to adult mouse cochlea via round window injection at a dose of 2.65E+12 vg/ml. Whole mount images (FIGS. 4D-4E) or sections (FIGS. 4F-4G) show hair cell-specific signal in the apex, middle, and base of the cochlea, as detected with anti-GFP antibody. Arrows in FIG. 4F point to GFP-labeled cochlear hair cells. As shown in FIGS. 4F and 4G, expression with both the 1.2 kb human Myo15 promoter and 1 kb murine Myo15 promoter was restricted primarily to inner hair cells.

Figure 5A:
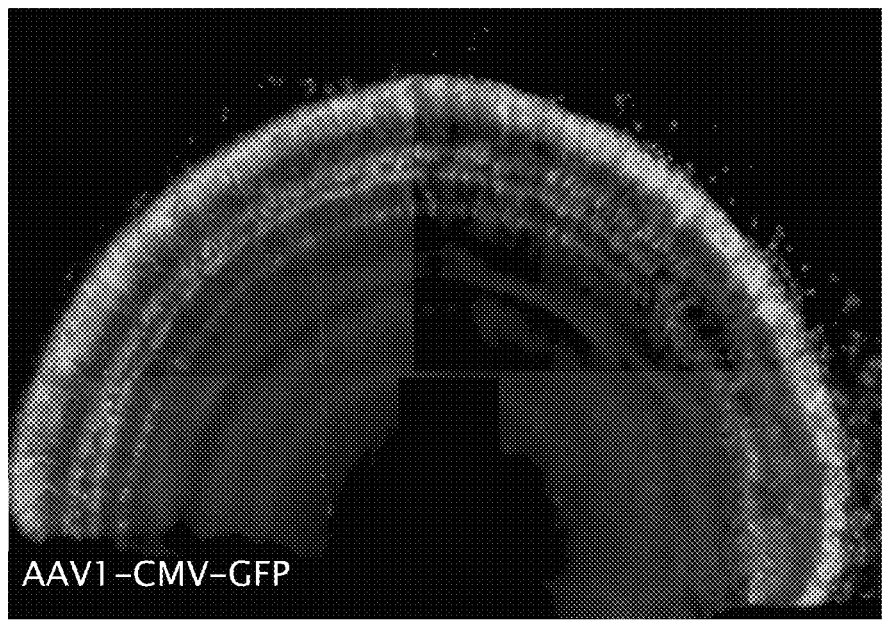
FIGS. 5A-5C is a series of fluorescent images of non-human primate cochlea showing that the Myo15 promoter restricts GFP expression to hair cells in the cochlea of a non-human primate.
Figure 5B:
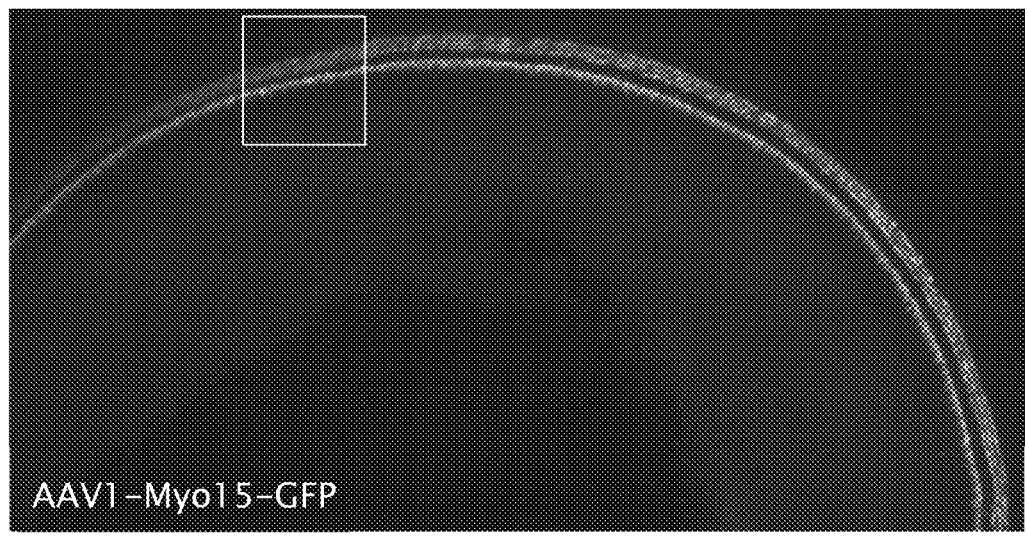
Figure 5C:

Example 6: Murine Myo15 Promoter Sequences Induce Transgene Expression in Cochlea of Non-Human Primates In Vivo Murine Myo15 promoter specificity was tested in non-human primates. Thirty microliters of AAV1-CMV-GFP or AAV1-Myo15 (SEQ ID NO: 13)-GFP were injected into the cochleas through the round window membrane at 15 μl/min. The animals were sacrificed four weeks after AAV injection, and the cochleas were harvested and processed as a surface preparation to examine transgene expression without antibody augmentation. AAV1 had high infectivity. Under the ubiquitous CMV promoter, GFP was expressed in hair cells, supporting cells, and fibrocytes in the lateral wall in the rhesus cochlea (FIG. 5A). In contrast, the 1.6 kb murine Myo15 promoter (SEQ ID NO: 13) restricted GFP transgene expression to hair cells in a cynomolgus cochlea (FIGS. 5B-5C).

Example 7: The Murine Myo15 Promoter Enhances Biological Efficacy of AAV-Mouse Tmc1 in Tmc1 Knockout Mice Compared to a Ubiquitous Promoter Tmc1 knockout (KO) mice were anesthetized with isoflurane, hair clipped, and providone iodine was applied to the skin. An incision was made under the left ear from above the cheek muscle to behind the ear. Skin was separated and muscle teased and cleared to expose the posterior canal. A drill bit was used to make a small hole in the canal and bone was kept dry with fine cotton tips. A polyamide/polyethylene tubing was inserted into the hole and sealed with bone glue. A micropump with a Hamilton syringe was used to deliver 1 μl of vector (AAV-CMV1-mouse TMC1 or AAV-Myo15 (SEQ ID NO: 13)-mouse TMC1) with 0.05 μl of trypan blue into the IL space at 100 nl/min rate. After delivering 1 μl, 5 minutes were allowed to elapse for the fluid to reach the apex of the cochlea and to prevent back flow and leakage. The tube was bent and cut near the bone. Muscle was pulled back into place and skin was glued together. Mice were given 0.01 cc of Meloxicam before being allowed to recover under a heating lamp. Animals were checked for 5 days post-op for signs of pain or infection. Twenty-one to twenty-eight days post-op animals were anesthetized with ketamine and xylazine and the auditory brainstem response (ABR) was measured. As shown in FIG. 6, restoration of ABR thresholds was greatly improved in homozygous Tmc1 KO mice injected with AAV-Myo15-mouse TMC1 compared to AAV-CMV-mouse TMC1.

Figure 7A:
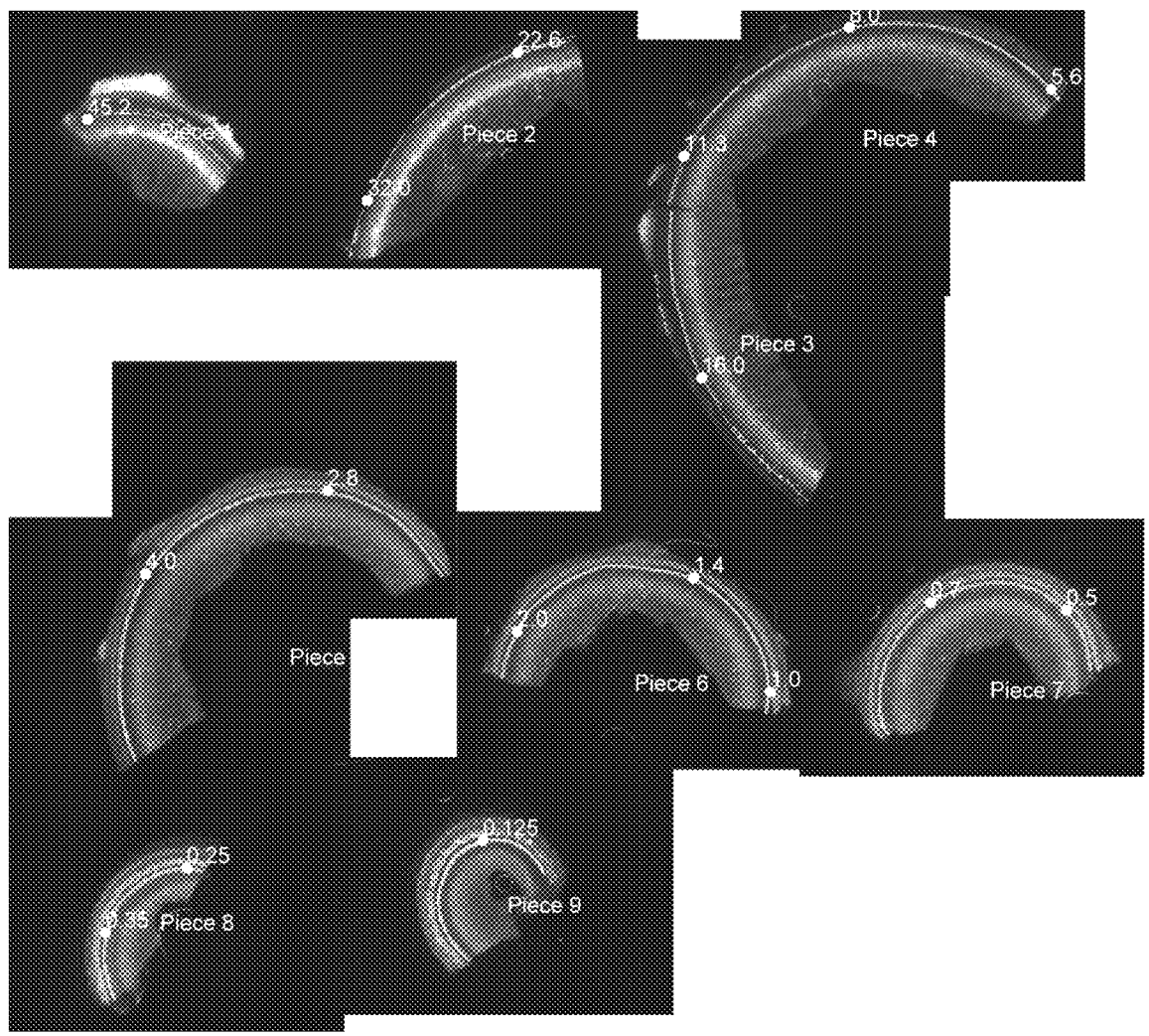
FIGS. 7A-7B are a series of fluorescence images of the inner ear of a cynomolgus monkey treated with an AAV1 vector expressing GFP under control of the 1.2 kb human myosin 15 promoter (SEQ ID NO: 25). Bilateral (n=1 animal) injections were used to administer 30 μL of AAV1-1.2 kb Myosin 15-GFP (viral titer at $1.06 \times 10^{13}$ genome copies/mL) to the round window of the inner ear at a flow rate of 15 μL/min. Four weeks post-injection, inner ears were removed, and a surface preparation of the basilar membranes was made. GFP expression was used to monitor Myosin 15 promoter activity (FIG. 7A, one of the representative ears is shown). AAV1-1.2 kb Myosin 15-GFP transduction of the inner ear of cynomolgus monkeys resulted in GFP expression across the entire baso-apical axis of the cochlea with high frequency at base and low frequency at apex (FIG. 7A, frequencies at kHz). High magnification images at 2.8 kHz showed GFP expression was observed within inner hair cells (IHCs) and outer hair cells (OHC) (FIG. 7B, upper panel). Immunohistochemistry for Myo7A was used to visualize hair cells and nuclei were stained with DAPI (FIG. 7B, middle and lower panels).
Figure 7B:
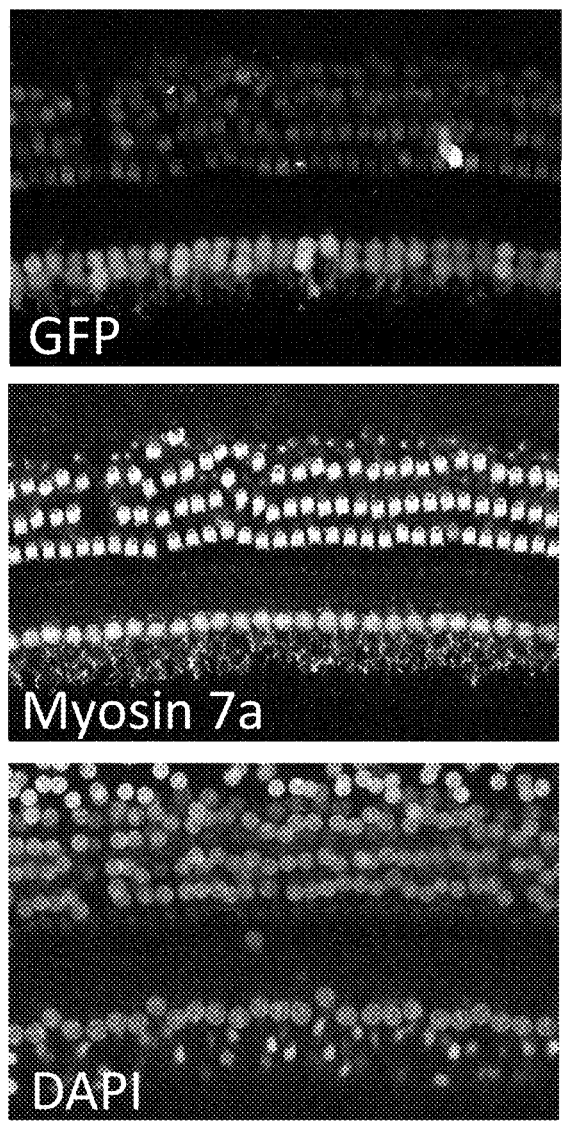
Figure 8A:
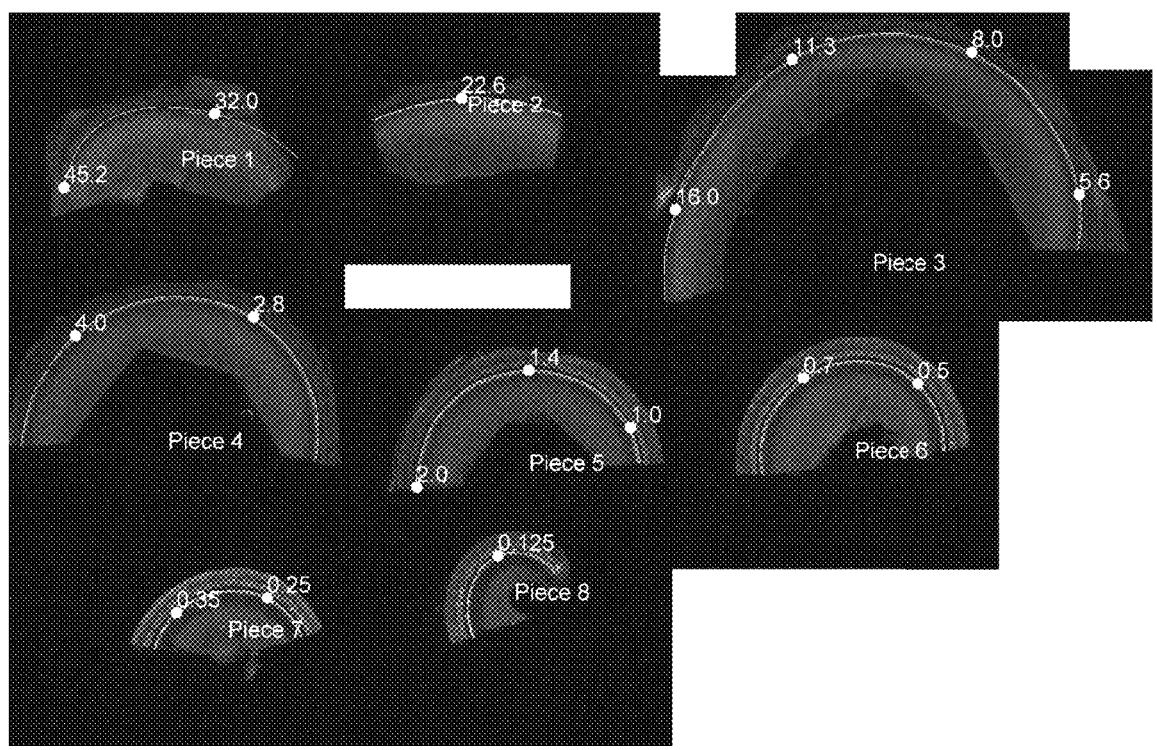
FIGS. 8A-8B are a series of fluorescence images of the inner ear of a cynomolgus monkey treated with an AAV1 vector expressing GFP under control of the 0.6 kb human myosin 15 promoter (SEQ ID NO: 26). Bilateral (n=1 animal) injections were used to administer 30 µL of AAV1-0.6 kb Myosin 15-GFP (viral titer at 1.22×10$^{13}$ genome copies/mL) to the round window of the inner ear at a flow rate of 15 µL/min. Four weeks post-injection, inner ears were removed, and a surface preparation of the basilar membranes was made. GFP expression was used to monitor Myosin 15 promoter activity (FIG. 8A, one of the representative ears is shown). AAV1-0.6 kb Myosin 15-GFP transduction of the inner ear of cynomolgus monkeys resulted in GFP expression across the entire baso-apical axis of the cochlea with high frequency at base and low frequency at apex (FIG. 8A, frequencies at kHz). High magnification images at 2.8 kHz showed GFP expression was observed within inner hair cells (IHCs) and outer hair cells (OHC) (FIG. 8B, upper panel). Immunohistochemistry for Myo7A was used to visualize hair cells and nuclei were stained with DAPI (FIG. 8B, middle and lower panels).
Figure 8B:
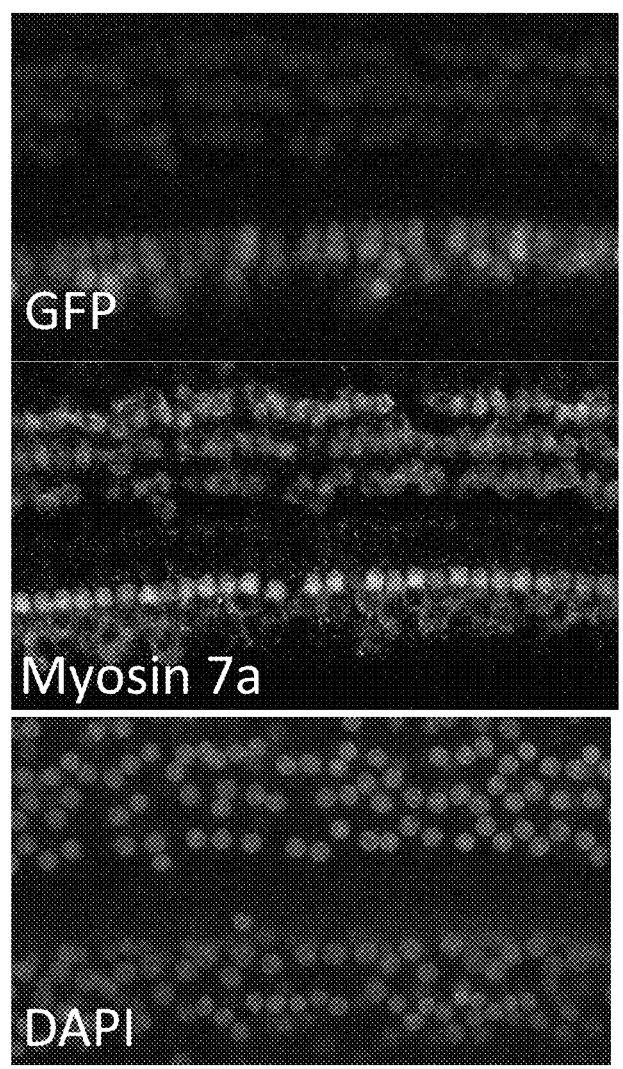

Example 8: Human Myo15 Promoter Sequences Induce Transgene Expression in Cochlea of Non-Human Primates In Vivo A composition containing an AAV1 vector carrying an EGFP transgene under the control of the 1.2 kb human myosin 15 promoter (SEQ ID NO: 25) or the 0.6 kb human myosin 15 promoter (SEQ ID NO: 26) was delivered bilaterally into the inner ear of cynomolgus monkeys by way of injection through the round window membrane. Injections (30 μL) of AAV1-1.2 kb Myosin 15-GFP (viral titer at $1.06 \times 10^{13}$ genome copies/mL) or AAV1-0.6 kb Myosin 15-GFP (viral titer at $1.22 \times 10^{13}$ genome copies/mL) were performed at an injection rate of 15 μL/min. Four weeks post-injection, inner ears were removed, and a surface preparation of the basilar membranes was made. GFP expression was used to monitor Myosin 15 promoter activity (FIGS. 7A and 8A, one of the representative ears is shown). AAV1-1.2 kb Myosin 15-GFP transduction of the inner ear of cynomolgus monkeys resulted in GFP expression across the entire baso-apical axis of the cochlea with high frequency at base and low frequency at apex (FIG. 7A, frequencies at kHz). High magnification images at 2.8 kHz showed GFP expression was observed within inner hair cells (IHCs) and outer hair cells (OHC) (FIG. 7B upper panel). Similarly, AAV1-0.6 kb Myosin 15-GFP transduction of the inner ear of cynomolgus monkeys resulted in GFP expression across the entire baso-apical axis of the cochlea with high frequency at base and low frequency at apex (FIG. 8A, frequencies at kHz). High magnification images at 2.8 kHz showed GFP expression was observed within IHCs and OHCs (FIG. 8B upper panel). Immunohistochemistry for myosin 7A (Myo7A) was used to visualize hair cells and nuclei were stained with DAPI (FIG. 7B and FIG. 8B, middle and lower panels).

Example 9: Myo15 Promoter Variants Induce Transgene Expression in Murine Cochlear Explants Neonatal Cochlear Explant Culture and Viral Transduction Neonatal cochlear explants were established from P0 wildtype B6.CAST-Cdh23Ahl+/Kjn mice. Briefly, neonatal mice were euthanized according to Institutional Animal Care and Use Committee approved protocols. Inner ears were removed from the head and the cochlea was carefully removed using microdissection. The modiolus was removed from the center of the coil and the roof of the cochlear duct was removed exposing the sensory epithelium. Cochlear explants were plated, lumenal side of the cochlear duct facing up, on prepared 3D rat tail collagen matrices. Cochlear explant culture media consisting of DMEM with 7% FBS and 1 U/μL penicillin G was added directly to the culture. Virus containing the murine Myo15 1 kb (SEQ ID NO: 15) promoter, human Myo15 0.6 kb (SEQ ID NO: 26), human Myo15 1.2 kb (SEQ ID NO: 25) promoter, murine Myo15 0.5 kb promoter (SEQ ID NO: 16), murine Myo15 A promoter (SEQ ID NO: 27), murine Myo15 B promoter (SEQ ID NO: 28), murine Myo15 C promoter (SEQ ID NO: 29), murine Myo15 A-B promoter (SEQ ID NO: 30), murine Myo15 A-C promoter (SEQ ID NO: 31), murine Myo15 B-C promoter (SEQ ID NO: 32), murine Myo15 B-A-C promoter (SEQ ID NO: 33), murine Myo15 C-A-B promoter (SEQ ID NO: 34), or murine Myo15 B-C-A promoter (SEQ ID NO: 35; AAV1-Myo15 1 kb-GFP, AAV1-Myo15 0.6 kb-GFP, AAV1-Myo15 1.2 kb-GFP, AAV1-Myo15 0.5 kb-GFP, AAV1-Myo15 A-GFP, AAV1-Myo15 B-GFP) was added to the culture media at a concentration of $1\times10^{11}$ vg/culture. Cultures were incubated in media containing virus for 72 hours in standard culture conditions of 5% CO2 at 37° C.

GFP Quantification

After 72 hours in culture with virus-containing media, cultures were fixed in 4% PFA, permeabilized with 0.01% TritonX100, and blocked with 10% normal donkey serum before anti-Myo7a and/or anti-GFP antibodies. Samples were imaged using confocal microscopy (Zeiss LSM 810) using uniform settings (laser intensity and gain) between samples. ImageJ was used to quantify GFP intensity values per cell.

mRNA Quantification

After 72 hours in culture with virus-containing media, cultures were snap frozen on dry ice and RNA was extracted using PicoPure RNA Isolation Kit (Arcturus cat #0204). GFP and Myo7A mRNA were quantified by qPCR using the Quantinova Probe RT-PCR Kit (Qiagen cat #208354) for all cDNA synthesis and RT-PCR reactions. GFP expression levels were normalized to Myo7a expression.

Results

Figure 9:
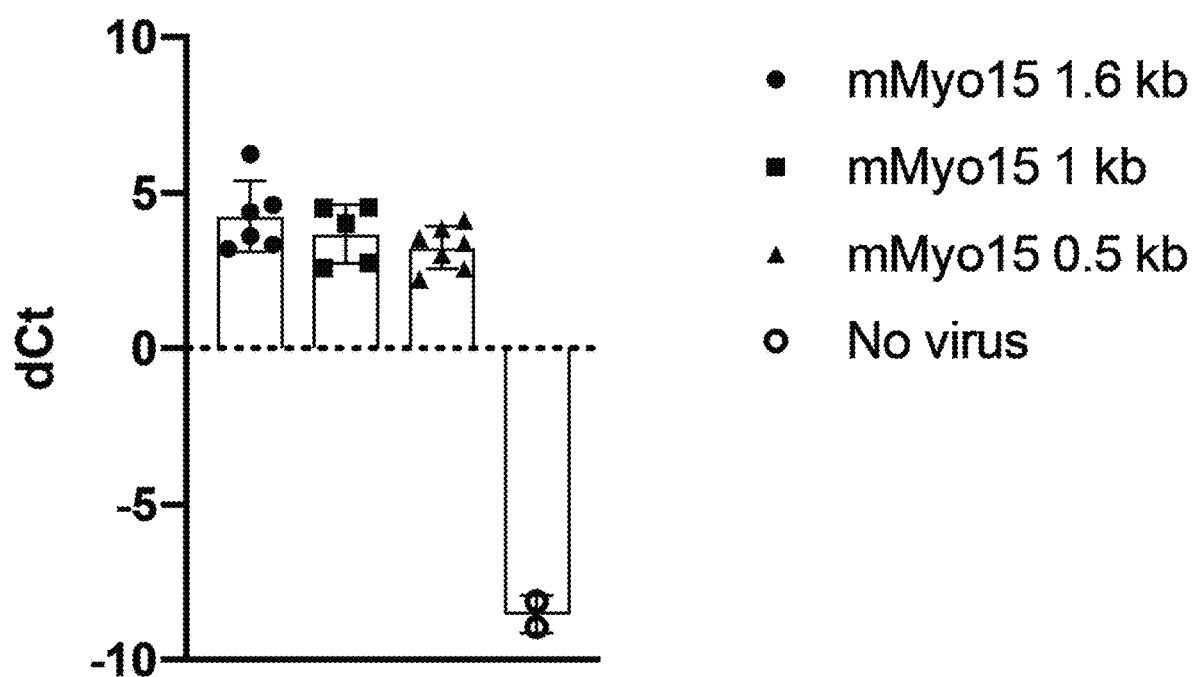
FIG. 9 is a bar plot showing quantification of GFP expression from three different murine Myo15 (mMyo15) promoters with hair cell specific expression using quantitative PCR (qPCR). Transcript levels were normalized to the hair cell specific gene Myo7a. Expression levels of the GFP reporter from the mMyo15 1.6 kb (SEQ ID NO: 13), 1 kb (SEQ ID NO: 15), and 0.5 kb (SEQ ID NO: 16) promoters were comparable to each other and robust.
Figure 10:
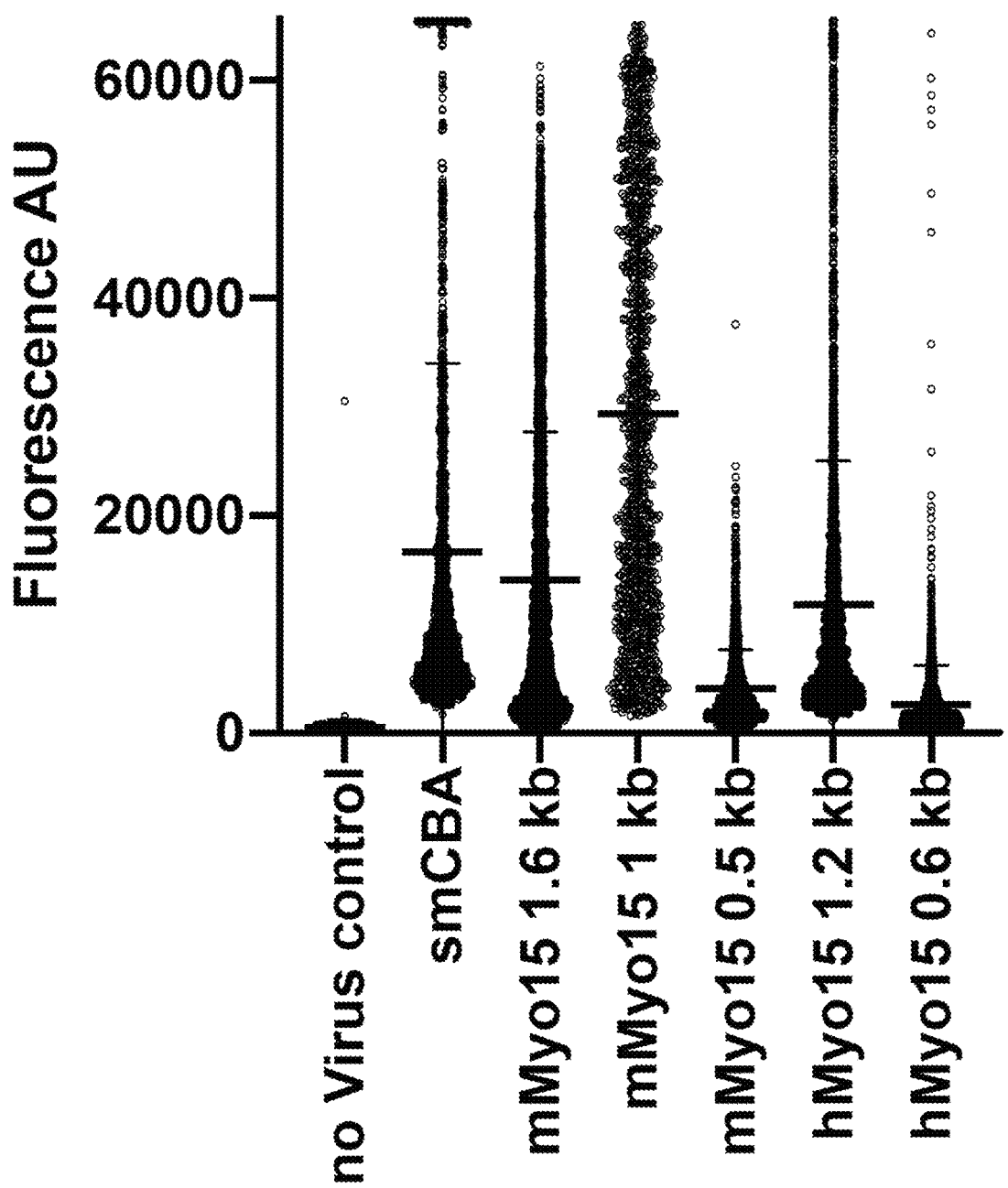
FIG. 10 is a graph showing the results of quantitative image analysis of GFP fluorescence in myosin 7a (Myo7a)-positive hair cells driven by a variety of different promoters including a truncated chimeric CMV-chicken β-actin (smCBA) promoter, 1.6 kb mMyo15 promoter (SEQ ID NO: 13), 1 kb mMyo15 promoter (SEQ ID NO: 15), 0.5 kb mMyo15 promoter (SEQ ID NO: 16), 1.2 kb hMyo15 promoter (SEQ ID NO: 25), and 0.6 kb hMyo15 promoter (SEQ ID NO: 26). Expression levels of GFP protein per cell indicate differences in expression between Myo15 promoters, with the mMyo15 1 kb promoter yielding the highest levels of GFP protein per cell.

Quantification of GFP expression from murine Myo15 promoters with hair cell-specific expression using quantitative PCR (qPCR) showed that expression levels of the GFP transgene from the mMyo15 1.6 kb, 1 kb, and 0.5 kb promoters were robust and comparable to each other in degree of GFP expression (FIG. 9). Comparison of GFP expression driven by a variety of murine or human Myo15 promoters showed differences in GFP expression in Myo7a-positive hair cells, with the mMyo15 1 kb promoter yielding the highest levels of GFP expression per cell (FIG. 10).

Figure 11A:
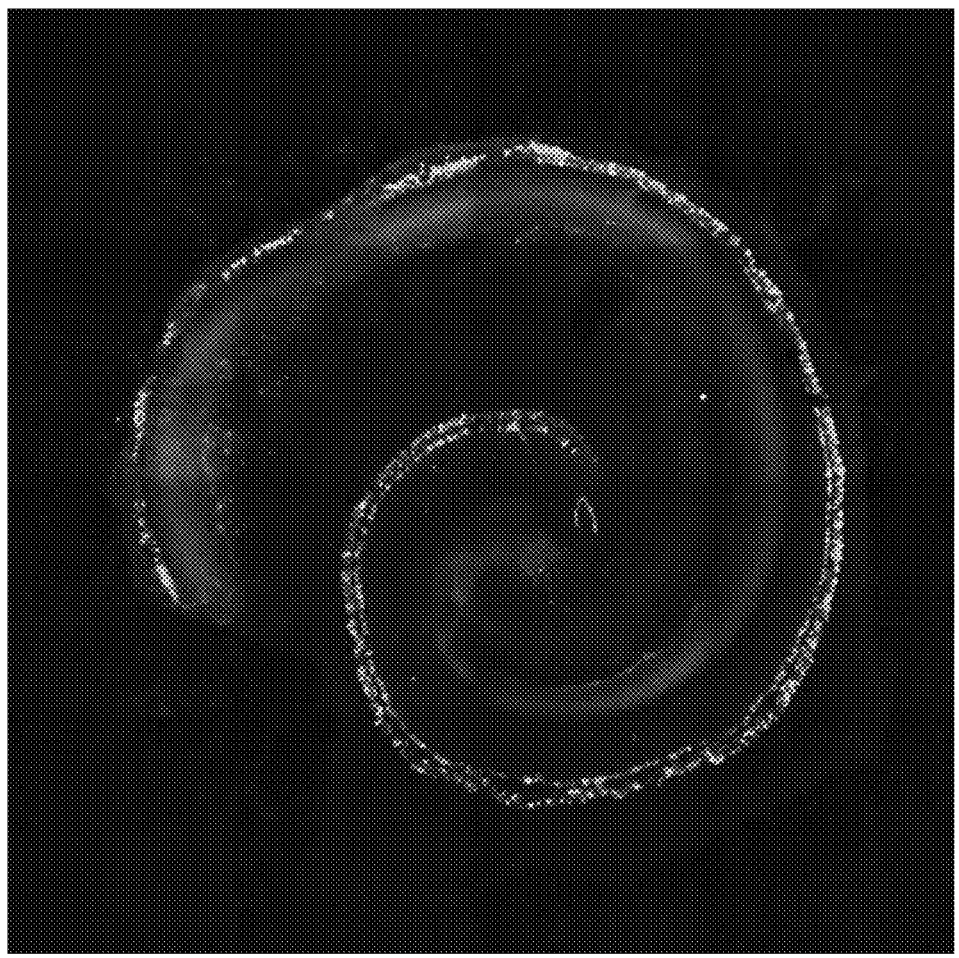
FIGS. 11A-11J are a series of whole mount fluorescence images of neonatal cochlear explant cultures infected with viral vectors containing the Myo15 promoter variants of SEQ ID NOs: 16 and 27-35. The promoter sequence of SEQ ID NO: 27 (Myo15 A) was neither sufficient nor necessary for general promoter activity or hair cell specificity as shown in FIGS. 11B (SEQ ID NO: 27), 11E (SEQ ID NO: 30), 11F (SEQ ID NO: 31), and 11G (SEQ ID NO: 32). The promoter sequence of SEQ ID NO: 27 did provide a splice donor site that increased expression levels when paired with a splice acceptor site as shown in FIGS. 11A (SEQ ID NO: 16) and 11H (SEQ ID NO: 33), thus introducing an intron into the promoter sequence. The promoter sequence of SEQ ID NO: 28 (Myo15 B) alone was found to be a core promoter that conferred general promoter activity as shown in FIG. 11C (SEQ ID NO: 28), but did not drive hair cell-specific GFP expression in the absence of the promoter sequence of SEQ ID NO: 29 (Myo15 C) as shown in FIGS. 11C (SEQ ID NO: 29) and 11G (SEQ ID NO: 32). The promoter sequence of SEQ ID NO: 29 (Myo15 C) was found to be an enhancer that restricted activity of the core promoter (SEQ ID NO: 28) to inner and outer hair cells as shown in FIG. 11G (SEQ ID NO: 32), but was not sufficient for general promoter activity in the absence of the core promoter as shown in FIG. 11D (SEQ ID NO: 29). The promoter sequences of SEQ ID NO: 27, SEQ ID NO: 28, and SEQ ID NO: 29 were reordered into various combinations and still resulted in hair cell specific promoter activity as shown in FIGS. 11H (SEQ ID NO: 33) and 11I (SEQ ID NO: 34), although not all rearrangements were tolerated, as shown in FIG. 11J (SEQ ID NO: 35).
Figure 11B:
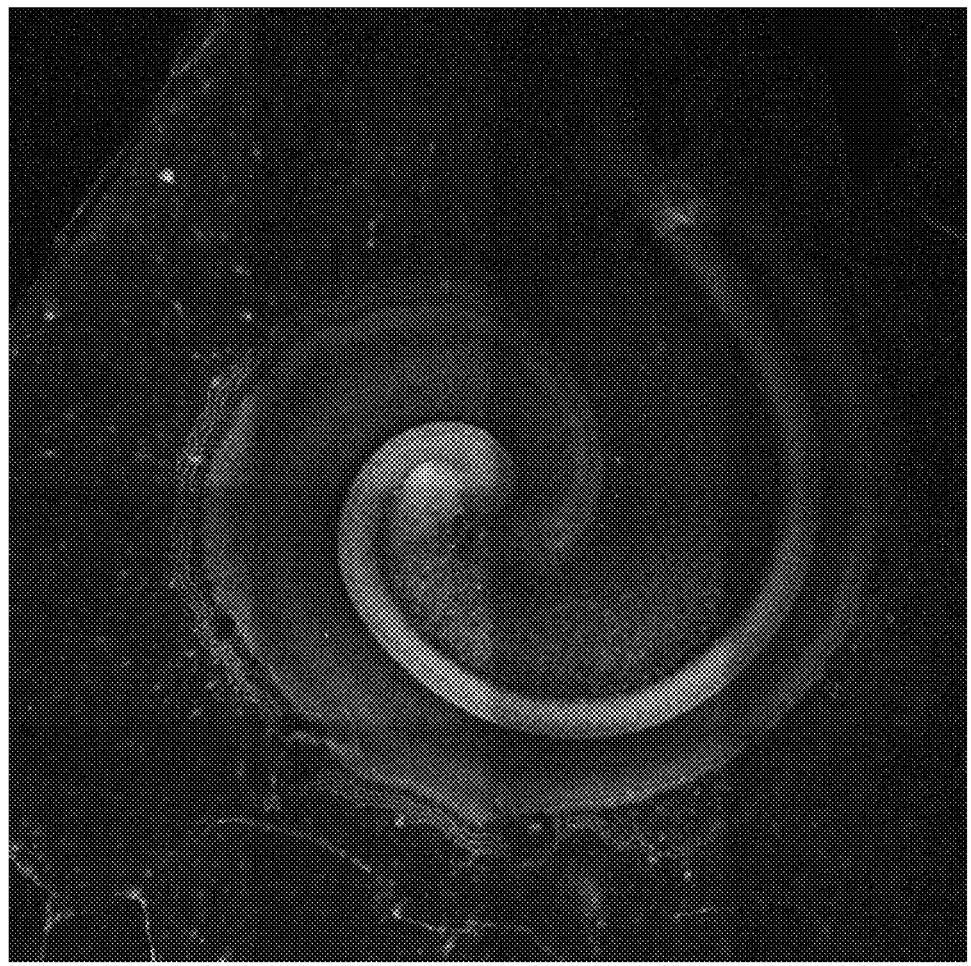
Figure 11C:
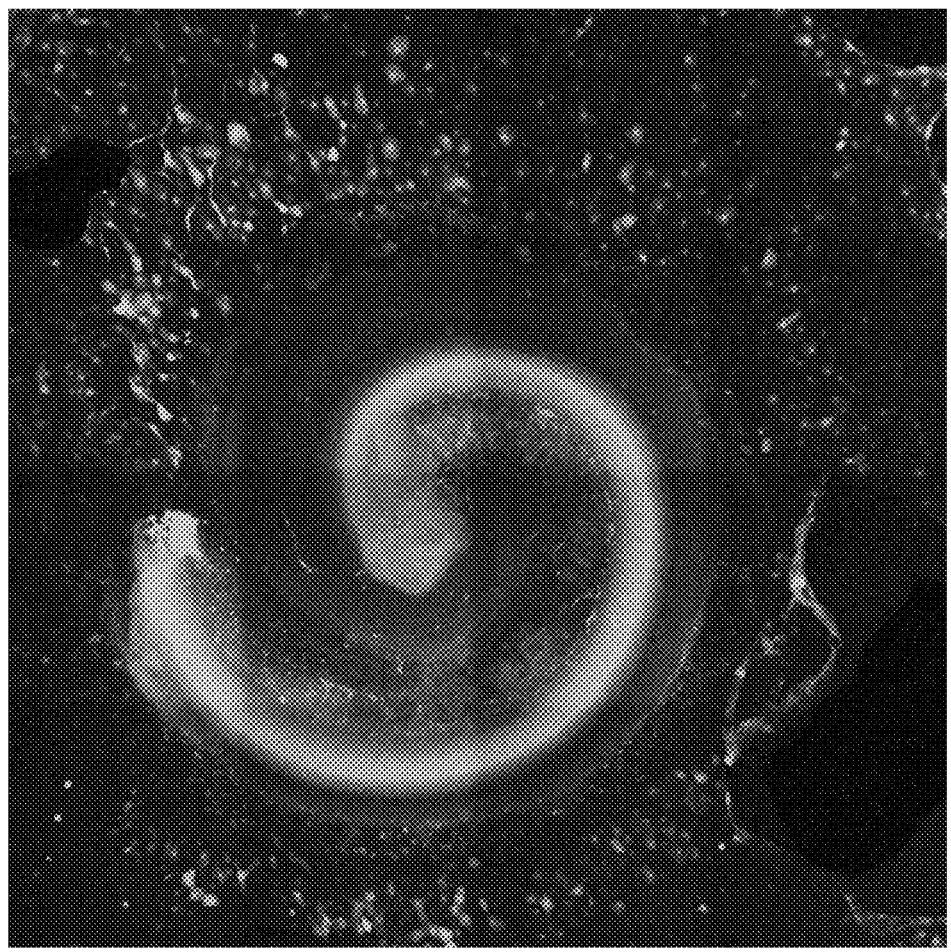
Figure 11D:
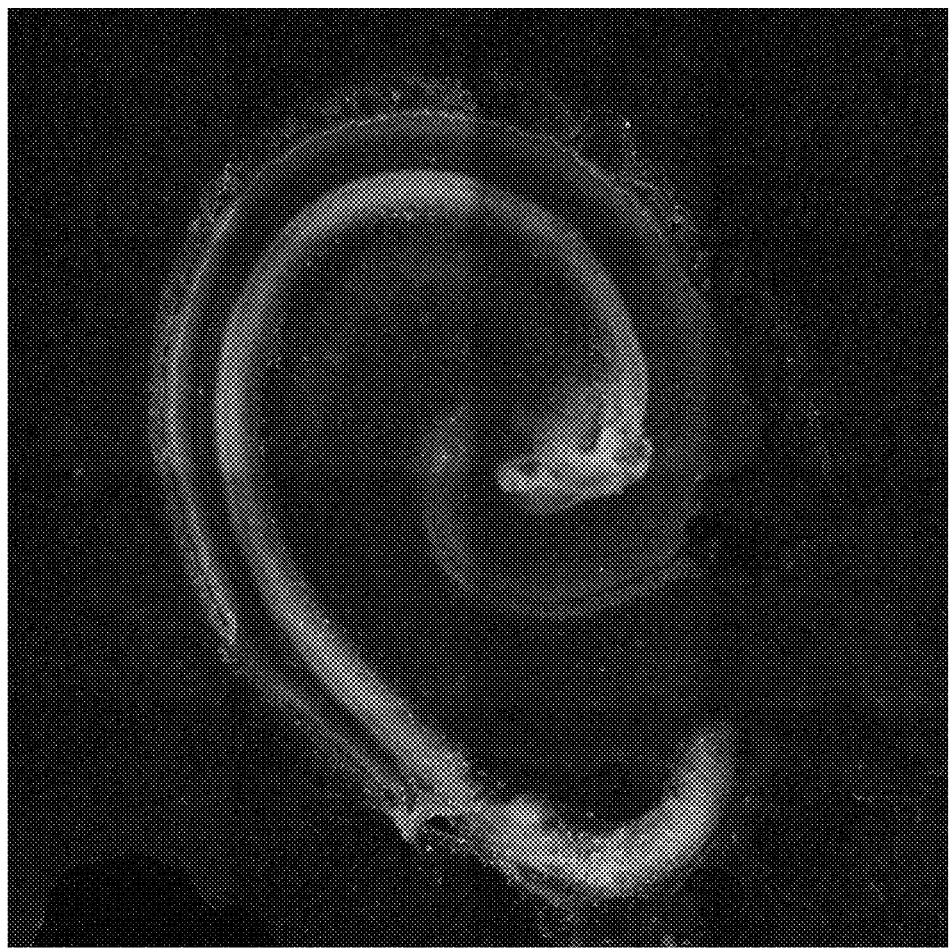
Figure 11E:
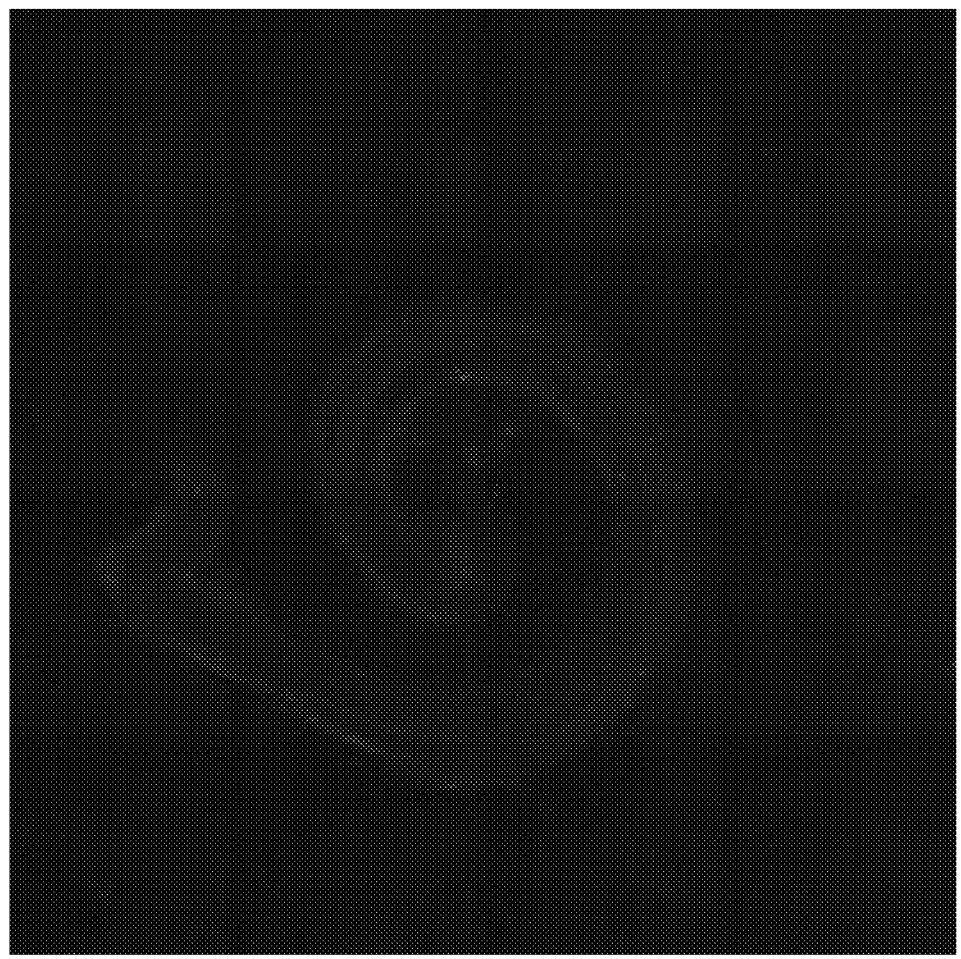
Figure 11F:
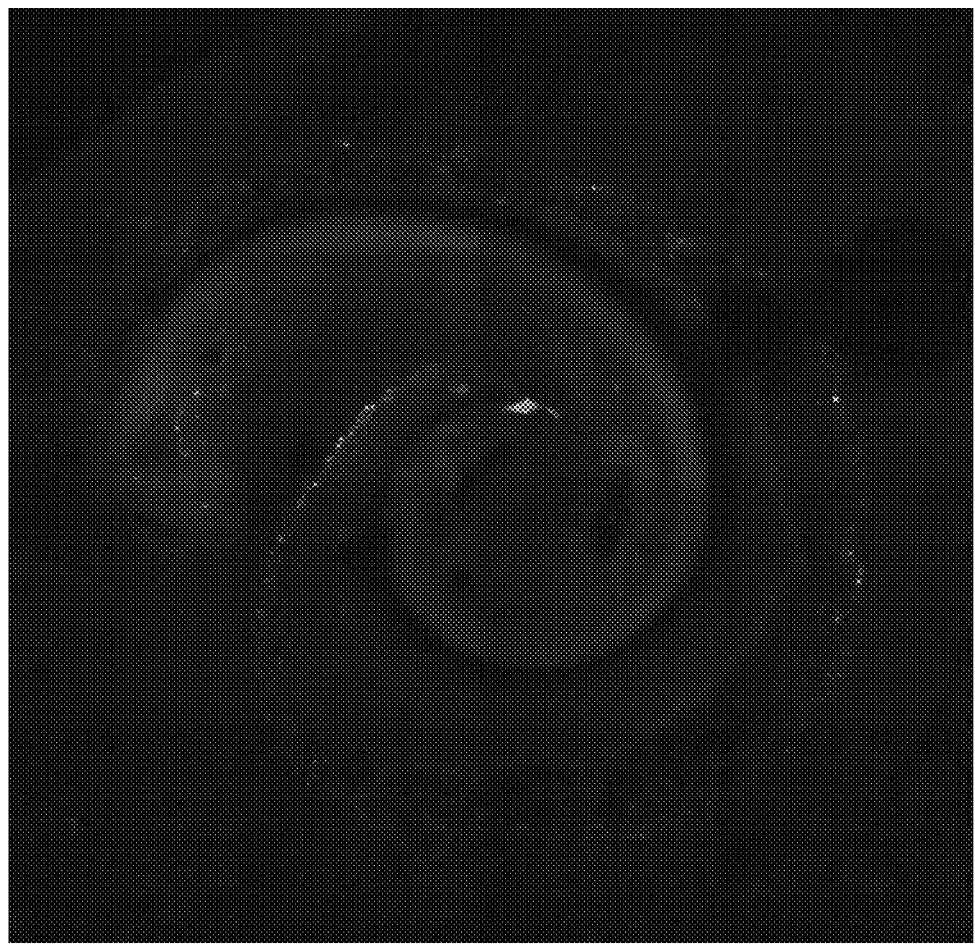
Figure 11G:
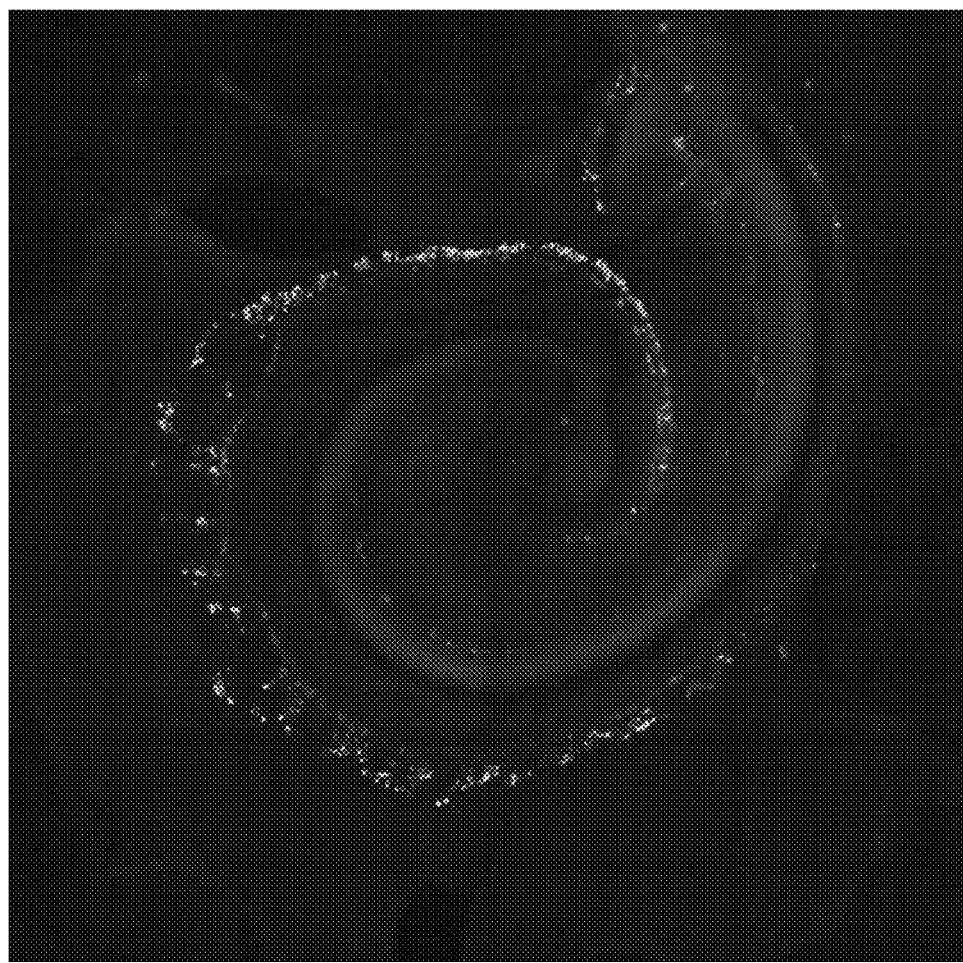
Figure 11H:
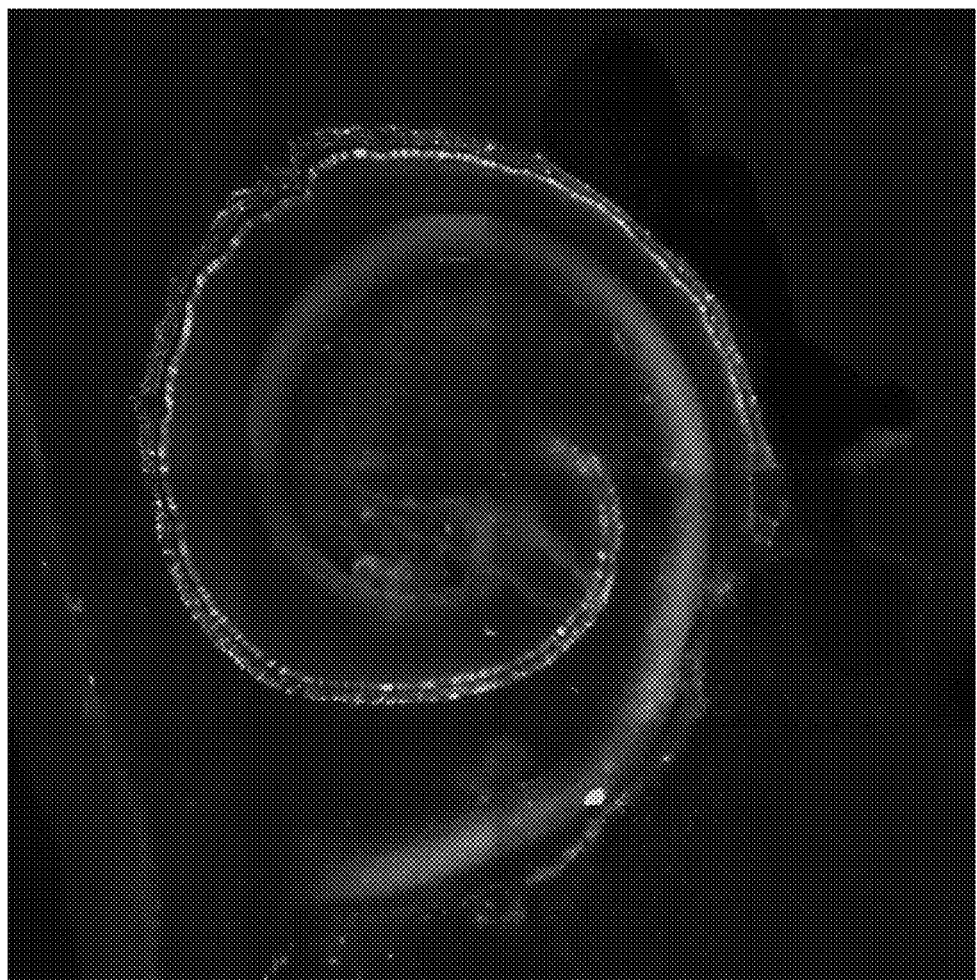
Figure 11I:
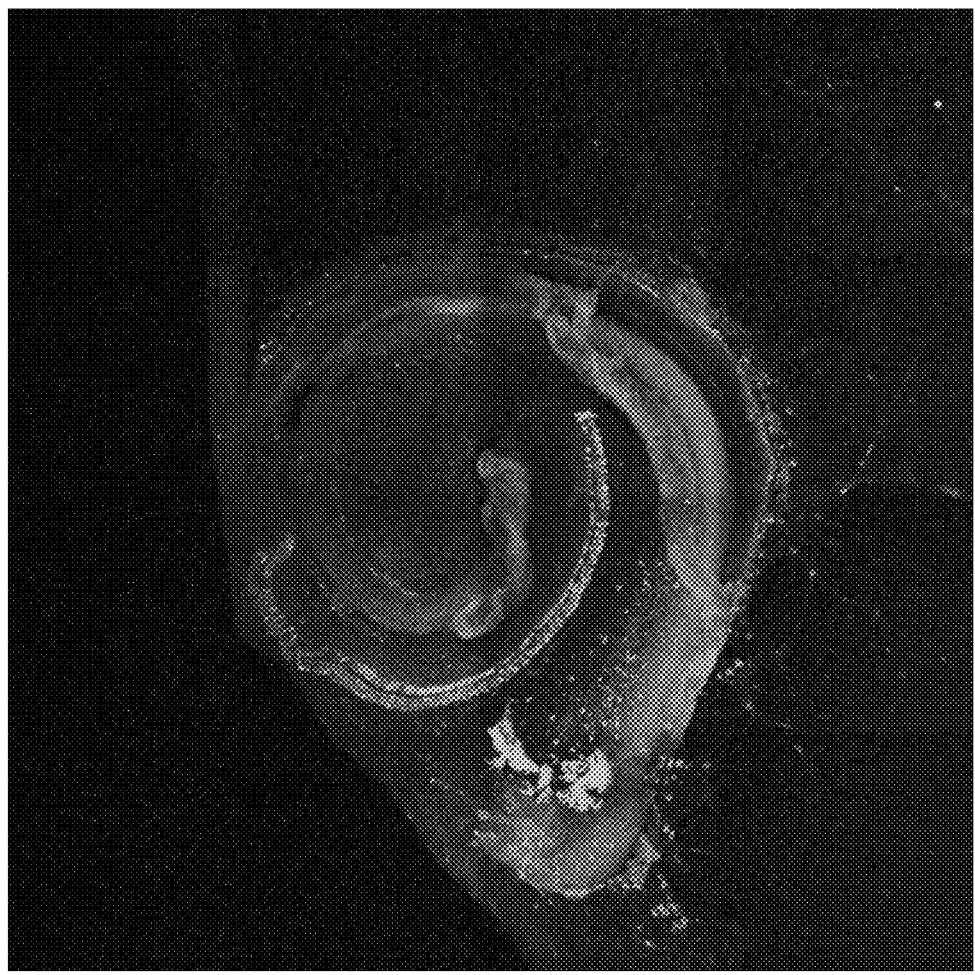
Figure 11J:
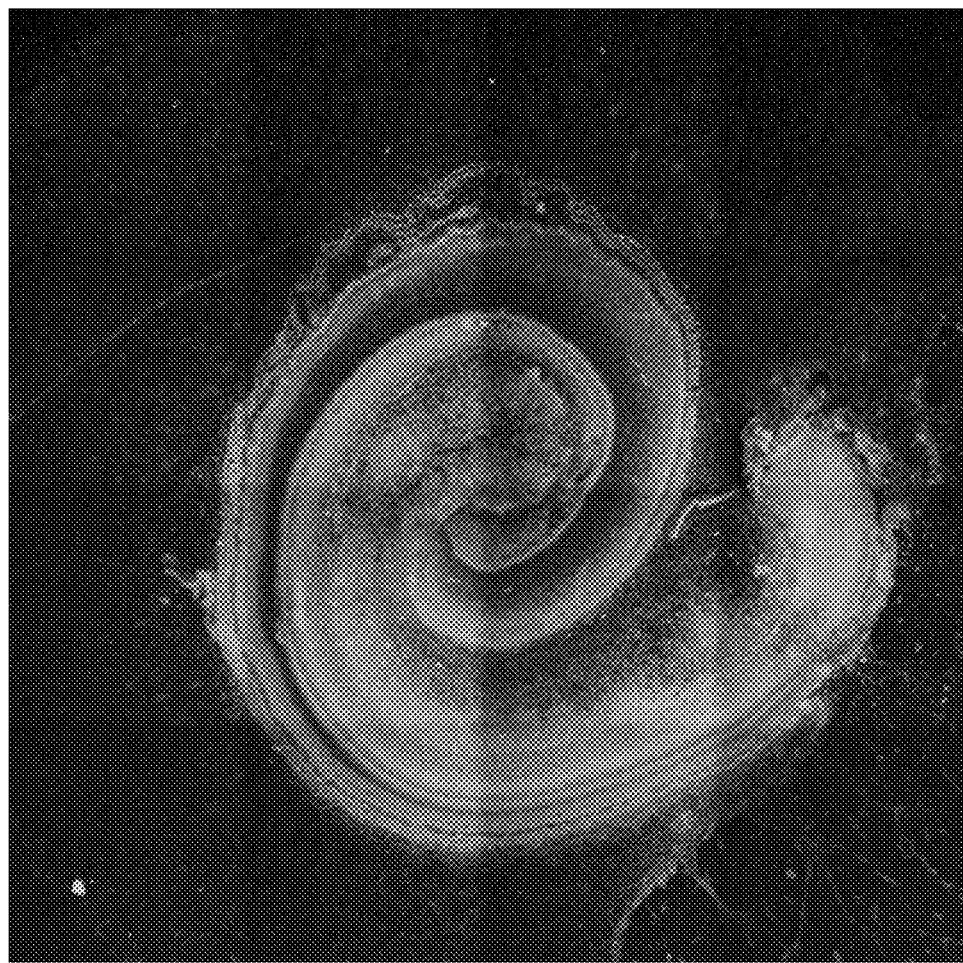

Analysis of whole mount images of neonatal cochlear explant cultures infected with a subset of the Myo15 promoter variants described in Table 2 demonstrated that the promoter sequence of SEQ ID NO: 27 (Myo15 A) was neither sufficient nor necessary for general promoter activity or hair cell specificity as shown in FIGS. 11B (SEQ ID NO: 27), 11E (SEQ ID NO: 30), 11F (SEQ ID NO: 31), and 11G (SEQ ID NO: 32). The promoter sequence of SEQ ID NO: 27 did provide a splice donor site that increased expression levels when paired with a splice acceptor site as shown in FIGS. 11A (SEQ ID NO: 16) and 11H (SEQ ID NO: 33), thus introducing an intron into the promoter sequence. The promoter sequence of SEQ ID NO: 28 (Myo15 B) alone was found to be a core promoter that conferred general promoter activity as shown in FIG. 11C (SEQ ID NO: 28), but did not drive hair cell-specific GFP expression in the absence of the promoter sequence of SEQ ID NO: 29 (Myo15 C) as shown in FIGS. 11C (SEQ ID NO: 29) and 11G (SEQ ID NO: 32). The promoter sequence of SEQ ID NO: 29 (Myo15 C) was found to be an enhancer that restricted activity of the core promoter (SEQ ID NO: 28) to inner and outer hair cells as shown in FIG. 11G (SEQ ID NO: 32), but was not sufficient for general promoter activity in the absence of the core promoter as shown in FIG. 11D (SEQ ID NO: 29). The promoter sequences of SEQ ID NO: 27, SEQ ID NO: 28, and SEQ ID NO: 29 were reordered into various combinations and still resulted in hair cell specific promoter activity as shown in FIGS. 11H (SEQ ID NO: 33) and 11I (SEQ ID NO: 34), although not all rearrangements were tolerated, as shown in FIG. 11J (SEQ ID NO: 35). These data are summarized in Table 3, below.

TABLE 3

Promoter activity and hair cell specificity of murine Myo15 promoters

| Promoter | Size (bp) | Promoter activity | Hair cell specificity |
|---|---|---|---|
| A-B-C (SEQ ID NO: 16) | 520 | Yes | Yes |
| A (SEQ ID NO: 27) | 240 | No | n/a |
| B (SEQ ID NO: 28) | 95 | Yes | No |
| C (SEQ ID NO: 29) | 185 | No | n/a |
| A-B (SEQ ID NO: 30) | 335 | No | n/a |
| A-C (SEQ ID NO: 31) | 425 | No | n/a |
| B-C (SEQ ID NO: 32) | 280 | Yes | Yes |
| B-A-C (SEQ ID NO: 33) | 520 | Yes | Yes |
| C-A-B (SEQ ID NO: 34) | 520 | Yes | Yes |
| B-C-A (SEQ ID NO: 35) | 520 | No | n/a |

Figure 12:
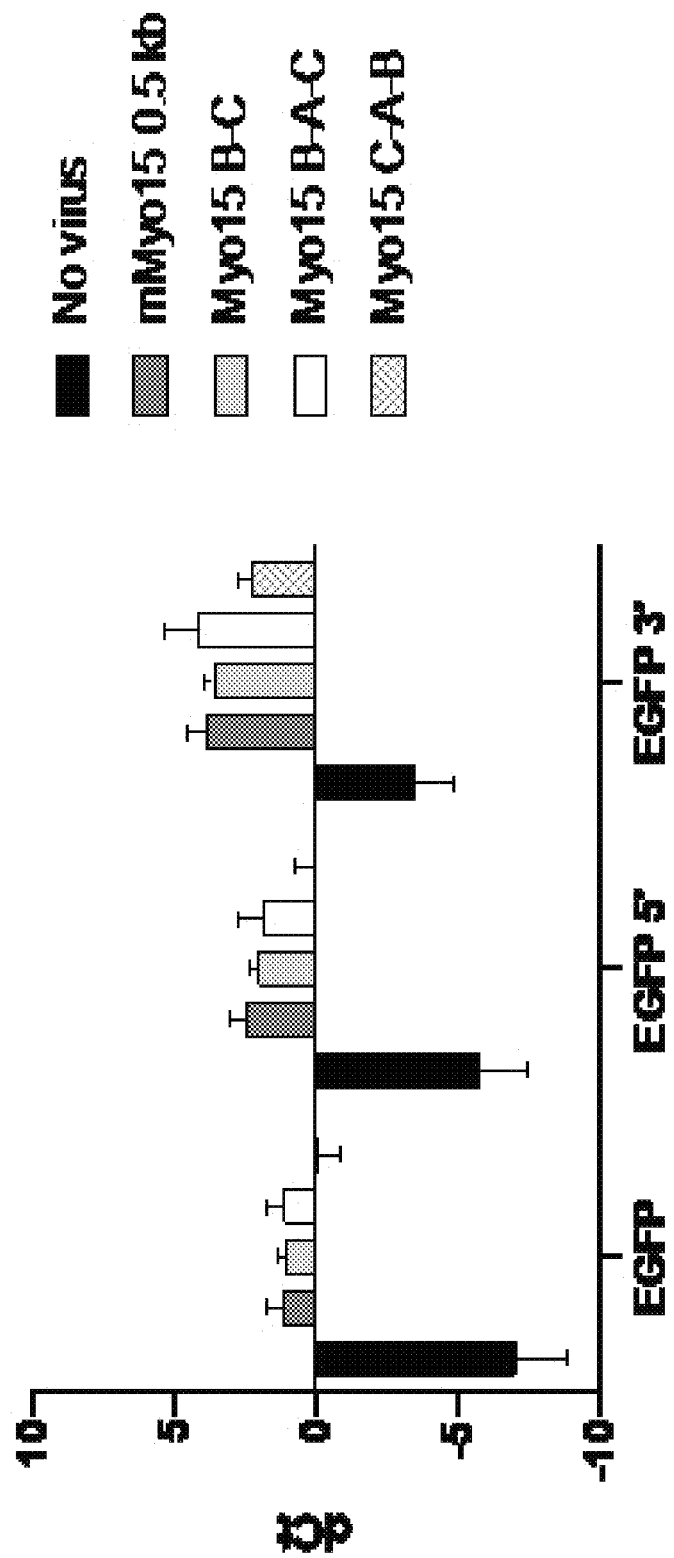
FIG. 12 is a bar plot showing the quantification of GFP expression from promoter variants with hair cell specific expression as measured by qPCR. Transcript levels were normalized to the hair cell specific gene Myo7a. Expression levels of the GFP reporter from the Myo15 0.5 kb (SEQ ID NO: 16), Myo15 B-C(SEQ ID NO: 32), and Myo15 B-A-C(SEQ ID NO: 33) promoters were comparable to each other and robust. The Myo15 C-A-B promoter (SEQ ID NO: 34) was generated by rearranging positions of the splice donor and acceptor sites, resulting in cryptic splicing into the middle of the GFP cDNA as evidenced by the higher expression levels detected with GFP probes located in the 3' end of the transcript versus the 5' end or middle of the transcript.

Myo15 promoter activity was further assessed to determine the strength of expression of Myo15 promoter variants that exhibited hair cell specificity, including the Myo15 0.5 kb (SEQ ID NO: 16), Myo15 B-C(SEQ ID NO: 32), and Myo15 B-A-C(SEQ ID NO: 33). Expression levels of the GFP reporter from the Myo15 0.5 kb, Myo15 B-C, and Myo15 B-A-C promoters were robust and comparable to each other. The Myo15 C-A-B promoter was generated by rearranging positions of the splice donor and acceptor sites and resulted in cryptic splicing into the middle of the GFP cDNA, as evidenced by higher expression levels detected with GFP probes located in the 3' end of the transcript versus the 5' end of the transcript (FIG. 12).

Figure 13A:
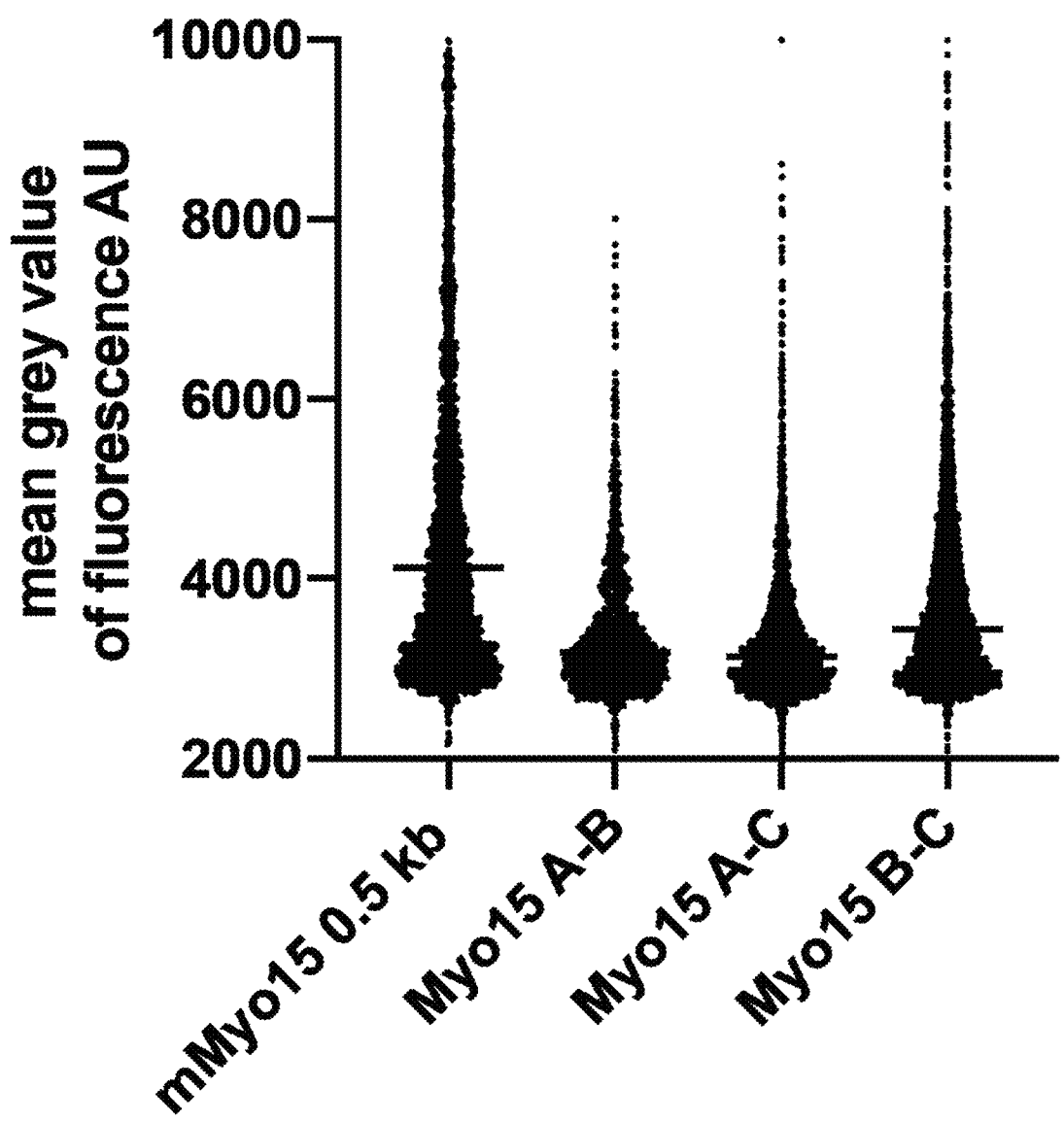
FIGS. 13A-13B are a series of graphs showing quantitative image analysis of GFP expression levels in Myo7a-positive hair cells. Expression levels of GFP protein per cell showed differences in expression between Myo15 promoters (FIGS. 13A-13B), including the 0.5 kb mMyo15 promoter (also referred to as a Myo15 A-B-C promoter; SEQ ID NO: 16), Myo15 A-B promoter (SEQ ID NO: 30), Myo15 A-C promoter (SEQ ID NO: 31), Myo15 B-C promoter (SEQ ID NO: 32), Myo15 A promoter (SEQ ID NO: 27), Myo15 B promoter (SEQ ID NO: 28), Myo15 C promoter (SEQ ID NO: 29), Myo15 B-A-C promoter (SEQ ID NO: 33), Myo15 C-A-B promoter (SEQ ID NO: 34), and the Myo15 B-C-A promoter (SEQ ID NO: 35). The Myo15 A-B-C promoter (SEQ ID NO: 16) yielded the highest expression of GFP per cell (FIG. 13A). Background levels of fluorescence were determined per dataset based on autofluorescence of tissues (<2000 units for FIG. 13A and <6000 units for FIG. 13B).
Figure 13B:
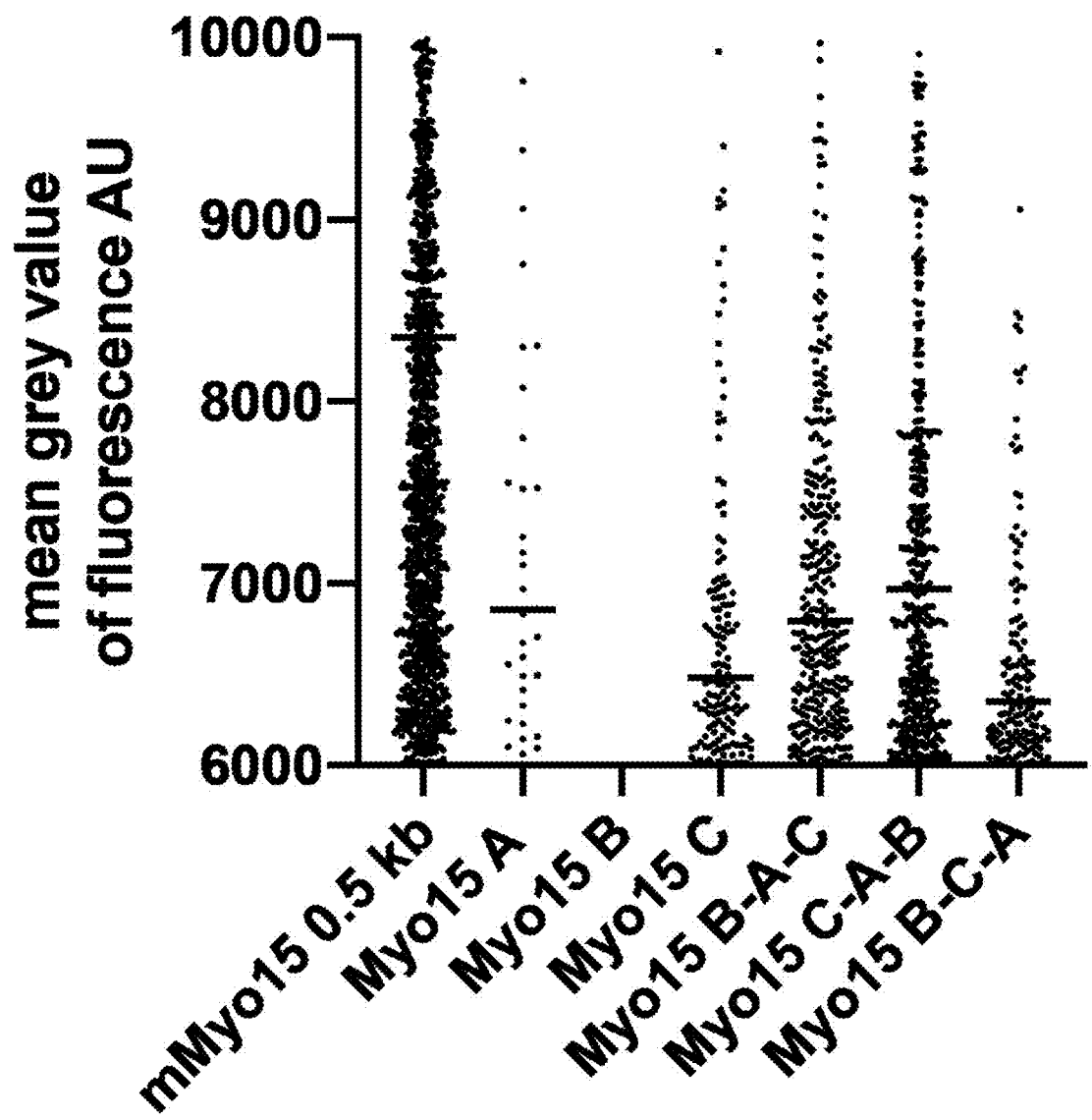

Quantitative image analysis of GFP expression levels was performed in Myo7a-positive hair cells to assess expression levels of GFP per hair cell for various Myo15 promoters, including the 0.5 kb mMyo15 promoter (also referred to as a Myo15 A-B-C promoter; SEQ ID NO: 16), Myo15 A-B promoter (SEQ ID NO: 30), Myo15 A-C promoter (SEQ ID NO: 31), Myo15 B-C promoter (SEQ ID NO: 32), Myo15 A promoter (SEQ ID NO: 27), Myo15 B promoter (SEQ ID NO: 28), Myo15 C promoter (SEQ ID NO: 29), Myo15 B-A-C promoter (SEQ ID NO: 33), Myo15 C-A-B promoter (SEQ ID NO: 34), and the Myo15 B-C-A promoter (SEQ ID NO: 35). The Myo15 A-B-C promoter (SEQ ID NO: 16) yielded the highest expression of GFP per cell (FIG. 13A). Background levels of fluorescence were determined per dataset based on autofluorescence of tissues (<2000 units for FIG. 13A and <6000 units for FIG. 13B).

OTHER EMBODIMENTS

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention. Other embodiments are in the claims.

The invention claimed is:

1. A polynucleotide having at least 85% sequence identity to SEQ ID NO: 15.

2. A nucleic acid vector comprising the polynucleotide of claim 1.

3. The nucleic acid vector of claim 2, wherein the polynucleotide is operably linked to a transgene.

4. The nucleic acid vector of claim 3, wherein the transgene comprises a nucleic acid sequence encoding a therapeutic protein.

5. The nucleic acid vector of claim 4, wherein the therapeutic protein is encoded by a gene selected from the group consisting of ACTG1, FSCN2, RDX, POU4F3, TRIOBP, TPRN, XIRP2, ATOH1, GFI1, CHRNA9, CIB3, CDH23, PCDH15, KNCN, DFNB59, OTOF, MKRN2OS, LHX3, TMC1, MYO15, MYO7A, MYO6, MYO3A, MYO3B, GRXCR1, PTPRQ, LCE6A, LOXHD1, ART1, ATP2B2, CIB2, CACNA2D4, CABP2, EPS8, EPS8L2, ESPN, ESPNL, PRPH2, STRC, SLC8A2, ZCCHC12, LRTOMT2, LRTOMT1, USH1C, ELFN1, TTC24, DYTN, KCP, CCER2, LRTM2, KCNA10, NTF3, CLRN1, CLRN2, SKOR1, TCTEX1D1, FCRLB, SLC17A8, GRXCR2, BDNF, SERPINE3, NHLH1, HSP70, HSP90, ATF6, PERK, IRE1, and BIP.

6. A method of expressing a therapeutic protein in a mammalian hair cell, comprising contacting the mammalian hair cell with the nucleic acid vector of claim 4.

7. A method of treating a subject having or at risk of developing hearing loss, comprising administering to the subject an effective amount of the nucleic acid vector of claim 3.

8. A method of treating a subject having or at risk of developing vestibular dysfunction, comprising administering to the subject an effective amount of the nucleic acid vector of claim 3.

9. A method of promoting hair cell regeneration in a subject in need thereof, comprising administering to the subject an effective amount of the nucleic acid vector of claim 3.

10. A method of treating a subject having tinnitus, comprising administering to the subject an effective amount of the nucleic acid vector of claim 3.

11. The nucleic acid vector of claim 2, wherein the vector is an adeno-associated virus vector.

12. The polynucleotide of claim 1, wherein the polynucleotide has at least 95% sequence identity to SEQ ID NO: 15.

13. The polynucleotide of claim 12, wherein the polynucleotide has the sequence of SEQ ID NO: 15.

* * * * *

SEQUENCE LISTING

<160> NUMBER OF SEQ ID NOS: 37

<210> SEQ ID NO 1
<211> LENGTH: 454
<212> TYPE: DNA
<213> ORGANISM: Mus musculus

<400> SEQUENCE: 1

```
ctgcagctca gcctactact tgctttccag gctgttccta gttcccatgt cagctgcttg      60
tgctttccag agacaaaaca ggaataatag atgtcattaa atatacattg ggccccaggc     120
ggtcaatgtg gcagcctgag cctcctttcc atctctgtgg aggcagacat aggaccccca     180
acaaacagca tgcaggttgg gagccagcca caggacccag gtaaggggcc ctgggtcctt     240
aagcttctgc cactggctcc ggcattgcag agagaagaga aggggcggca gagctgaacc     300
ttagccttgc cttcctgggt acccttctga gcctcactgt cttctgtgag atgggcaaag     360
tgcgggtgtg actccttggc aacggtgtta caccagggca ggtaaagttg tagttatttg     420
tggggtacac caggactgtt aaaggtgtaa ctat                                 454
```

<210> SEQ ID NO 2
<211> LENGTH: 1157
<212> TYPE: DNA
<213> ORGANISM: Mus musculus

<400> SEQUENCE: 2

```
ggtctcaccc agcattttca cttctaataa gttcaaatgt gatacggcac ctttctaaaa      60
attagttttc agggaaatag ggttcaaaac tggtagtggt agggtccatt ctcacgaccc     120
ccaggcctgc taaccctgac caagctacct attacttacc ctcctctttc tcctcctcct     180
ctttctcctt ctcctgcttc ccctcttcct tctccctccc ttcctctccc tcctcccct      240 ccttggctgt gatcagatcc agagcctgaa tgagcctcct gaccccacac ccccactagc     300
atgggcctgc aagtgcccag aagtccctcc tgcctcctaa actgcccagc cgatccatta     360
gctcttcctt cttcccagtg aaagaagcag gcacagcctg tccctcccgt tctacagaaa     420
ggaagctaca gcacagggag ggccaaaggc cttcctggga ctagacagtt gatcaacagc     480
aggactggag agctgggctc cattttttgtt ccttggtgcc ctgcccctcc ccatgacctg     540
cagagacatt cagcctgcca ggctttatga ggtgggagct gggctctccc tgatgtatta     600
```

```
ttcagctccc tggagttggc cagctcctgt tacactggcc acagccctgg gcatccgctt        660
ctcacttcta gtttcccctc caaggtaatg tggtgggtca tgatcattct atcctggctt        720
cagggacctg actccacttt ggggccattc gagggtcta ggtagatga tgtcccctg           780 tggggattaa tgtcctgctc tgtaaaactg agctagctga gatccaggag gcttggcca         840 gagacagcaa gttgttgcca tggtgactt aaagccaggt tgctgcccca gcacaggcct         900
cccagtctac cctcactaga aacaacacc caggcactt  ccaccctc  tcaaaggtga          960 aacccaaggc tggtctagag aatgaattat ggatcctcgc tgtccgtgcc acccagctag       1020
tcccagcggc tcagacactg aggagagact gtaggttcag ctacaagcaa aaagacctag       1080
ctggtctcca agcagtgtct ccaagtccct gaacctgtga cacctgcccc aggcatcatc      1140
aggcacagag ggccacc                                                      1157

<210> SEQ ID NO 3
<211> LENGTH: 76
<212> TYPE: DNA
<213> ORGANISM: Mus musculus

<400> SEQUENCE: 3
cccatgtcag ctgcttgtgc tttccagaga caaaacagga ataatagatg tcattaaata        60
tacattgggc cccagg                                                        76

<210> SEQ ID NO 4
<211> LENGTH: 95
<212> TYPE: DNA
<213> ORGANISM: Mus musculus

<400> SEQUENCE: 4
agcctgagcc tcctttccat ctctgtggag gcagacatag gaccccaac aaacagcatg         60 caggttggga gccagccaca ggacccaggt aaggg                                   95

<210> SEQ ID NO 5
<211> LENGTH: 171
<212> TYPE: DNA
<213> ORGANISM: Artificial Sequence
<220> FEATURE:
<223> OTHER INFORMATION: Synthetic Construct

<400> SEQUENCE: 5
cccatgtcag ctgcttgtgc tttccagaga caaaacagga ataatagatg tcattaaata        60
tacattgggc cccaggagcc tgagcctcct ttccatctct gtggaggcag acataggacc       120
cccaacaaac agcatgcagg ttgggagcca gccacaggac ccaggtaagg g                171

<210> SEQ ID NO 6
<211> LENGTH: 171
<212> TYPE: DNA
<213> ORGANISM: Artificial Sequence
<220> FEATURE:
<223> OTHER INFORMATION: Synthetic Construct

<400> SEQUENCE: 6
agcctgagcc tcctttccat ctctgtggag gcagacatag gaccccaac aaacagcatg         60 caggttggga gccagccaca ggacccaggt aagggcccat gtcagctgct tgtgctttcc       120
agagacaaaa caggaataat agatgtcatt aaatatacat tgggccccag g                171

<210> SEQ ID NO 7
<211> LENGTH: 184
```

```
<212> TYPE: DNA
<213> ORGANISM: Mus musculus

<400> SEQUENCE: 7
cccatgtcag ctgcttgtgc tttccagaga caaaacagga ataatagatg tcattaaata    60
tacattgggc cccaggcggt caatgtggca gcctgagcct cctttccatc tctgtggagg   120
cagacatagg accccaaca aacagcatgc aggttgggag ccagccacag gacccaggta    180
aggg                                                                184

<210> SEQ ID NO 8
<211> LENGTH: 82
<212> TYPE: DNA
<213> ORGANISM: Mus musculus

<400> SEQUENCE: 8
tgaggtggga gctgggctct ccctgatgta ttattcagct ccctggagtt ggccagctcc    60
tgttacactg gccacagccc tg                                             82

<210> SEQ ID NO 9
<211> LENGTH: 106
<212> TYPE: DNA
<213> ORGANISM: Mus musculus

<400> SEQUENCE: 9
cacaggcctc ccagtctacc ctcactagaa acaacaccc aggcactttc caccacctct    60
caaaggtgaa acccaaggct ggtctagaga atgaattatg gatcct                  106

<210> SEQ ID NO 10
<211> LENGTH: 188
<212> TYPE: DNA
<213> ORGANISM: Artificial Sequence
<220> FEATURE:
<223> OTHER INFORMATION: Synthetic Construct

<400> SEQUENCE: 10
tgaggtggga gctgggctct ccctgatgta ttattcagct ccctggagtt ggccagctcc    60
tgttacactg gccacagccc tgcacaggcc tcccagtcta ccctcactag aaaacaacac   120
ccaggcactt tccaccacct ctcaaaggtg aaacccaagg ctggtctaga gaatgaatta   180
tggatcct                                                            188

<210> SEQ ID NO 11
<211> LENGTH: 188
<212> TYPE: DNA
<213> ORGANISM: Artificial Sequence
<220> FEATURE:
<223> OTHER INFORMATION: Synthetic Construct

<400> SEQUENCE: 11
cacaggcctc ccagtctacc ctcactagaa acaacaccc aggcactttc caccacctct    60
caaaggtgaa acccaaggct ggtctagaga atgaattatg gatccttgag gtgggagctg   120
ggctctccct gatgtattat tcagctccct ggagttggcc agctcctgtt acactggcca   180
cagccctg                                                            188

<210> SEQ ID NO 12
<211> LENGTH: 430
<212> TYPE: DNA
<213> ORGANISM: Mus musculus
```

<400> SEQUENCE: 12

```
tgaggtggga gctgggctct ccctgatgta ttattcagct ccctggagtt ggccagctcc    60
tgttacactg gccacagccc tgggcatccg cttctcactt ctagtttccc ctccaaggta   120
atgtggtggg tcatgatcat tctatcctgg cttcagggac ctgactccac tttggggcca   180
ttcgagggt ctagggtaga tgatgtcccc ctgtgggat taatgtcctg ctctgtaaaa     240
ctgagctagc tgagatccag gagggcttgg ccagagacag caagttgttg ccatggtgac   300
tttaaagcca ggttgctgcc ccagcacagg cctcccagtc taccctcact agaaaacaac   360
acccaggcac tttccaccac ctctcaaagg tgaaacccaa ggctggtcta gagaatgaat   420
tatggatcct                                                          430
```

<210> SEQ ID NO 13
<211> LENGTH: 1611
<212> TYPE: DNA
<213> ORGANISM: Artificial Sequence
<220> FEATURE:
<223> OTHER INFORMATION: Synthetic Construct

<400> SEQUENCE: 13

```
ctgcagctca gcctactact tgctttccag gctgttccta gttcccatgt cagctgcttg    60
tgctttccag agacaaaaca ggaataatag atgtcattaa atatacattg ggccccaggc   120
ggtcaatgtg gcagcctgag cctcctttcc atctctgtgg aggcagacat aggaccccca   180
acaaacagca tgcaggttgg gagccagcca caggacccag gtaaggggcc ctgggtcctt   240
aagcttctgc cactggctcc ggcattgcag agagaagaga aggggcggca gagctgaacc   300
ttagccttgc cttcctgggt acccttctga gcctcactgt cttctgtgag atgggcaaag   360
tgcgggtgtg actccttggc aacggtgtta caccagggca ggtaaagttg tagttatttg   420
tggggtacac caggactgtt aaaggtgtaa ctatggtctc acccagcatt ttcacttcta   480
ataagttcaa atgtgatacg gcacctttct aaaaattagt tttcagggaa ataggggttca  540
aaactggtag tggtagggtc cattctcacg acccccaggc ctgctaaccc tgaccaagct   600
acctattact taccctcctc tttctcctcc tcctctttct ccttctcctg cttcccctct   660
tccttctccc tcccttcctc tccctcctcc ccctccttgg ctgtgatcag atccagagcc   720
tgaatgagcc tcctgacccc acaccccac tagcatgggc ctgcaagtgc ccagaagtcc    780
ctcctgcctc ctaaactgcc cagccgatcc attagctctt ccttcttccc agtgaaagaa   840
gcaggcacag cctgtccctc ccgttctaca gaaaggaagc tacagcacag ggagggccaa   900
aggccttcct gggactagac agttgatcaa cagcaggact ggagagctgg gctccatttt   960
tgttccttgg tgccctgccc ctccccatga cctgcagaga cattcagcct gccaggcttt  1020
atgaggtggg agctgggctc tccctgatgt attattcagc tccctggagt tggccagctc  1080
ctgttacact ggccacagcc ctgggcatcc gcttctcact tctagtttcc cctccaaggt  1140
aatgtggtgg gtcatgatca ttctatcctg gcttcaggga cctgactcca ctttggggcc  1200
attcgagggg tctagggtag atgatgtccc cctgtgggga ttaatgtcct gctctgtaaa  1260
actgagctag ctgagatcca ggagggcttg gccagagaca gcaagttgtt gccatggtga  1320
cttttaaagcc aggttgctgc cccagcacag gcctcccagt ctaccctcac tagaaaacaa  1380
cacccaggca ctttccacca cctctcaaag gtgaaaccca aggctggtct agagaatgaa  1440
ttatggatcc tcgctgtccg tgccaccag ctagtcccag cggctcagac actgaggaga   1500
gactgtaggt tcagctacaa gcaaaaagac ctagctggtc tccaagcagt gtctccaagt  1560
```

| ccctgaacct gtgacacctg ccccaggcat catcaggcac agagggccac c | 1611 |

<210> SEQ ID NO 14
<211> LENGTH: 1611
<212> TYPE: DNA
<213> ORGANISM: Artificial Sequence
<220> FEATURE:
<223> OTHER INFORMATION: Synthetic Construct

<400> SEQUENCE: 14

| ggtctcaccc agcattttca cttctaataa gttcaaatgt gatacggcac ctttctaaaa | 60 |
| attagttttc agggaaatag ggttcaaaac tggtagtggg agggtccatt ctcacgaccc | 120 |
| ccaggcctgc taaccctgac caagctacct attacttacc ctcctctttc tcctcctcct | 180 |
| cttctctcctt ctcctgcttc ccctcttcct tctccctccc ttcctctccc tcctccccct | 240 |
| ccttggctgt gatcagatcc agagcctgaa tgagcctcct gaccccacac ccccactagc | 300 |
| atgggcctgc aagtgcccag aagtccctcc tgcctcctaa actgcccagc cgatccatta | 360 |
| gctcttcctt cttcccagtg aaagaagcag gcacagcctg tccctcccgt tctacagaaa | 420 |
| ggaagctaca gcacagggag ggccaaaggc cttcctggga ctagacagtt gatcaacagc | 480 |
| aggactggag agctgggctc cattttttgtt ccttggtgcc ctgcccctcc ccatgacctg | 540 |
| cagagacatt cagcctgcca ggctttatga ggtgggagct gggctctccc tgatgtatta | 600 |
| ttcagctccc tggagttggc cagctcctgt tacactggcc acagcctgg gcatccgctt | 660 |
| ctcacttcta gtttcccctc caaggtaatg tggtgggtca tgatcattct atcctggctt | 720 |
| cagggacctg actccacttt ggggccattc gagggggtcta gggtagatga tgtcccctg | 780 |
| tggggattaa tgtcctgctc tgtaaaactg agctagctga gatccaggag ggcttggcca | 840 |
| gagacagcaa gttgttgcca tggtgactttt aaagccaggt tgctgcccca gcacaggcct | 900 |
| cccagtctac cctcactaga aaacaacacc caggcacttt ccaccacctc tcaaaggtga | 960 |
| aacccaaggc tggtctagag aatgaattat ggatcctcgc tgtccgtgcc acccagctag | 1020 |
| tcccagcggc tcagacactg aggagagact gtaggttcag ctacaagcaa aaagacctag | 1080 |
| ctggtctcca agcagtgtct ccaagtccct gaacctgtga cacctgcccc aggcatcatc | 1140 |
| aggcacagag ggccaccctg cagctcagcc tactacttgc tttccaggct gttcctagtt | 1200 |
| cccatgtcag ctgcttgtgc tttccagaga caaaacagga ataatagatg tcattaaata | 1260 |
| tacattgggc cccaggcggt caatgtggca gcctgagcct cctttccatc tctgtggagg | 1320 |
| cagacatagg accccaaca aacagcatgc aggttgggag ccagccacag gacccaggta | 1380 |
| agggccctg ggtccttaag cttctgccac tggctccggc attgcagaga gaagagaagg | 1440 |
| ggcggcagag ctgaaccta gccttgcctt cctgggtacc cttctgagcc tcactgtctt | 1500 |
| ctgtgagatg ggcaaagtgc gggtgtgact ccttggcaac ggtgttacac cagggcaggt | 1560 |
| aaagttgtag ttatttgtgg ggtacaccag gactgttaaa ggtgtaacta t | 1611 |

<210> SEQ ID NO 15
<211> LENGTH: 965
<212> TYPE: DNA
<213> ORGANISM: Artificial Sequence
<220> FEATURE:
<223> OTHER INFORMATION: Synthetic Construct

<400> SEQUENCE: 15

| ctgcagctca gcctactact tgctttccag gctgttccta gttcccatgt cagctgcttg | 60 |

```
tgcttttccag agacaaaaca ggaataatag atgtcattaa atatacattg ggccccaggc    120
ggtcaatgtg gcagcctgag cctcctttcc atctctgtgg aggcagacat aggaccccca    180
acaaacagca tgcaggttgg gagccagcca caggacccag gtaaggggcc ctgggtcctt    240
aagcttctgc cactggctcc ggcattgcag agagaagaga aggggcggca gactggagag    300
ctgggctcca tttttgttcc ttggtgccct gcccctcccc atgacctgca gagacattca    360
gcctgccagg ctttatgagg tgggagctgg gctctccctg atgtattatt cagctccctg    420
gagttggcca gctcctgtta cactggccac agccctgggc atccgcttct cacttctagt    480
ttcccctcca aggtaatgtg gtgggtcatg atcattctat cctggcttca gggacctgac    540
tccactttgg ggccattcga ggggtctagg gtagatgatg tcccctgtg gggattaatg    600 tcctgctctg taaaactgag ctagctgaga tccaggaggg cttggccaga gacagcaagt    660
tgttgccatg gtgactttaa agccaggttg ctgcccagc acaggcctcc cagtctaccc    720
tcactagaaa acaacaccca ggcactttcc accacctctc aaaggtgaaa cccaaggctg    780
gtctagagaa tgaattatgg atcctcgctg tccgtgccac ccagctagtc ccagcggctc    840
agacactgag gagagactgt aggttcagct acaagcaaaa agacctagct ggtctccaag    900
cagtgtctcc aagtccctga acctgtgaca cctgccccag gcatcatcag gcacagaggg    960
ccacc                                                                965

<210> SEQ ID NO 16
<211> LENGTH: 520
<212> TYPE: DNA
<213> ORGANISM: Artificial Sequence
<220> FEATURE:
<223> OTHER INFORMATION: Synthetic Construct

<400> SEQUENCE: 16
ctgcagctca gcctactact tgctttccag gctgttccta gttcccatgt cagctgcttg     60
tgctttccag agacaaaaca ggaataatag atgtcattaa atatacattg ggccccaggc    120
ggtcaatgtg gcagcctgag cctcctttcc atctctgtgg aggcagacat aggaccccca    180
acaaacagca tgcaggttgg gagccagcca caggacccag gtaaggggcc ctgggtcctt    240
tttatgaggt gggagctggg ctctccctga tgtattattc agctccctgg agttggccag    300
ctcctgttac actggccaca gccctgggca tccgctgcca tggtgacttt aaagccaggt    360
tgctgcccca gcacaggcct cccagtctac cctcactaga aacaacacc caggcactttt   420 ccaccacctc tcaaaggtga aacccaaggc tggtctagag aatgaattat ggatcctcgc    480
tgtccgtgcc acccagctag tcccagcggc tcagacactg                         520

<210> SEQ ID NO 17
<211> LENGTH: 235
<212> TYPE: DNA
<213> ORGANISM: Homo sapiens

<400> SEQUENCE: 17
gtatgccttt tgagatggat gcagcaggtt ctgtgaggct gccaggaggg gtagagttcc     60 cggggggcctc gggcccccgct ggagtgtgga gcaggcccat gctcagctct ccaggctgtt   120
cgtggctccc ctgtcagctg ctcactcctt tccagagaca aaacaggaat aatagacatc    180
attaaatata catagggccc caggcggtcg gcgtggtggg ctgggcctcc cttcc          235

<210> SEQ ID NO 18
<211> LENGTH: 688
```

```
<212> TYPE: DNA
<213> ORGANISM: Homo sapiens

<400> SEQUENCE: 18
tgccctgcct tctgagccgg cagcctggct ccccacccca tgtattattc agctcctgag      60
agccagccag ctcctgttac actgaccgca gcccagcacc tgctctgccc attcccctcc     120
tcccttgcct aggacctaga gggttcaaag ttctcctcca agatgacttg gtgggctttg     180
gccatcccac cctaggcccc acttctggcc cagtgcaggt gtgctggtga tttagggcag     240
gtggcattcc atctctgtgg ctcaatgtct tcctctgtga agccgaagtg acccaagggc     300
tcccttcatg gggttgagcc agctgtggcc cagggagggc ctaaccagga tgagcactga     360
tgttgccatg acgactccga ggccagaatg tctcccccag cacaggcctc ataggcaggc     420
ttccccatcc tggtaaacaa cacccacaca ctttctacta ctgctctagg gtgaaaccca     480
aggcgctcta gaggagatga attatggatc cgccctcccg gaatcctggc tcggccctcc     540
ccacgccacc cagggccagt cgggtctgct cacagcccga ggaggccgcg tgtccagccg     600
cgggcaagag acagagcagg tccctgtgtc tccaagtccc tgagcccgtg acaccggccc     660
caggccctgt agagagcagg cagccacc                                        688

<210> SEQ ID NO 19
<211> LENGTH: 77
<212> TYPE: DNA
<213> ORGANISM: Homo sapiens

<400> SEQUENCE: 19
cccctgtcag ctgctcactc ctttccagag acaaaacagg aataatagac atcattaaat      60
atacataggg cccagg                                                      77

<210> SEQ ID NO 20
<211> LENGTH: 82
<212> TYPE: DNA
<213> ORGANISM: Homo sapiens

<400> SEQUENCE: 20
tgagccggca gcctggctcc caccccatg tattattcag ctcctgagag ccagccagct       60
cctgttacac tgaccgcagc cc                                               82

<210> SEQ ID NO 21
<211> LENGTH: 111
<212> TYPE: DNA
<213> ORGANISM: Homo sapiens

<400> SEQUENCE: 21
cacaggcctc ataggcaggc ttccccatcc tggtaaacaa cacccacaca ctttctacta      60
ctgctctagg gtgaaaccca aggcgctcta gaggagatga attatggatc c              111

<210> SEQ ID NO 22
<211> LENGTH: 193
<212> TYPE: DNA
<213> ORGANISM: Artificial Sequence
<220> FEATURE:
<223> OTHER INFORMATION: Synthetic Construct

<400> SEQUENCE: 22
tgagccggca gcctggctcc caccccatg tattattcag ctcctgagag ccagccagct       60
cctgttacac tgaccgcagc cccacaggcc tcataggcag gcttccccat cctggtaaac    120
```

```
aacacccaca cactttctac tactgctcta gggtgaaacc caaggcgctc tagaggagat    180
gaattatgga tcc                                                       193

<210> SEQ ID NO 23
<211> LENGTH: 193
<212> TYPE: DNA
<213> ORGANISM: Artificial Sequence
<220> FEATURE:
<223> OTHER INFORMATION: Synthetic Construct

<400> SEQUENCE: 23
cacaggcctc ataggcaggc ttccccatcc tggtaaacaa cacccacaca ctttctacta     60
ctgctctagg gtgaaaccca aggcgctcta gaggagatga attatggatc ctgagccggc    120
agcctggctc cccaccccat gtattattca gctcctgaga gccagccagc tcctgttaca    180
ctgaccgcag ccc                                                       193

<210> SEQ ID NO 24
<211> LENGTH: 499
<212> TYPE: DNA
<213> ORGANISM: Homo sapiens

<400> SEQUENCE: 24
tgagccggca gcctggctcc ccaccccatg tattattcag ctcctgagag ccagccagct     60
cctgttacac tgaccgcagc cagcacctg ctctgcccat tccctcctc ccttgcctag     120 gacctagagg gttcaaagtt ctcctccaag atgacttggt gggctttggc catcccaccc    180
taggccccac ttctggccca gtgcaggtgt gctggtgatt tagggcaggt ggcattccat    240
ctctgtggct caatgtcttc ctctgtgaag ccgaagtgac ccaagggctc ccttcatggg    300
gttgagccag ctgtggccca gggagggcct aaccaggatg agcactgatg ttgccatgac    360
gactccgagg ccagaatgtc tccccagca caggcctcat aggcaggctt ccccatcctg    420
gtaaacaaca cccacacact ttctactact gctctagggt gaaacccaag gcgctctaga    480
ggagatgaat tatggatcc                                                 499

<210> SEQ ID NO 25
<211> LENGTH: 1262
<212> TYPE: DNA
<213> ORGANISM: Artificial Sequence
<220> FEATURE:
<223> OTHER INFORMATION: Synthetic Construct

<400> SEQUENCE: 25
gtatgccttt tgagatggat gcagcaggtt ctgtgaggct gccaggaggg gtagagttcc     60
cgggggcctc gggccccgct ggagtgtgga gcaggcccat gctcagctct ccaggctgtt    120
cgtggctccc ctgtcagctg ctcactcctt tccagagaca aaacaggaat aatagacatc    180
attaaatata catagggccc caggcggtcg gcgtggtggg ctgggcctcc cttccccata    240
acactgagct gctctgctgg gccaaccgtg ctcctgggcc agccagagga cccccatgag    300
gcggcatgca ggcggggagc aggccacaga acgcaggtaa ggagaccttta gcctagagtc    360 cttgggggtct gtcactggcc accctcgcat cccaggctgc aggaaactga gcccagaga    420 ggacaaggac tttcctggac ccacacagcc agtcagtgac agagcctagg gtctgagcca    480
ggcctgaccc aacctccatt tctgcctctc taccccctgcc ccgcccaa cacacacaca    540 cacacaagtg gagttccact gaaacgcccc tccttgccct gccttctgag ccggcagcct    600
ggctccccac cccatgtatt attcagctcc tgagagccag ccagctcctg ttacactgac    660
```

```
cgcagcccag cacctgctct gcccattccc ctcctccctt gcctaggacc tagagggttc    720
aaagttctcc tccaagatga cttggtgggc tttggccatc ccaccctagg ccccacttct    780
ggcccagtgc aggtgtgctg gtgatttagg gcaggtggca ttccatctct gtggctcaat    840
gtcttcctct gtgaagccga agtgacccaa gggctccctt catggggttg agccagctgt    900
ggcccaggga gggcctaacc aggatgagca ctgatgttgc catgacgact ccgaggccag    960
aatgtctccc ccagcacagg cctcataggc aggcttcccc atcctggtaa acaacaccca   1020
cacactttct actactgctc tagggtgaaa cccaaggcgc tctagaggag atgaattatg   1080
gatccgccct cccggaatcc tggctcggcc ctccccacgc cacccagggc cagtcgggtc   1140
tgctcacagc ccgaggaggc cgcgtgtcca gccgcgggca agagacagag caggtccctg   1200
tgtctccaag tccctgagcc cgtgacaccg gccccaggcc ctgtagagag caggcagcca   1260
cc                                                                 1262

<210> SEQ ID NO 26
<211> LENGTH: 649
<212> TYPE: DNA
<213> ORGANISM: Artificial Sequence
<220> FEATURE:
<223> OTHER INFORMATION: Synthetic Construct

<400> SEQUENCE: 26
gcaggcccat gctcagctct ccaggctgtt cgtggctccc ctgtcagctg ctcactcctt     60
tccagagaca aaacaggaat aatagacatc attaaatata catagggccc caggcggtcg    120
gcgtggtggg ctgggcctcc cttccccata acactgagct gctctgctgg gccaaccgtg    180
ctcctgggcc agccagagga cccccatgag gcggcatgca ggcggggagc aggccacaga    240
acgcaggtaa ggagaccttg ccttctgagc cggcagcctg gctccccacc ccatgtatta    300
ttcagctcct gagagccagc cagctcctgt tacactgacc gcagcccagc acctgctctg    360
cccattcccc tcctcccttg cctaggacct agagggttca aagttctcct ccaagatgac    420
ttggtgggct ttggccatcg ggcctaacca ggatgagcac tgatgttgcc atgacgactc    480
cgaggccaga atgtctcccc cagcacaggc ctcataggca ggcttcccca tcctggtaaa    540
caacacccac acactttcta ctactgctct agggtgaaac ccaaggcgct ctagaggaga    600
tgaattatgg atccgccctc ccggaatcct ggctcggccc tccccacgc                649

<210> SEQ ID NO 27
<211> LENGTH: 240
<212> TYPE: DNA
<213> ORGANISM: Mus musculus

<400> SEQUENCE: 27
ctgcagctca gcctactact tgctttccag gctgttccta gttcccatgt cagctgcttg     60
tgctttccag agacaaaaca ggaataatag atgtcattaa atatacattg gccccaggc    120 ggtcaatgtg gcagcctgag cctcctttcc atctctgtgg aggcagacat aggacccca    180 acaaacagca tgcaggttgg agccagcca caggacccag gtaaggggcc ctgggtcctt    240

<210> SEQ ID NO 28
<211> LENGTH: 95
<212> TYPE: DNA
<213> ORGANISM: Mus musculus

<400> SEQUENCE: 28
```

```
                                                         60
tttatgaggt gggagctggg ctctccctga tgtattattc agctccctgg agttggccag 95
ctcctgttac actggccaca gccctgggca tccgc
```

<210> SEQ ID NO 29
<211> LENGTH: 185
<212> TYPE: DNA
<213> ORGANISM: Mus musculus

<400> SEQUENCE: 29

```
                                                         60
tgccatggtg actttaaagc caggttgctg ccccagcaca ggcctccag tctaccctca 120
ctagaaaaca cacccaggc actttccacc acctctcaaa ggtgaaaccc aaggctggtc 180
tagagaatga attatggatc ctcgctgtcc gtgccaccca gctagtccca gcggctcaga 185
cactg
```

<210> SEQ ID NO 30
<211> LENGTH: 335
<212> TYPE: DNA
<213> ORGANISM: Artificial Sequence
<220> FEATURE:
<223> OTHER INFORMATION: Synthetic Construct

<400> SEQUENCE: 30

```
                                                         60
ctgcagctca gcctactact tgctttccag gctgttccta gttcccatgt cagctgcttg 120
tgctttccag agacaaaaca ggaataatag atgtcattaa atatacattg ggccccaggc 180
ggtcaatgtg gcagcctgag cctccttcc atctctgtgg aggcagacat aggaccccca 240
acaaacagca tgcaggttgg gagccagcca caggacccag gtaaggggcc ctgggtcctt 300
tttatgaggt gggagctggg ctctccctga tgtattattc agctccctgg agttggccag 335
ctcctgttac actggccaca gccctgggca tccgc
```

<210> SEQ ID NO 31
<211> LENGTH: 425
<212> TYPE: DNA
<213> ORGANISM: Artificial Sequence
<220> FEATURE:
<223> OTHER INFORMATION: Synthetic Construct

<400> SEQUENCE: 31

```
                                                         60
ctgcagctca gcctactact tgctttccag gctgttccta gttcccatgt cagctgcttg 120
tgctttccag agacaaaaca ggaataatag atgtcattaa atatacattg ggccccaggc 180
ggtcaatgtg gcagcctgag cctccttcc atctctgtgg aggcagacat aggaccccca 240
acaaacagca tgcaggttgg gagccagcca caggacccag gtaaggggcc ctgggtcctt 300
tgccatggtg actttaaagc caggttgctg ccccagcaca ggcctccag tctaccctca 360
ctagaaaaca cacccaggc actttccacc acctctcaaa ggtgaaaccc aaggctggtc 420
tagagaatga attatggatc ctcgctgtcc gtgccaccca gctagtccca gcggctcaga 425
cactg
```

<210> SEQ ID NO 32
<211> LENGTH: 280
<212> TYPE: DNA
<213> ORGANISM: Mus musculus

<400> SEQUENCE: 32

```
                                                         60
tttatgaggt gggagctggg ctctccctga tgtattattc agctccctgg agttggccag 120
ctcctgttac actggccaca gccctgggca tccgctgcca tggtgacttt aaagccaggt
```
tgctgcccca gcacaggcct cccagtctac cctcactaga aaacaacacc caggcacttt    180
ccaccacctc tcaaaggtga aacccaaggc tggtctagag aatgaattat ggatcctcgc    240
tgtccgtgcc acccagctag tcccagcggc tcagacactg    280

<210> SEQ ID NO 33
<211> LENGTH: 520
<212> TYPE: DNA
<213> ORGANISM: Artificial Sequence
<220> FEATURE:
<223> OTHER INFORMATION: Synthetic Construct

<400> SEQUENCE: 33
tttatgaggt gggagctggg ctctccctga tgtattattc agctccctgg agttggccag     60
ctcctgttac actggccaca gccctgggca tccgcctgca gctcagccta ctacttgctt    120
tccaggctgt tcctagttcc catgtcagct gcttgtgctt tccagagaca aaacaggaat    180
aatagatgtc attaaatata cattgggccc caggcggtca atgtggcagc ctgagcctcc    240
tttccatctc tgtggaggca gacataggac ccccaacaaa cagcatgcag gttgggagcc    300
agccacagga cccaggtaag gggccctggg tcctttgcca tggtgacttt aaagccaggt    360
tgctgcccca gcacaggcct cccagtctac cctcactaga aaacaacacc caggcacttt    420
ccaccacctc tcaaaggtga aacccaaggc tggtctagag aatgaattat ggatcctcgc    480
tgtccgtgcc acccagctag tcccagcggc tcagacactg    520

<210> SEQ ID NO 34
<211> LENGTH: 520
<212> TYPE: DNA
<213> ORGANISM: Artificial Sequence
<220> FEATURE:
<223> OTHER INFORMATION: Synthetic Construct

<400> SEQUENCE: 34
tgccatggtg actttaaagc caggttgctg ccccagcaca ggcctcccag tctaccctca     60
ctagaaaaca cacccaggc actttccacc acctctcaaa ggtgaaaccc aaggctggtc    120
tagagaatga attatggatc ctcgctgtcc gtgccaccca gctagtccca gcggctcaga    180
cactgctgca gctcagccta ctacttgctt tccaggctgt tcctagttcc catgtcagct    240
gcttgtgctt tccagagaca aaacaggaat aatagatgtc attaaatata cattgggccc    300
caggcggtca atgtggcagc ctgagcctcc tttccatctc tgtggaggca gacataggac    360
ccccaacaaa cagcatgcag gttgggagcc agccacagga cccaggtaag gggccctggg    420
tcctttttat gaggtgggag ctgggctctc cctgatgtat tattcagctc cctggagttg    480
gccagctcct gttacactgg ccacagccct gggcatccgc    520

<210> SEQ ID NO 35
<211> LENGTH: 520
<212> TYPE: DNA
<213> ORGANISM: Artificial Sequence
<220> FEATURE:
<223> OTHER INFORMATION: Synthetic Construct

<400> SEQUENCE: 35
tttatgaggt gggagctggg ctctccctga tgtattattc agctccctgg agttggccag     60
ctcctgttac actggccaca gccctgggca tccgctgcca tggtgacttt aaagccaggt    120
tgctgcccca gcacaggcct cccagtctac cctcactaga aaacaacacc caggcacttt    180

| | |
|---|---|
| ccaccacctc tcaaaggtga aacccaaggc tggtctagag aatgaattat ggatcctcgc | 240 |
| tgtccgtgcc acccagctag tcccagcggc tcagacactg ctgcagctca gcctactact | 300 |
| tgctttccag gctgttccta gttcccatgt cagctgcttg tgctttccag agacaaaaca | 360 |
| ggaataatag atgtcattaa atatacattg ggcccaggc ggtcaatgtg gcagcctgag | 420 |
| cctcctttcc atctctgtgg aggcagacat aggaccccca acaaacagca tgcaggttgg | 480 |
| gagccagcca caggacccag gtaaggggcc ctgggtcctt | 520 |

<210> SEQ ID NO 36
<211> LENGTH: 964
<212> TYPE: DNA
<213> ORGANISM: Artificial Sequence
<220> FEATURE:
<223> OTHER INFORMATION: Synthetic Construct

<400> SEQUENCE: 36

| | |
|---|---|
| tgcagctcag cctactactt gctttccagg ctgttcctag ttcccatgtc agctgcttgt | 60 |
| gctttccaga gacaaaacag gaataataga tgtcattaaa tatacattgg gccccaggcg | 120 |
| gtcaatgtgg cagcctgagc ctcctttcca tctctgtgga ggcagacata gacccccaa | 180 |
| caaacagcat gcaggttggg agccagccac aggacccagg taaggggccc tgggtcctta | 240 |
| agcttctgcc actggctccg gcattgcaga gagaagagaa ggggcggcag actggagagc | 300 |
| tgggctccat ttttgttcct tggtgccctg ccctccca tgacctgcag agacattcag | 360 |
| cctgccaggc tttatgaggt gggagctggg ctctccctga tgtattattc agctccctgg | 420 |
| agttggccag ctcctgttac actggccaca gccctgggca tccgcttctc acttctagtt | 480 |
| tcccctccaa ggtaatgtgg tgggtcatga tcattctatc ctggcttcag ggacctgact | 540 |
| ccactttggg gccattcgag gggtctaggg tagatgatgt ccccctgtgg ggattaatgt | 600 |
| cctgctctgt aaaactgagc tagctgagat ccaggagggc ttggccagag acagcaagtt | 660 |
| gttgccatgt tgactttaaa gccaggttgc tgccccagca caggcctccc agtctaccct | 720 |
| cactagaaaa caacacccag gcactttcca ccacctctca aaggtgaaac ccaaggctgg | 780 |
| tctagagaat gaattatgga tcctcgctgt ccgtgccacc cagctagtcc cagcggctca | 840 |
| gacactgagg agagactgta ggttcagcta caagcaaaaa gacctagctg gtctccaagc | 900 |
| agtgtctcca gtccctgaa cctgtgacac ctgccccagg catcatcagg cacagagggc | 960 |
| cacc | 964 |

<210> SEQ ID NO 37
<211> LENGTH: 519
<212> TYPE: DNA
<213> ORGANISM: Artificial Sequence
<220> FEATURE:
<223> OTHER INFORMATION: Synthetic Construct

<400> SEQUENCE: 37

| | |
|---|---|
| tgcagctcag cctactactt gctttccagg ctgttcctag ttcccatgtc agctgcttgt | 60 |
| gctttccaga gacaaaacag gaataataga tgtcattaaa tatacattgg gccccaggcg | 120 |
| gtcaatgtgg cagcctgagc ctcctttcca tctctgtgga ggcagacata gacccccaa | 180 |
| caaacagcat gcaggttggg agccagccac aggacccagg taaggggccc tgggtccttt | 240 |
| ttatgaggtg gggagctgggc tctccctgat gtattattca gctccctgga gttggccagc | 300 |
| tcctgttaca ctggccacag ccctgggcat ccgctgccat ggtgacttta agccaggtt | 360 |
| gctgccccag cacaggcctc ccagtctacc ctcactagaa acaacacccc aggcactttc | 420 |

```
caccacctct caaaggtgaa acccaaggct ggtctagaga atgaattatg gatcctcgct    480
gtccgtgcca cccagctagt cccagcggct cagacactg                          519
```